US012741036B2

(12) United States Patent
Francois et al.

(10) Patent No.: US 12,741,036 B2
(45) Date of Patent: Sep. 22, 2026

(54) VIRAL VECTOR THERAPY

(71) Applicant: Apellis Pharmaceuticals, Inc., Waltham, MA (US)

(72) Inventors: Cedric Francois, Prospect, KY (US); Lukas Scheibler, Telluride, CO (US)

(73) Assignee: Apellis Pharmaceuticals, Inc., Waltham, MA (US)

( * ) Notice: Subject to any disclaimer, the term of this patent is extended or adjusted under 35 U.S.C. 154(b) by 1173 days.

(21) Appl. No.: 17/624,755

(22) PCT Filed: Jul. 2, 2020

(86) PCT No.: PCT/US2020/040741
§ 371 (c)(1),
(2) Date: Jan. 4, 2022

(87) PCT Pub. No.: WO2021/007111
PCT Pub. Date: Jan. 14, 2021

(65) Prior Publication Data

US 2022/0249706 A1 Aug. 11, 2022

Related U.S. Application Data

(60) Provisional application No. 62/935,569, filed on Nov. 14, 2019, provisional application No. 62/875,925, (Continued)

(51) Int. Cl.
*C12N 15/113* (2010.01)
*A61K 38/17* (2006.01)
(Continued)

(52) U.S. Cl.
CPC ............ *A61K 48/0083* (2013.01); *A61P 7/00* (2018.01); *A61P 21/00* (2018.01); *A61P 33/00* (2018.01);
(Continued)

(58) Field of Classification Search
CPC .. A61P 37/02; A61P 7/00; A61P 21/00; A61K 38/1725; A61K 38/00
See application file for complete search history.

(56) References Cited

U.S. PATENT DOCUMENTS

| | | | |
|---|---|---|---|
| 3,687,808 | A | 8/1972 | Merigan et al. |
| 4,299,838 | A | 11/1981 | Durlach |

(Continued)

FOREIGN PATENT DOCUMENTS

| | | | |
|---|---|---|---|
| JP | 2016-505527 | A | 2/2016 |
| WO | WO-91/02788 | A1 | 3/1991 |

(Continued)

OTHER PUBLICATIONS

Minna U Kaikkonen et al: "How to avoid complement attack in baculovirus-mediated gene delivery", Journal of Invertebrate Pathology, vol. 107, Jul. 22, 2011 (Jul. 22, 2011), pp. S71-S79, XP028244448, ISSN: 0022-2011, DOI: 10.1016/J.JIP.2011.05.007.

(Continued)

*Primary Examiner* — Barry A Chestnut

(74) *Attorney, Agent, or Firm* — Choate, Hall & Stewart LLP; Brenda Herschbach Jarrell; Rolando Medina

(57) ABSTRACT

Methods and compositions for combined therapy with viral vectors and complement inhibitors are described.

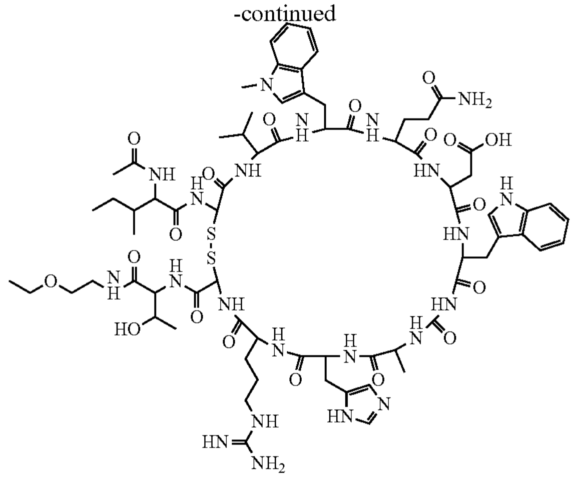

20 Claims, 3 Drawing Sheets

Specification includes a Sequence Listing.

Related U.S. Application Data filed on Jul. 18, 2019, provisional application No. 62/871,700, filed on Jul. 8, 2019, provisional application No. 62/871,058, filed on Jul. 5, 2019.

(51) Int. Cl.

| | |
|---|---|
| ***A61K 48/00*** | (2006.01) |
| ***A61P 7/00*** | (2006.01) |
| ***A61P 21/00*** | (2006.01) |
| ***A61P 33/00*** | (2006.01) |
| ***C07K 16/18*** | (2006.01) |
| ***C12N 9/22*** | (2006.01) |
| ***C12N 15/86*** | (2006.01) |

(52) U.S. Cl.

CPC .............. *C07K 16/18* (2013.01); *C12N 15/86* (2013.01); *C07K 2317/76* (2013.01); *C12N 2750/14143* (2013.01)

(56) References Cited

U.S. PATENT DOCUMENTS

| | | | |
|---|---|---|---|
| 4,576,750 | A | 3/1986 | Pitzenberger |
| 4,797,368 | A | 1/1989 | Carter et al. |
| 4,845,205 | A | 7/1989 | Huynh Dinh et al. |
| 4,870,097 | A | 9/1989 | Makovec et al. |
| 4,981,957 | A | 1/1991 | Lebleu et al. |
| 5,118,800 | A | 6/1992 | Smith et al. |
| 5,134,066 | A | 7/1992 | Rogers et al. |
| 5,139,941 | A | 8/1992 | Muzyczka et al. |
| 5,175,273 | A | 12/1992 | Bischofberger et al. |
| 5,319,080 | A | 6/1994 | Leumann |
| 5,359,044 | A | 10/1994 | Cook et al. |
| 5,367,066 | A | 11/1994 | Urdea et al. |
| 5,432,272 | A | 7/1995 | Benner |
| 5,457,187 | A | 10/1995 | Gmeiner et al. |
| 5,457,191 | A | 10/1995 | Cook et al. |
| 5,459,255 | A | 10/1995 | Cook et al. |
| 5,478,745 | A | 12/1995 | Samulski et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,681,941 | A | 10/1997 | Cook et al. |
| 5,720,720 | A | 2/1998 | Laske et al. |
| 5,741,683 | A | 4/1998 | Zhou et al. |
| 5,750,692 | A | 5/1998 | Cook et al. |
| 5,776,970 | A | 7/1998 | Shechter et al. |
| 5,801,030 | A | 9/1998 | McVey et al. |
| 5,804,413 | A | 9/1998 | DeLuca |
| 5,837,511 | A | 11/1998 | Falck-Pedersen et al. |
| 5,837,532 | A | 11/1998 | Preston et al. |
| 5,846,782 | A | 12/1998 | Wickham et al. |
| 5,849,561 | A | 12/1998 | Falck-Pedersen |
| 5,849,572 | A | 12/1998 | Glorioso et al. |
| 5,994,136 | A | 11/1999 | Naldini et al. |
| 6,001,650 | A | 12/1999 | Colosi |
| 6,011,020 | A | 1/2000 | Gold et al. |
| 6,015,886 | A | 1/2000 | Dale et al. |
| 6,051,698 | A | 4/2000 | Janjic et al. |
| 6,057,152 | A | 5/2000 | Samulski et al. |
| 6,147,200 | A | 11/2000 | Manoharan et al. |
| 6,147,204 | A | 11/2000 | Gold et al. |
| 6,156,303 | A | 12/2000 | Russell et al. |
| 6,165,782 | A | 12/2000 | Naldini et al. |
| 6,166,197 | A | 12/2000 | Cook et al. |
| 6,168,778 | B1 | 1/2001 | Janjic et al. |
| 6,169,057 | B1 | 1/2001 | Lovatt |
| 6,204,059 | B1 | 3/2001 | Samulski et al. |
| 6,214,790 | B1 | 4/2001 | Richelson et al. |
| 6,222,025 | B1 | 4/2001 | Cook et al. |
| 6,235,887 | B1 | 5/2001 | Froehler et al. |
| 6,268,213 | B1 | 7/2001 | Samulski et al. |
| 6,319,897 | B1 | 11/2001 | Lambris et al. |
| 6,380,368 | B1 | 4/2002 | Froehler et al. |
| 6,426,335 | B1 | 7/2002 | Janjic et al. |
| 6,428,953 | B1 | 8/2002 | Naldini et al. |
| 6,491,907 | B1 | 12/2002 | Rabinowitz et al. |
| 6,515,002 | B2 | 2/2003 | Illig et al. |
| 6,528,640 | B1 | 3/2003 | Beigelman et al. |
| 6,617,438 | B1 | 9/2003 | Beigelman et al. |
| 6,639,062 | B2 | 10/2003 | Manoharan et al. |
| 6,660,514 | B1 | 12/2003 | Zolotukhin et al. |
| 6,676,943 | B1 | 1/2004 | Hostetter et al. |
| 6,897,290 | B1 | 5/2005 | Atkinson et al. |
| 6,951,753 | B2 | 10/2005 | Shenk et al. |
| 6,998,468 | B2 | 2/2006 | Fung et al. |
| 7,041,796 | B2 | 5/2006 | Welcher et al. |
| 7,045,610 | B2 | 5/2006 | Dempcy et al. |
| 7,049,282 | B2 | 5/2006 | Frank et al. |
| 7,094,604 | B2 | 8/2006 | Snyder et al. |
| 7,138,530 | B2 | 11/2006 | Subasinghe et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,399,845 | B2 | 7/2008 | Seth et al. |
| 7,427,672 | B2 | 9/2008 | Imanishi et al. |
| 7,439,065 | B2 | 10/2008 | Ferrari et al. |
| 7,495,088 | B1 | 2/2009 | Brakel et al. |
| 7,521,049 | B2 | 4/2009 | Wiegand et al. |
| 7,588,772 | B2 | 9/2009 | Kay et al. |
| 7,592,322 | B2 | 9/2009 | Barik |
| 7,737,265 | B2 | 6/2010 | Akinc et al. |
| 7,740,844 | B2 | 6/2010 | Hong et al. |
| 7,758,859 | B2 | 7/2010 | Fuh et al. |
| 7,790,449 | B2 | 9/2010 | Gao et al. |
| 7,790,878 | B2 | 9/2010 | Barik |
| 7,919,473 | B2 | 4/2011 | De Fougerolles et al. |
| 7,947,659 | B2 | 5/2011 | de Fougerolles et al. |
| 8,293,719 | B2 | 10/2012 | De Fougerolles et al. |
| 8,338,157 | B2 | 12/2012 | Jantz et al. |
| 8,445,251 | B2 | 5/2013 | Smith et al. |
| 8,569,253 | B2 | 10/2013 | Ando et al. |
| 8,632,764 | B2 | 1/2014 | Xiao et al. |
| 8,802,437 | B2 | 8/2014 | Tremblay et al. |
| 8,846,578 | B2 | 9/2014 | McCray et al. |
| 8,877,917 | B2 | 11/2014 | Forst et al. |

(56) References Cited

U.S. PATENT DOCUMENTS

| | | | |
|---|---|---|---|
| 8,921,112 | B2 | 12/2014 | Cai et al. |
| 8,956,828 | B2 | 2/2015 | Bonini et al. |
| 8,993,530 | B2 | 3/2015 | Roelvink et al. |
| 9,005,973 | B2 | 4/2015 | Cost et al. |
| 2003/0125286 | A1 | 7/2003 | Hauser et al. |
| 2003/0181377 | A1 | 9/2003 | Hallahan et al. |
| 2005/0020529 | A1 | 1/2005 | Dietz |
| 2005/0271733 | A1 | 12/2005 | Burkoth et al. |
| 2006/0177819 | A1 | 8/2006 | Smith et al. |
| 2007/0287831 | A1 | 12/2007 | Seth et al. |
| 2009/0088398 | A1 | 4/2009 | Gregory et al. |
| 2009/0175897 | A1 | 7/2009 | Tang et al. |
| 2009/0305344 | A1 | 12/2009 | Polo et al. |
| 2010/0008889 | A1 | 1/2010 | Mayall |
| 2010/0267805 | A1 | 10/2010 | McCallus et al. |
| 2011/0033935 | A1 | 2/2011 | Jantz et al. |
| 2011/0113509 | A1 | 5/2011 | Jantz et al. |
| 2011/0224282 | A1 | 9/2011 | De Fougerolles et al. |
| 2012/0283318 | A1 | 11/2012 | Mei et al. |
| 2013/0156845 | A1 | 6/2013 | Manoharan et al. |
| 2013/0224863 | A1 | 8/2013 | Jantz et al. |
| 2014/0087426 | A1 | 3/2014 | Liu et al. |
| 2014/0248305 | A1 | 9/2014 | Ertl et al. |
| 2014/0296129 | A1 | 10/2014 | Flammer et al. |
| 2014/0315835 | A1 | 10/2014 | Rajeev et al. |
| 2014/0350071 | A1 | 11/2014 | Sehgal et al. |
| 2015/0050243 | A1 | 2/2015 | Kaczmarczyk et al. |
| 2015/0079064 | A1 | 3/2015 | Gersbach et al. |
| 2015/0093831 | A1 | 4/2015 | Brennan et al. |
| 2015/0118216 | A1 | 4/2015 | Liu et al. |
| 2015/0166969 | A1 | 6/2015 | Takeuchi et al. |
| 2015/0197746 | A1 | 7/2015 | Rajeev et al. |
| 2016/0339066 | A1 | 11/2016 | Szalay et al. |
| 2019/0381129 | A1 | 12/2019 | Grossi et al. |
| 2020/0038516 | A1 | 2/2020 | Grossi et al. |

FOREIGN PATENT DOCUMENTS

| | | | |
|---|---|---|---|
| WO | WO-96/04394 | A1 | 2/1996 |
| WO | WO-97/12986 | A2 | 4/1997 |
| WO | WO-98/15637 | A1 | 4/1998 |
| WO | WO-98/47002 | A2 | 10/1998 |
| WO | WO-1998/46270 | A2 | 10/1998 |
| WO | WO-98/53087 | A1 | 11/1998 |
| WO | WO-99/06583 | A1 | 2/1999 |
| WO | WO-00/029033 | A2 | 5/2000 |
| WO | WO-2001/088198 | A1 | 11/2001 |
| WO | WO-2003/042397 | A2 | 5/2003 |
| WO | WO-2004/026328 | A1 | 4/2004 |
| WO | WO-2005/033321 | A2 | 4/2005 |
| WO | WO-2005/070459 | A1 | 8/2005 |
| WO | WO-2006/110689 | A2 | 10/2006 |
| WO | WO-2007/044668 | A2 | 4/2007 |
| WO | WO-2007/062249 | A2 | 5/2007 |
| WO | WO-2008/106186 | A2 | 9/2008 |
| WO | WO-2009/043027 | A2 | 4/2009 |
| WO | WO-2009/046198 | A2 | 4/2009 |
| WO | WO-2009/089542 | A2 | 7/2009 |
| WO | WO-2009/130208 | A1 | 10/2009 |
| WO | WO-2010/006282 | A2 | 1/2010 |
| WO | WO-2010/127336 | A1 | 11/2010 |
| WO | WO-2010/135717 | A2 | 11/2010 |
| WO | WO-2012/030683 | A2 | 3/2012 |
| WO | WO-2012/040259 | A2 | 3/2012 |
| WO | WO-2012/155107 | A1 | 11/2012 |
| WO | WO-2014/078731 | A2 | 5/2014 |
| WO | WO-2015/103438 | A2 | 7/2015 |
| WO | WO-2018/187813 | A1 | 10/2018 |
| WO | WO-2019/118938 | A1 | 6/2019 |
| WO | WO-2021/00711 | A1 | 1/2021 |

OTHER PUBLICATIONS

Ricklin Daniel et al: "The renaissance of complement therapeutics", Nature Reviews. Nephrology, vol. 14, No. 1, Dec. 4, 2017 (Dec. 4, 2017), pp. 26-47, XP055782678, ISSN: 1759-5061, DOI: 10.1038/nrneph.2017.156.

Rogers Geoffrey L. et al: "Innate Immune Responses to AAV Vectors", Frontiers in Microbiology, vol. 2, Sep. 19, 2011 (Sep. 19, 2011), p. 194, XP093048623, DOI: 10.3389/fmicb.2011.00194 Retrieved from the Internet: URL:https://www.ncbi.nlm.nih.gov/pmc/artic les/PMC3175613/pdf/fmicb-02-00194.pdf>.

Zelek Wioleta M et al: "Compendium of current complement therapeutics", Molecular Immunology, Pergamon, GB, vol. 114, Aug. 22, 2019 (Aug. 22, 2019), pp. 341-352, XP085844143, ISSN: 0161-5890, DOI: 10.1016/J.MOLIMM.2019.07.030.

Asokan, A. et al., The AAV vector toolkit: poised at the clinical crossroads, Mol Ther., 20(4):699-708 (2012).

Asuri, P. et al., Directed evolution of adeno-associated virus for enhanced gene delivery and gene targeting in human pluripotent stem cells, Mol Ther., 20(2):329-38 (2012).

Baruteau, J. et al., Gene therapy for monogenic liver diseases: clinical successes, current challenges and future prospects, J Inherit Metab Dis., 40(4):497-517 (2017).

Bordet, et al., Drug Discov. Today, S1359-6446 (18) 30472.0 (2019).

Chu, G. and Sharp, P.A., SV40 DNA transfection of cells in suspension: analysis of efficiency of transcription and translation of T-antigen, Gene, 13(2):197-202 (1981).

Cichon, G. et al., Complement activation by recombinant adenoviruses, Gene Therapy, 8:1794-1800 (2001).

Colella, P. et al., Emerging Issues in AAV-Mediated In Vivo Gene Therapy, Mol Ther Methods Clin Dev., 8:87-104 (2017).

Cotten, M. et al., High-efficiency receptor-mediated delivery of small and large (48 kilobase gene constructs using the endosome-disruption activity of defective or chemically inactivated adenovirus particles, Proc Natl Acad Sci USA, 89(13):6094-8 (1992).

Curiel, D. T., High-efficiency gene transfer employing adenovirus-polylysine-DNA complexes, Nat Immun., 13(2-3):141-64 (1994).

Deltcheva, E. et al., CRISPR RNA maturation by trans-encoded small RNA and host factor RNase III, Nature, 471(7340):602-7 (2011).

Duan, Dongsheng, Systemic AAV Micro-dystrophin Gene Therapy for Duchenne Muscular Dystrophy, Mol Ther., 26(10):2337-2356 (2018).

Fisher, K. et al., Transduction with recombinant adeno-associated virus for gene therapy is limited by leading-strand synthesis, J Virol, 70(1):520-32 (1996).

Graham, F.L. and Van Der Eb, A.J., A new technique for the assay of infectivity of human adenovirus 5 DNA, Virology, 52(2):456-67 (1973).

International Search Report for PCT/US20/40741 (Viral Vector Therapy, filed Jul. 2, 2020) received by ISA/US, 4 pages (Oct. 22, 2020).

Jinek, M. et al., A programmable dual-RNA-guided DNA endonuclease in adaptive bacterial immunity, Science, 337(6096):816-21 (2012).

Katragadda, M. et al., Hydrophobic effect and hydrogen bonds account for the improved activity of a complement inhibitor, compstatin, J Med Chem., 49(15):4616-22 (2006).

Katragadda, M. et al., Thermodynamic studies on the interaction of the third complement component and its inhibitor, compstatin, J Biol Chem., 279(53):54987-95 (2004).

Kelleher, Z.T. and Vos, J.M., Long-term episomal gene delivery in human lymphoid cells using human and avian adenoviral-assisted transfection, Biotechniques, 17(6):1110-7 (1994).

Mahasreshti, P. et al., Adenovirus-mediated soluble FLT-1 gene therapy for ovarian carcinoma, Clin Cancer Res., 7(7):2057-66 (2001).

Miyatake, S. et al., Transcriptional targeting of herpes simplex virus for cell-specific replication, J Virol., 71(7):5124-32 (1997).

Mori, A. et al., Soluble Flt-1 gene therapy for peritoneal metastases using HVJ-cationic liposomes, Gene Ther., 7(12):1027-33 (2000).

Morikis, D. et al., Improvement of the anti-C3 activity of compstatin using rational and combinatorial approaches, Biochem Soc Trans., 32(Pt 1):28-32 (2004).

(56) References Cited

OTHER PUBLICATIONS

Morikis, D. et al., Solution structure of Compstatin, a potent complement inhibitor, Protein Sci, 7(3):619-27 (1998).
Muzyczka, N., Use of adeno-associated virus as a general transduction vector for mammalian cells, Curr Top Microbiol Immunol, 158:97-129 (1992).
Ng, E. et al., Pegaptanib, a targeted anti-VEGF aptamer for ocular vascular disease, Nat Rev Drug Discov., 5(2):123-32 (2006).
Sahu, A. et al., Interaction of vaccinia virus complement control protein with human complement proteins: factor I-mediated degradation of C3b to iC3b1 inactivates the alternative complement pathway, J Immunol., 160(11):5596-604 (1998).
Sandig, V. et al., HBV-derived promoters direct liver-specific expression of an adenovirally transduced LDL receptor gene, Gene Ther., 3(11):1002-9 (1996).
Schubart, A. et al., Small-molecule factor B inhibitor for the treatment of complement-mediated diseases, Proc Natl Acad Sci USA, 116(16):7926-7931 (2019).
Sharma, A. et al., Transduction efficiency of AAV 2/6, 2/8 and 2/9 vectors for delivering genes in human corneal fibroblasts, Brain Res Bull, 81(2-3):273-8 (2010).
Soulika, A. et al., Compstatin inhibits complement activation by binding to the beta-chain of complement factor 3, Mol Immunol., 43(12):2023-9 (2006).
Sui, G. et al., A DNA vector-based RNAi technology to suppress gene expression in mammalian cells, Proc Natl Acad Sci USA, 99(8):5515-20 (2002).
Takayama, K. et al., Suppression of tumor angiogenesis and growth by gene transfer of a soluble form of vascular endothelial growth factor receptor into a remote organ, Cancer Res., 60(8):2169-77 (2000).
Walport, M.J., Complement. First of two parts, N Engl J Med., 344(14):1058-66 (2001).
Written Opinion for PCT/US20/40741 (Viral Vector Therapy, filed Jul. 2, 2020) received by ISA/US, 10 pages (Oct. 22, 2020).
Zhang, H. et al., Adenovirus-adeno-associated virus hybrid for large-scale recombinant adeno-associated virus production, Hum Gene Ther., 20(9):922-9 (2009).
Zhang, L. et al., A simple glycol nucleic acid, J Am Chem Soc., 127(12):4174-5 (2005).
Zhang, Y. and Duan, D., Novel mini-dystrophin gene dual adeno-associated virus vectors restore neuronal nitric oxide synthase expression at the sarcolemma, Hum Gene Ther., 23(1):98-103 (2012).
Georgopoulos, L. et al., Preclinical evaluation of innate immunity to baculovirus gene therapy vectors in whole human blood, Molecular Immunology, 46:2911-2917 (2009).
Qu, H. et al., Novel analogues of the therapeutic complement inhibitor compstatin with significantly improved affinity and potency, Mol Immunol., 48(4):481-9 (2011).

SEQUENCE LISTING

```
<160> NUMBER OF SEQ ID NOS: 75

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(12)
<223> OTHER INFORMATION: Disulfide bond

<400> SEQUENCE: 1

Ile Cys Val Val Gln Asp Trp Gly His His Arg Cys Thr
1               5                   10


<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(19)
<223> OTHER INFORMATION: Any independently selected amino acid or amino
      acid analog
<220> FEATURE:
<221> NAME/KEY: MISC_FEATURE
<222> LOCATION: (1)..(19)
<223> OTHER INFORMATION: This region may encompass 2 to 19 residues,
      wherein some residues may be absent
<220> FEATURE:
<221> NAME/KEY: MOD_RES
<222> LOCATION: (22)..(22)
<223> OTHER INFORMATION: Trp or an analog of Trp
<220> FEATURE:
<221> NAME/KEY: MOD_RES
<222> LOCATION: (24)..(42)
<223> OTHER INFORMATION: Any independently selected amino acid or amino
      acid analog
<220> FEATURE:
<221> NAME/KEY: MISC_FEATURE
<222> LOCATION: (24)..(42)
<223> OTHER INFORMATION: This region may encompass 2 to 19 residues,
      wherein some residues may be absent
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp, an analog of Trp, or other amino acid or
```

amino acid analog comprising at least one aromatic ring
<220> FEATURE:
<221> NAME/KEY: MOD_RES
<222> LOCATION: (4)..(4)
<223> OTHER INFORMATION: Trp, an analog of Trp, or other amino acid or amino acid analog comprising at least one aromatic ring
<220> FEATURE:
<223> OTHER INFORMATION: See specification as filed for detailed description of substitutions and preferred embodiments

<400> SEQUENCE: 3

Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Trp, an analog of Trp, or other amino acid or amino acid analog comprising at least one aromatic side chain
<220> FEATURE:
<221> NAME/KEY: MOD_RES
<222> LOCATION: (4)..(4)
<223> OTHER INFORMATION: Trp, an analog of Trp, or other amino acid or amino acid analog comprising at least one aromatic side chain
<220> FEATURE:
<221> NAME/KEY: MOD_RES
<222> LOCATION: (6)..(6)
<223> OTHER INFORMATION: His, Ala, analog of Ala, Phe, Trp or analog of Trp
<220> FEATURE:
<223> OTHER INFORMATION: See specification as filed for detailed description of substitutions and preferred embodiments

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(3)
<223> OTHER INFORMATION: Any independently selected amino acid or amino acid analog
<220> FEATURE:
<221> NAME/KEY: MOD_RES
<222> LOCATION: (4)..(4)
<223> OTHER INFORMATION: Trp or analog of Trp
<220> FEATURE:
<221> NAME/KEY: MOD_RES
<222> LOCATION: (7)..(7)
<223> OTHER INFORMATION: Trp or analog of Trp
<220> FEATURE:
<221> NAME/KEY: MOD_RES
<222> LOCATION: (9)..(13)
<223> OTHER INFORMATION: Any independently selected amino acid or amino acid analog
<220> FEATURE:
<223> OTHER INFORMATION: See specification as filed for detailed description of substitutions and preferred embodiments

<400> SEQUENCE: 5

```
Xaa Xaa Xaa Xaa Gln Asp Xaa Gly Xaa Xaa Xaa Xaa Xaa
1               5                   10


<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: MISC_FEATURE
<222> LOCATION: (1)..(2)
<223> OTHER INFORMATION: This region may encompass 1 to 2 residues,
      wherein some positions may be absent
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising
      Thr-Ala-Asn, wherein a c-term -OH of any of the L-Thr, D-Thr, Ile,
      Val, Gly, Ala or Asn is optionally replaced by a second blocking
      moiety
<220> FEATURE:
<221> NAME/KEY: MISC_FEATURE
<222> LOCATION: (14)..(16)
<223> OTHER INFORMATION: This region may encompass 1 to 3 residues,
      wherein some positions may be absent
<220> FEATURE:
<223> OTHER INFORMATION: See specification as filed for detailed
      description of substitutions and preferred embodiments

<400> SEQUENCE: 6

Xaa Xaa Cys Val Xaa Gln Asp Xaa Gly Xaa His Arg Cys Xaa Xaa Xaa
1               5                   10                  15


<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: MISC_FEATURE
<222> LOCATION: (1)..(2)
```

<223> OTHER INFORMATION: This region may encompass 1 to 2 residues, wherein some positions may be absent
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of Trp
<220> FEATURE:
<221> NAME/KEY: MOD_RES
<222> LOCATION: (8)..(8)
<223> OTHER INFORMATION: Independently selected from Trp or analogs of Trp
<220> FEATURE:
<221> NAME/KEY: MOD_RES
<222> LOCATION: (10)..(10)
<223> OTHER INFORMATION: His, Ala or an analog of Ala, Phe, Trp or an analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide selected from Thr-Ala or Thr-Asn, or a tripeptide comprising Thr-Ala-Asn, wherein a c-term -OH of any of L-Thr, D-Thr, Ile, Val, Gly, Ala, or Asn is optionally replaced by -NH2
<220> FEATURE:
<221> NAME/KEY: MISC_FEATURE
<222> LOCATION: (14)..(16)
<223> OTHER INFORMATION: This region may encompass 1 to 3 residues, wherein some positions may be absent
<220> FEATURE:
<223> OTHER INFORMATION: See specification as filed for detailed description of substitutions and preferred embodiments

<400> SEQUENCE: 7

Xaa Xaa Cys Val Xaa Gln Asp Xaa Gly Xaa His Arg Cys Xaa Xaa Xaa
1 5 10 15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term H
<220> FEATURE:
<223> OTHER INFORMATION: C-term CONH2

<400> SEQUENCE: 8

Ile Cys Val Val Gln Asp Trp Gly His His Arg Cys Thr
1 5 10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<223> OTHER INFORMATION: C-term CONH2

<400> SEQUENCE: 9

Ile Cys Val Val Gln Asp Trp Gly His His Arg Cys Thr
1 5 10

-continued

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<223> OTHER INFORMATION: C-term CONH2

<400> SEQUENCE: 10

Ile Cys Val Tyr Gln Asp Trp Gly Ala His Arg Cys Thr
1 5 10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<223> OTHER INFORMATION: C-term COOH

<400> SEQUENCE: 11

Ile Cys Val Trp Gln Asp Trp Gly Ala His Arg Cys Thr
1 5 10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<223> OTHER INFORMATION: C-term CONH2

<400> SEQUENCE: 12

Ile Cys Val Trp Gln Asp Trp Gly Ala His Arg Cys Thr
1 5 10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: d-Thr
<220> FEATURE:
<223> OTHER INFORMATION: C-term COOH

<400> SEQUENCE: 13

Ile Cys Val Trp Gln Asp Trp Gly Ala His Arg Cys Thr
1 5 10

<210> SEQ ID NO 14
<211> LENGTH: 13
<212> TYPE: PRT

<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term CONH2

<400> SEQUENCE: 14

Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-Nal
<220> FEATURE:
<223> OTHER INFORMATION: C-term COOH

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term CONH2

<400> SEQUENCE: 17

Ile Cys Val Gly Gln Asp Trp Gly Ala His Arg Cys Thr
1 5 10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term COOH

<400> SEQUENCE: 18

Ile Cys Val Gly Gln Asp Trp Gly Ala His Arg Cys Thr
1 5 10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Dht
<220> FEATURE:
<223> OTHER INFORMATION: C-term COOH

<400> SEQUENCE: 19

Ile Cys Val Trp Gln Asp Trp Gly Ala His Arg Cys Thr
1 5 10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term COOH

<400> SEQUENCE: 20

Ile Cys Val Phe Gln Asp Trp Gly Ala His Arg Cys Thr
1 5 10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic peptide -continued
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term CONH2

<400> SEQUENCE: 21

Ile Cys Val Phe Gln Asp Trp Gly Ala His Arg Cys Thr
1 5 10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term COOH

<400> SEQUENCE: 22

Ile Cys Val Xaa Gln Asp Trp Gly Ala His Arg Cys Thr
1 5 10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term CONH2

<400> SEQUENCE: 23

Ile Cys Val Xaa Gln Asp Trp Gly Ala His Arg Cys Thr
1 5 10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: 2-Abu
<220> FEATURE:
<223> OTHER INFORMATION: C-term CONH2

<400> SEQUENCE: 24

Ile Cys Val Trp Gln Asp Trp Gly Xaa His Arg Cys Thr
1 5 10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term H
<220> FEATURE:
<223> OTHER INFORMATION: C-term COOH

<400> SEQUENCE: 25

Gly Ile Cys Val Trp Gln Asp Trp Gly Ala His Arg Cys Thr Ala Asn
1 5 10 15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<223> OTHER INFORMATION: C-term CONH2

<400> SEQUENCE: 26

Ile Cys Val Trp Gln Asp Trp Gly Ala His Arg Cys Thr
1 5 10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<223> OTHER INFORMATION: C-term CONH2

<400> SEQUENCE: 27

Ile Cys Val Trp Gln Asp Trp Gly Ala His Arg Cys Thr
1 5 10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<223> OTHER INFORMATION: C-term CONH2

<400> SEQUENCE: 28

Ile Cys Val Trp Gln Asp Trp Gly Ala His Arg Cys Thr
1 5 10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 29

Ile Cys Val Trp Gln Asp Trp Gly Ala His Arg Cys Thr
1 5 10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 30

Ile Cys Val Trp Gln Asp Trp Gly Ala His Arg Cys Thr
1 5 10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 31

Ile Cys Val Trp Gln Asp Trp Gly Ala His Arg Cys Thr
1 5 10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 32

Ile Cys Val Trp Gln Asp Trp Gly Ala His Arg Cys Thr
1 5 10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 6f-Trp
<220> FEATURE:
<221> NAME/KEY: MOD_RES
<222> LOCATION: (8)..(8)
<223> OTHER INFORMATION: 6f-Trp
<220> FEATURE:
<223> OTHER INFORMATION: C-term COOH

<400> SEQUENCE: 33

Gly Ile Cys Val Trp Gln Asp Trp Gly Ala His Arg Cys Thr Asn
1 5 10 15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-formyl-Trp
<220> FEATURE:
<223> OTHER INFORMATION: C-term CONH2

<400> SEQUENCE: 34

Ile Cys Val Trp Gln Asp Trp Gly Ala His Arg Cys Thr
1 5 10

<210> SEQ ID NO 35
<211> LENGTH: 13
<212> TYPE: PRT

-continued

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methoxy-Trp
<220> FEATURE:
<223> OTHER INFORMATION: C-term CONH2

<400> SEQUENCE: 35

Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 5f-Trp
<220> FEATURE:
<221> NAME/KEY: MOD_RES
<222> LOCATION: (8)..(8)
<223> OTHER INFORMATION: 5f-Trp
<220> FEATURE:
<223> OTHER INFORMATION: C-term COOH

<400> SEQUENCE: 36

Gly Ile Cys Val Trp Gln Asp Trp Gly Ala His Arg Cys Thr Asn
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp

<400> SEQUENCE: 37

Ile Cys Val Trp Gln Asp Trp Gly Ala His Arg Cys Thr
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Maleimide-(CH2)5-C(=O)
<220> FEATURE:
<221> NAME/KEY: MISC_FEATURE
<222> LOCATION: (2)..(12)

-continued

<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 38

Ile Cys Val Trp Gln Asp Trp Gly Ala His Arg Cys Thr
1 5 10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term (C=O)-(CH2)5-maleimide

<400> SEQUENCE: 39

Ile Cys Val Trp Gln Asp Trp Gly Ala His Arg Cys Thr
1 5 10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Maleimide-(CH2)2-C(=O)-NH-CH2CH2OCH2CH2O
CH2CH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 40

Ile Cys Val Trp Gln Asp Trp Gly Ala His Arg Cys Thr
1 5 10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Maleimide-(CH2)2-C(=O)-NH-
CH2CH2OCH2CH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 41

Ile Cys Val Trp Gln Asp Trp Gly Ala His Arg Cys Thr
1 5 10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Maleimide-(CH2)3-C(=O)-NH-CH2CH2OCH2CH2 OCH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 42

Ile Cys Val Trp Gln Asp Trp Gly Ala His Arg Cys Thr
1 5 10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Maleimide-(CH2)5-C(=O)-NH-CH2CH2OCH2CH2 OCH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 43

Ile Cys Val Trp Gln Asp Trp Gly Ala His Arg Cys Thr
1 5 10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Maleimide-(CH2)4-C(=O)-NH-CH2CH2OCH2CH2 OCH2CH2C(=O)

-continued

<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 44

Ile Cys Val Trp Gln Asp Trp Gly Ala His Arg Cys Thr
1 5 10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Maleimide-(CH2)2-C(=O)-NH-CH2CH2OCH2CH2
OCH2CH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 45

Ile Cys Val Trp Gln Asp Trp Gly Ala His Arg Cys Thr
1 5 10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Maleimide-(CH2)5-C(=O)-NH-CH2CH2OCH2CH2
OCH2C(=O)
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 46

Ile Cys Val Trp Gln Asp Trp Gly Ala His Arg Cys Thr
1 5 10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
peptide
<220> FEATURE:

-continued

<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 47

Ile Cys Val Trp Gln Asp Trp Gly Ala His Arg Cys Thr Lys
1 5 10

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 48

Ile Cys Val Trp Gln Asp Trp Gly Ala His Arg Cys Thr Gly Gly Gly
1 5 10 15

Gly Gly Lys

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term NH2(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 49

Ile Cys Val Trp Gln Asp Trp Gly Ala His Arg Cys Thr
1 5 10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term NH2(CH2CH2O)2CH2C(=O)
<220> FEATURE:
<221> NAME/KEY: MOD_RES

```
<222> LOCATION: (4)..(4)
<223> OTHER INFORMATION: (1Me)Trp
<220> FEATURE:
<223> OTHER INFORMATION: C-term NH2

<400> SEQUENCE: 50

Ile Cys Val Trp Gln Asp Trp Gly Ala His Arg Cys Thr
1               5                   10


<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys
<220> FEATURE:
<223> OTHER INFORMATION: C-term NH2

<400> SEQUENCE: 51

Ile Cys Val Trp Gln Asp Trp Gly Ala His Arg Cys Thr Lys
1               5                   10


<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 52

Ile Cys Val Trp Gln Asp Trp Gly Ala His Arg Cys Thr Lys
1               5                   10


<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-(C(=O)-(CH2)5-Mal)
<220> FEATURE:
<223> OTHER INFORMATION: C-term NH2

<400> SEQUENCE: 53

Ile Cys Val Trp Gln Asp Trp Gly Ala His Arg Cys Thr Gly Gly Gly
1               5                   10                  15

Gly Gly Lys

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)-NH(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 54

Ile Cys Val Trp Gln Asp Trp Gly Ala His Arg Cys Thr
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mal-(CH2)5-(C(=O)NH(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 55

Ile Cys Val Trp Gln Asp Trp Gly Ala His Arg Cys Thr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)5-Mal)
<220> FEATURE:
<223> OTHER INFORMATION: C-term NH2

<400> SEQUENCE: 56

Ile Cys Val Trp Gln Asp Trp Gly Ala His Arg Cys Thr Lys
1 5 10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-CH2(OCH2CH2)2NH(C(=O)-(CH2)5-Mal)
<220> FEATURE:
<223> OTHER INFORMATION: C-term NH2

<400> SEQUENCE: 57

Ile Cys Val Trp Gln Asp Trp Gly Ala His Arg Cys Thr Lys
1 5 10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term (CH2CH2O)nC(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 58

Ile Cys Val Trp Gln Asp Trp Gly Ala His Arg Cys Thr
1 5 10

<210> SEQ ID NO 59
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-C(=O)-(CH2CH2O)n
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 59

Ile Cys Val Trp Gln Asp Trp Gly Ala His Arg Cys Thr Lys
1               5                   10


<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 60

Ile Cys Val Trp Gln Asp Trp Gly Ala His Arg Cys Thr Lys
1               5                   10


<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
```

<220> FEATURE:
<221> NAME/KEY: MOD_RES
<222> LOCATION: (19)..(19)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 61

Ile Cys Val Trp Gln Asp Trp Gly Ala His Arg Cys Thr Gly Gly Gly
1 5 10 15

Gly Gly Lys

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: MISC_FEATURE
<222> LOCATION: (8)..(18)
<223> OTHER INFORMATION: Disulfide bond
<220> FEATURE:
<221> NAME/KEY: MOD_RES
<222> LOCATION: (10)..(10)
<223> OTHER INFORMATION: (1Me)Trp
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 62

Lys Gly Gly Gly Gly Gly Ile Cys Val Trp Gln Asp Trp Gly Ala His
1 5 10 15

Arg Cys Thr

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: (1Me)Trp
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 63

Lys Ile Cys Val Trp Gln Asp Trp Gly Ala His Arg Cys Thr
1 5 10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2CH2O)n-R)
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 64

Ile Cys Val Trp Gln Asp Trp Gly Ala His Arg Cys Thr Lys
1 5 10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-(CH2CH2O)n-R)
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 65

Ile Cys Val Trp Gln Asp Trp Gly Ala His Arg Cys Thr Lys
1 5 10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-C(=O)-(CH2CH2O)n-R)
<220> FEATURE:
<223> OTHER INFORMATION: C-term NH2
<220> FEATURE:
<223> OTHER INFORMATION: See specification as filed for detailed description of substitutions and preferred embodiments

<400> SEQUENCE: 66

Ile Cys Val Trp Gln Asp Trp Gly Ala His Arg Cys Thr Lys
1 5 10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-C(=O)-(CH2)j(CH2CH2O)n-R)
<220> FEATURE:
<223> OTHER INFORMATION: C-term NH2

<400> SEQUENCE: 67

Ile Cys Val Trp Gln Asp Trp Gly Ala His Arg Cys Thr Lys
1 5 10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MISC_FEATURE
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:

```
<221> NAME/KEY: MISC_FEATURE
<222> LOCATION: (13)..(14)
<223> OTHER INFORMATION: Residues at these positions are linked by an
      AEEAc moiety
<220> FEATURE:
<221> NAME/KEY: MOD_RES
<222> LOCATION: (14)..(14)
<223> OTHER INFORMATION: Lys-(C(=O)-(CH2)5-Mal)
<220> FEATURE:
<223> OTHER INFORMATION: C-term NH2

<400> SEQUENCE: 68

Ile Cys Val Trp Gln Asp Trp Gly Ala His Arg Cys Thr Lys
1               5                   10


<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Any independently selected amino acid or amino
      acid analog
<220> FEATURE:
<221> NAME/KEY: MOD_RES
<222> LOCATION: (5)..(5)
<223> OTHER INFORMATION: Trp or analog of Trp
<220> FEATURE:
<221> NAME/KEY: MOD_RES
<222> LOCATION: (8)..(8)
<223> OTHER INFORMATION: Trp or analog of Trp
<220> FEATURE:
<221> NAME/KEY: MOD_RES
<222> LOCATION: (10)..(14)
<223> OTHER INFORMATION: Any independently selected amino acid or amino
      acid analog
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 69

Xaa Xaa Xaa Xaa Xaa Gln Asp Xaa Gly Xaa Xaa Xaa Xaa Xaa Xaa
1               5                   10                  15


<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: MISC_FEATURE
```

<222> LOCATION: (2)..(3)
<223> OTHER INFORMATION: This region may encompass 1 to 2 residues, wherein some positions may be absent
<220> FEATURE:
<221> NAME/KEY: MISC_FEATURE
<222> LOCATION: (4)..(14)
<223> OTHER INFORMATION: Disulfide bond
<220> FEATURE:
<221> NAME/KEY: MOD_RES
<222> LOCATION: (6)..(6)
<223> OTHER INFORMATION: Independently selected from Trp or analogs of Trp
<220> FEATURE:
<221> NAME/KEY: MOD_RES
<222> LOCATION: (9)..(9)
<223> OTHER INFORMATION: Independently selected from Trp or analogs of Trp
<220> FEATURE:
<221> NAME/KEY: MOD_RES
<222> LOCATION: (11)..(11)
<223> OTHER INFORMATION: His, Ala or an analog of Ala, Phe, Trp or an analog of Trp
<220> FEATURE:
<221> NAME/KEY: MOD_RES
<222> LOCATION: (15)..(17)
<223> OTHER INFORMATION: L-Thr, D-Thr, Ile, Val, Gly, a dipeptide selected from Thr-Ala or Thr-Asn, or a tripeptide comprising Thr-Ala-Asn, wherein a C-term -OH of any of the L-Thr, D-Thr, Ile, Val, Gly, Ala or Asn is optionally replaced by a second blocking moiety
<220> FEATURE:
<221> NAME/KEY: MISC_FEATURE
<222> LOCATION: (15)..(17)
<223> OTHER INFORMATION: This region may encompass 1 to 3 residues, wherein some positions may be absent
<220> FEATURE:
<221> NAME/KEY: MOD_RES
<222> LOCATION: (18)..(18)
<223> OTHER INFORMATION: Any amino acid
<220> FEATURE:
<223> OTHER INFORMATION: See specification as filed for detailed description of substitutions and preferred embodiments

<400> SEQUENCE: 70

```
Xaa Xaa Xaa Cys Val Xaa Gln Asp Xaa Gly Xaa His Arg Cys Xaa Xaa
1               5                   10                  15

Xaa Xaa
```

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Ile or Gly
<220> FEATURE:
<221> NAME/KEY: MOD_RES
<222> LOCATION: (3)..(3)
<223> OTHER INFORMATION: Ile or Cys
<220> FEATURE:
<221> NAME/KEY: MOD_RES
<222> LOCATION: (4)..(4)
<223> OTHER INFORMATION: Val or Cys
<220> FEATURE:
<221> NAME/KEY: MOD_RES
<222> LOCATION: (5)..(5)
<223> OTHER INFORMATION: Val, Tyr, Trp, 2-Nal, 1-Nal, 2-Igl, Dht, Bpa, Bta, 5f-Trp, 5-methyl-Trp, 1-methyl-Trp, 1-formyl-Trp or

```
      1-methyoxy-Trp
<220> FEATURE:
<221> NAME/KEY: MOD_RES
<222> LOCATION: (6)..(6)
<223> OTHER INFORMATION: Gln, Trp, 6f-Trp or 5f-Trp
<220> FEATURE:
<221> NAME/KEY: MOD_RES
<222> LOCATION: (7)..(7)
<223> OTHER INFORMATION: Asp or Gln
<220> FEATURE:
<221> NAME/KEY: MOD_RES
<222> LOCATION: (8)..(8)
<223> OTHER INFORMATION: Trp, Asp or 5f-Trp
<220> FEATURE:
<221> NAME/KEY: MOD_RES
<222> LOCATION: (9)..(9)
<223> OTHER INFORMATION: Gly, Trp, 6f-Trp or 5f-Trp
<220> FEATURE:
<221> NAME/KEY: MOD_RES
<222> LOCATION: (10)..(10)
<223> OTHER INFORMATION: His, Ala, 2-Abu or Gly
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Arg or His
<220> FEATURE:
<221> NAME/KEY: MOD_RES
<222> LOCATION: (13)..(13)
<223> OTHER INFORMATION: Cys or Arg
<220> FEATURE:
<221> NAME/KEY: MOD_RES
<222> LOCATION: (14)..(14)
<223> OTHER INFORMATION: Thr, D-Thr or Cys
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
      description of substitutions and preferred embodiments

<400> SEQUENCE: 71

Xaa Xaa Xaa Xaa Xaa Xaa Xaa Xaa Xaa Xaa Xaa Xaa Xaa Xaa Xaa
1               5                   10                  15


<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MISC_FEATURE
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
```

<221> NAME/KEY: MOD_RES
<222> LOCATION: (15)..(15)
<223> OTHER INFORMATION: Any amino acid
<220> FEATURE:
<223> OTHER INFORMATION: See specification as filed for detailed
description of substitutions and preferred embodiments

<400> SEQUENCE: 72

Xaa Ile Cys Val Trp Gln Asp Trp Gly Ala His Arg Cys Ile Xaa
1 5 10 15

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Trp Glu Ser Asn Gly Gln Pro Glu Asn Asn
1 5 10

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Lys Thr Ile Ser Lys Ala Lys Gly Gln Pro Arg Glu Pro Gln Val Tyr
1 5 10 15

Thr

<210> SEQ ID NO 75
<211> LENGTH: 5148
<212> TYPE: RNA
<213> ORGANISM: Homo sapiens

<400> SEQUENCE: 75
agauaaaaag ccagcuccag caggcgcugc ucacuccucc ccauccucuc ccucugucce 60 ucugucccuc ugacccugca cugucccagc accaugggac ccaccucagg ucccagccug 120
cugcuccugc uacuaaccca ccucccccug gcucugggga gucccaugua cucuaucauc 180
acccccaaca ucuugcggcu ggagagcgag gagaccaugg ugcuggaggc ccacgacgcg 240
caaggggaug uuccagucac uguuacuguc cacgacuucc caggcaaaaa acuagugcug 300
uccagugaga agacugugcu gaccccugcc accaaccaca ugggcaacgu caccuucacg 360
aucccagcca acagggaguu caagucagaa aaggggcgca acaaguucgu gaccgugcag 420
gccaccuucg ggacccaagu gguggagaag guggugcugg ucagccugca gagcggguac 480
cucuucaucc agacagacaa gaccaucuac accccuggcu ccacaguucu cuaucggauc 540
uucaccguca accacaagcu gcuacccgug ggccggacgg ucauggucaa cauugagaac 600
ccggaaggca ucccggucaa gcaggacucc uugucuucuc agaaccagcu uggcgucuug 660
cccuugucuu gggacauucc ggaacucguc aacaugggcc aguggaagau ccgagccuac 720
uaugaaaacu caccacagca ggucuucucc acugaguuug aggugaagga guacgugcug 780
cccaguuucg aggucauagu ggagccuaca gagaaauucu acuacaucua uaacgagaag 840
ggccuggagg ucaccaucac cgccagguuc cucuacggga agaaagugga gggaacugcc 900

-continued

```
uuugucaucu ucgggaucca ggauggcgaa cagaggauuu cccugccuga aucccucaag    960
cgcauuccga uugaggaugg cucgggggag guugugcuga gccggaaggu acugcuggac   1020
ggggugcaga acccccgagc agaagaccug gugggggaagu cuuuguacgu gucugccacc   1080
gucaucuugc acucaggcag ugacauggug caggcagagc gcagcgggau ccccaucgug   1140
accucucccu accagaucca cuucaccaag acacccaagu acuucaaacc aggaaugccc   1200
uuugaccuca ugguguucgu gacgaacccu gauggcucuc cagccuaccg aguccccgug   1260
gcaguccagg gcgaggacac ugugcagucu cuaacccagg gagauggcgu ggccaaacuc   1320
agcaucaaca cacaccccag ccagaagccc uugagcauca cggugcgcac gaagaagcag   1380
gagcucucgg aggcagagca ggcuaccagg accaugcagg cucugcccua cagcaccgug   1440
ggcaacucca acaauuaccu gcaucucuca gugcuacgua cagagcucag acccggggag   1500
acccucaacg ucaacuuccu ccugcgaaug gaccgcgccc acgaggccaa gauccgcuac   1560
uacaccuacc ugaucaugaa caagggcagg cuguugaagg cgggacgcca ggugcgagag   1620
cccggccagg accugguggu gcugccccug uccaucacca ccgacuucau cccuuccuuc   1680
cgccuggugg cguacuacac gcugaucggu gccagcggcc agagggaggu gguggccgac   1740
uccgugugggg uggacgucaa ggacuccugc gugggcucgc ugguggguaaa aagcggccag   1800
ucagaagacc ggcagccugu accugggcag cagaugaccc ugaagauaga gggugaccac   1860
ggggcccggg ugguacuggu ggccguggac aagggcgugu ucgugcugaa uaagaagaac   1920
aaacugacgc agaguaagau cugggacgug guggagaagg cagacaucgg cugcaccccg   1980
ggcagugggga aggauuacgc cggugucuuc uccgacgcag ggcugaccuu cacgagcagc   2040
aguggccagc agaccgccca gagggcagaa cuucagugcc cgcagccagc cgcccgccga   2100
cgccguuccg ugcagcucac ggagaagcga auggacaaag ucggcaagua ccccaaggag   2160
cugcgcaagu gcugcgagga cggcaugcgg gagaacccca ugagguucuc gugccagcgc   2220
cggacccguu ucaucucccu gggcgaggcg ugcaagaagg ucuuccugga cugcugcaac   2280
uacaucacag agcugcggcg gcagcacgcg cgggccagcc accugggccu ggccaggagu   2340
aaccuggaug aggacaucau ugcagaagag aacaucguuu cccgaaguga guucccagag   2400
agcuggcugu ggaacguuga ggacuugaaa gagccaccga aaaauggaau cucuacgaag   2460
cucaugaaua uauuuuugaa agacuccauc accacguggg agauucuggc ugugagcaug   2520
ucggacaaga aagggaucug uguggcagac ccccuucgagg ucacaguaau gcaggacuuc   2580
uucaucgacc ugcggcuacc cuacucuguu guucgaaacg agcaggugga aauccgagcc   2640
guucucuaca auuaccggca gaaccaagag cucaaggauga ggguggaacu acuccacaau   2700
ccagccuucu gcagccuggc caccaccaag aggcgucacc agcagaccgu aaccaucccc   2760
cccaaguccu cguuguccgu uccauauguc aucgugccgc uaaagaccgg ccugcaggaa   2820
guggaaguca aggcugcugu cuaccaucau uucaucagug acggugucag gaagucccug   2880
aaggucgugc cggaaggaau cagaaugaac aaaacugugg cuguucgcac ccuggaucca   2940
gaacgccugg gccgugaagg agugcagaaa gaggacaucc caccugcaga ccucagugac   3000
```

-continued

```
caaguc ccgg acaccgaguc ugagaccaga auucuccugc aagggacccc aguggcccag   3060
augacagagg augccgucga cgcggaacgg cugaagcacc ucauugugac ccccucgggc   3120
ugcggggaac agaacaugau cggcaugacg cccacgguca ucgcugugca uuaccuggau   3180
gaaacggagc agugggagaa guucggccua gagaagcggc agggggccuu ggagcucauc   3240
aagaaggggu acacccagca gcuggccuuc agacaaccca gcucugccuu ugcggccuuc   3300
gugaaacggg cacccagcac cuggcugacc gccuacgugg ucaaggucuu cucucuggcu   3360
gucaaccuca ucgccaucga cucccaaguc cucugcgggg cuguuaaaug gcugauccug   3420
gagaagcaga agcccgacgg ggucuuccag gaggaugcgc ccgugauaca ccaagaaaug   3480
auugguggau uacggaacaa caacgagaaa gacauggccc ucacggccuu uguucucauc   3540
ucgcugcagg aggcuaaaga uauuugcgag gagcagguca acagccugcc aggcagcauc   3600
acuaaagcag gagacuuccu ugaagccaac uacaugaacc uacagagauc cuacacugug   3660
gccauugcug gcuaugcucu ggcccagaug ggcaggcuga aggggccucu ucuuaacaaa   3720
uuucugacca cagccaaaga uaagaaccgc ugggaggacc cugguaagca gcucuacaac   3780
guggaggcca cauccuaugc ccucuuggcc cuacugcagc uaaaagacuu ugacuuugug   3840
ccucccgucg ugcguuggcu caaugaacag agauacuacg gugguggcua uggcucuacc   3900
caggccaccu ucaugguguu ccaagccuug gcucaauacc aaaaggacgc cccugaccac   3960
caggaacuga accuugaugu gucccuccaa cugcccagcc gcagcuccaa gaucacccac   4020
cguauccacu gggaaucugc cagccuccug cgaucagaag agaccaagga aaaugagggu   4080
uucacaguca cagcugaagg aaaaggccaa ggcaccuugu cgguggugac aauguaccau   4140
gcuaaggcca aagaucaacu caccuguaau aaauucgacc ucaaggucac cauaaaacca   4200
gcaccggaaa cagaaaagag gccucaggau gccaagaaca cuaugauccu ugagaucugu   4260
accagguacc ggggagacca ggaugccacu augucuauau uggacauauc caugaugacu   4320
ggcuuugcuc cagacacaga ugaccugaag cagcuggcca augguguuga cagauacauc   4380
uccaaguaug agcuggacaa agccuucucc gauaggaaca cccucaucau cuaccuggac   4440
aaggucucac acucugagga ugacugucua gcuuucaaag uucaccaaua cuuuaaugua   4500
gagcuuaucc agccuggagc agucaagguc uacgccuauu acaaccugga ggaaagcugu   4560
acccgguucu accauccgga aaaggaggau ggaaagcuga acaagcucug ccgugaugaa   4620
cugugccgcu gugcugagga gaauugcuuc auacaaaagu cggaugacaa ggucacccug   4680
gaagaacggc uggacaaggc cugugagcca ggaguggacu auguguacaa gacccgacug   4740
gucaagguuc agcuguccaa ugacuuugac gaguacauca uggccauuga gcagaccauc   4800
aagucaggcu cggaugaggu gcagguugga cagcagcgca cguucaucag ccccaucaag   4860
ugcagagaag cccugaagcu ggaggagaag aaacacuacc ucaugugggg ucucuccucc   4920
gauuucuggg gagagaagcc caaccucagc uacaucaucg ggaaggacac uuggguggag   4980
cacuggcccg aggaggacga augccaagac gaagagaacc agaaacaaug ccaggaccuc   5040
ggcgccuuca ccgagagcau gguugucuuu gggugcccca acugaccaca cccccauucc   5100
cccacuccag auaaagcuuc aguuauaucu caaaaaaaaa aaaaaaaa                5148
```

VIRAL VECTOR THERAPY

CROSS REFERENCE TO RELATED APPLICATIONS

This application is the National Stage of International Application No. PCT/US20/40741, filed Jul. 2, 2020, which claims the benefit of U.S. Provisional Application No. 62/871,058, filed Jul. 5, 2019, U.S. Provisional Application No. 62/871,700, filed Jul. 8, 2019, U.S. Provisional Application No. 62/875,925, filed Jul. 18, 2019, and U.S. Provisional Application No. 62/935,569, filed Nov. 14, 2019, the contents of each of which are hereby incorporated by reference herein in their entirety.

SEQUENCE LISTING

In accordance with 37 CFR § 1.52 (e) (5), a Sequence Listing in the form of a text file (entitled "Sequence Listing.txt", created on Aug. 12, 2020 and having a size of 46 KB) is hereby incorporated by reference in its entirety.

BACKGROUND

Viral vectors are promising therapeutics for a variety of applications such as gene therapy, gene editing, gene expression modulation and exon skipping. Efficacy of such viral vector therapeutics can be limited by, e.g., immune responses against the viral vector. Thus, there remains a need for methods and compositions to increase efficacy of viral vector therapeutics.

SUMMARY

In one aspect, the disclosure features a method of improving efficacy of a gene therapy in a subject receiving or who has received the gene therapy, the method comprising administering a complement inhibitor to the subject, thereby improving efficacy of the gene therapy. In some embodiments, the efficacy of the gene therapy is improved in the subject over a specified time period relative to a control subject receiving or who has received the gene therapy and is not administered the complement inhibitor.

In some embodiments, the gene therapy comprises a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector, or any variant thereof.

In some embodiments, the viral vector is retroviral vector. In some embodiments, the retroviral vector is a lentiviral vector. In some embodiments, the lentivirus is a human immunodeficiency viruses (HIV-1 and HIV-2), simian immunodeficiency virus (SIV), feline immunodeficiency virus (FIV), equine infections anemia (EIA), or a visna virus.

In some embodiments, the viral vector comprises a transgene. In some embodiments, the transgene encodes a therapeutic protein, enzyme, hormone, blood coagulation factor, cytokine, or growth factor. In some embodiments, the gene therapy is for the treatment of a blood disorder, retinal disease, autoimmune disease, a muscle disorder, a neurological disorder, or cancer.

In some embodiments, the complement inhibitor decreases an immune response (e.g., an antibody, B cell, and/or T cell immune response) against the gene therapy, relative to a control (e.g., a control subject receiving the gene therapy and not administered the complement inhibitor). In some embodiments, the efficacy of the gene therapy is increased at about 1 week, 2 weeks, 4 weeks, 2 months, 3 months, 6 months, 1 year, or longer, relative to a control (e.g., a control subject receiving the gene therapy and not administered the complement inhibitor).

In some embodiments, transduction of the viral vector is improved, relative to a control (e.g., a control subject receiving the gene therapy and not administered the complement inhibitor). In some embodiments, transduction is assessed by measuring level of transgene expression. In some embodiments, complement-mediated clearance of the viral vector is decreased relative to a control (e.g., a control subject receiving the gene therapy and not administered the complement inhibitor).

In some embodiments, the complement inhibitor comprises a C3 inhibitor. In some embodiments, the C3 inhibitor decreases the level and/or activity of a C3 transcript or C3 protein.

In another aspect, the disclosure features a method of reducing complement activation in a subject who has received or is receiving gene therapy (e.g., viral vector therapy), the method comprising: administering a gene therapy (e.g., viral vector therapy) to the subject; and administering a complement inhibitor to the subject, thereby reducing complement activation in the subject.

In some embodiments, the complement inhibitor is a C3 inhibitor. In some embodiments, level of C3 expression and/or activity is reduced by more than 10%, 20%, 30%, 40%, 50%, or 100%, relative to measured level of C3 expression and/or activity in a control subject (e.g., a control subject receiving the gene therapy and not administered the complement inhibitor or a control subject receiving the gene therapy and before being administered the C3 inhibitor).

In some embodiments, the gene therapy comprises a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector, or any variant thereof. In some embodiments, the viral vector comprises a transgene. In some embodiments, the transgene encodes a therapeutic protein, enzyme, hormone, blood coagulation factor, cytokine, or growth factor. In some embodiments, the gene therapy is for the treatment of a blood disorder, retinal disease, autoimmune disease, a muscle disorder, a neurological disorder, or cancer.

In some embodiments, the complement inhibitor decreases an immune response (e.g., an antibody, B cell, and/or T cell immune response) against the gene therapy, relative to a control (e.g., a control subject receiving the gene therapy and not administered the complement inhibitor). In some embodiments, the efficacy of the gene therapy is increased at about 1 week, 2 weeks, 4 weeks, 2 months, 3 months, 6 months, 1 year, or longer, relative to a control (e.g., a control subject receiving the gene therapy and not administered the complement inhibitor). In some embodiments, transduction of the viral vector is improved, relative to a control (e.g., a control subject receiving the gene therapy and not administered the complement inhibitor). In some embodiments, transduction is assessed by measuring level of transgene expression. In some embodiments, complement-mediated clearance of the viral vector is decreased relative to a control (e.g., a control subject receiving the gene therapy and not administered the complement inhibitor).

In another aspect, the disclosure features a method of increasing transduction of a viral vector comprising a transgene in a subject receiving gene therapy, the method comprising: administering a complement inhibitor (e.g., a C3 inhibitor) to the subject, wherein expression of the transgene in the subject is increased relative to a control subject receiving the gene therapy but not administered the complement inhibitor. In some embodiments, expression of the transgene in the subject at, e.g., 1 week, 2 weeks, 3 weeks, 4 weeks, 6 weeks, 8 weeks, 3 months, 6 months, or longer, is at least 10%, 20%, 30%, 40%, 50%, 60%, 70%, 80%, 90%, 100%, 125%, 150%, 175%, 200%, or more, higher relative to a corresponding expression level of the transgene in a control subject (e.g., a control subject receiving the gene therapy and not administered the complement inhibitor). In some embodiments, the expression level of the transgene in the subject is more stable over a period of e.g. 1 week, 2 weeks, 3 weeks, 4 weeks, 6 weeks, 8 weeks, 3 months, 6 months, or longer, relative to a corresponding expression level of the transgene in a control subject (e.g., a control subject receiving the gene therapy and not administered the complement inhibitor).

In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector, or any variant thereof.

In some embodiments, the transgene encodes a therapeutic protein, enzyme, hormone, blood coagulation factor, cytokine, or growth factor. In some embodiments, the gene therapy is for the treatment of a blood disorder, retinal disease, autoimmune disease, a muscle disorder, a neurological disorder, or cancer.

In another aspect, the disclosure features a method of improving efficacy of a gene therapy in a subject receiving or who has received the gene therapy, the method comprising: a) detecting a level of complement activity in a serum sample of the subject; and b) if the level of complement activity is increased relative to a control, administering to the subject a complement inhibitor (e.g., a C3 inhibitor), wherein the complement inhibitor inhibits complement activation in the subject. In some embodiments, detecting the level of serum complement activity is measured using an alternative pathway assay, a classical pathway assay, or both.

In some embodiments, the method further comprising administering the gene therapy to the subject. In some embodiments, the gene therapy comprises a viral vector. In some embodiments, the viral vector is an adeno-associated viral (AAV) vector. In some embodiments, the AAV vector is an AAV1, AAV2, AAV3, AAV4, AAV5, AAV6, AAV7, AAV8, AAV9, AAV10, or AAV11 vector, or any variant thereof.

In some embodiments, the viral vector comprises a transgene. In some embodiments, the transgene encodes a therapeutic protein, enzyme, hormone, blood coagulation factor, cytokine, or growth factor. In some embodiments, the gene therapy is for the treatment of a blood disorder, retinal disease, autoimmune disease, a muscle disorder, a neurological disorder, or cancer.

In any of the aspects described herein, the C3 inhibitor can comprise a compstatin analog, an anti-C3 antibody, a mammalian complement regulatory protein (CR1, DAF, MCP, CFH, or CFI), an enzyme that degrades C3 or C3b, a C1 inhibitor (C1-INH), a soluble form of complement receptor 1 (sCR1), TP10 or TP20, mini-factor H, Efb protein or complement inhibitor (SCIN).

In some embodiments, the compstatin analog comprises a long-acting compstatin analog (LACA), a compstatin mimetic, or a targeted compstatin analog. In some embodiments, the compstatin analog comprises a clearance reducing moiety (CRM) and at least one compstatin analog moiety. In some embodiments, the compstatin analog comprises a CRM having at least two compstatin analog moieties attached thereto.

In some embodiments, the CRM comprises a PEG. In some embodiments, the CRM has an average molecular weight of between about 10 kD and about 50 kD, e.g., between about 35 kD and about 45 kD, e.g., about 40 kD.

In some embodiments, the compstatin analog comprises a linear polymer having a compstatin analog moiety attached to each end.

In some embodiments, each compstatin analog moiety comprises a cyclic peptide that comprises the amino acid sequence of one of SEQ ID NOs: 3-36, 37, 69, 70, 71, and 72.

In some embodiments, the compstatin analog comprises one or more clearance-reducing moieties attached to one or more compstatin analog moieties, wherein: each compstatin analog moiety comprises a cyclic peptide having an amino acid sequence as set forth in any of SEQ ID NOs: 3-36, extended by one or more terminal amino acids at the N-terminus, C-terminus, or both, wherein one or more of the amino acids has a side chain comprising a primary or secondary amine and is separated from the cyclic peptide by a rigid or flexible spacer optionally comprising an oligo (ethylene glycol) moiety; and each clearance-reducing moiety optionally comprises a polyethylene glycol (PEG), wherein each clearance-reducing moiety is covalently attached via a linking moiety to one or more compstatin analog moieties, and wherein the linking moiety comprises an unsaturated alkyl moiety, a moiety comprising a nonaromatic cyclic ring system, an aromatic moiety, an ether moiety, an amide moiety, an ester moiety, a carbonyl moiety, an imine moiety, a thioether moiety, and/or an amino acid residue.

In some embodiments, each compstatin analog moiety comprises a cyclic peptide extended by one or more amino acids at the N-terminus, C-terminus, or both, wherein the one or more amino acids is separated from the cyclic portion of the peptide by a rigid or flexible spacer that comprises 8-amino-3,6-dioxaoctanoic acid (AEEAc) or 11-amino-3,6,9-trioxaundecanoic acid. In some embodiments, the compstatin analog comprises CA28-2TS-BF.

In any of the aspects described herein, the method can further comprise administering the gene therapy to the subject. In some embodiments, the gene therapy and the complement inhibitor are administered to the subject concurrently or sequentially.

In some embodiments, administering the complement inhibitor comprises subretinal, intradermal, intramuscular, intraperitoneal, intravenous, subcutaneous, intranasal, epidural, oral, sublingual, intracerebral, intrathecal, intravaginal, transdermal, rectal, intravitreal, by inhalation, or topical administration. In some embodiments, the gene therapy is administered by subretinal, intradermal, intramuscular, intraperitoneal, intravenous, subcutaneous, intranasal, epidural, oral, sublingual, intracerebral, intrathecal, intravaginal, transdermal, rectal, intravitreal, by inhalation, or topical administration. In some embodiments, the complement inhibitor and the gene therapy are administered by the same route. In some embodiments, the complement inhibitor and the gene therapy are administered by different routes.

In some embodiments, administering the complement inhibitor comprises administering the complement inhibitor daily, weekly, or monthly when the subject is receiving the gene therapy.

In some embodiments, a subject is treated with one or more additional gene therapy doses and the efficacy is improved in the subject over a specified time period relative to the efficacy in control subject (e.g., a control subject treated with the one or more additional gene therapy doses and was not administered the complement inhibitor).

In some embodiments, the one or more additional gene therapy doses is a gene therapy using a different transgene than the previously administered gene therapy.

In some embodiments, the one or more additional gene therapy doses is a gene therapy using the same transgene used in the previously administered gene therapy.

In some embodiments, the one or more additional gene thereapy doses is a gene thereapy using a viral vector that is the same serotype as the previously administered gene therapy.

In some embodiments, the one or more additional gene therapy doses is a gene thereapy using a viral vector that is a different serotype from the previously administered gene therapy.

DEFINITIONS

Figure 1:
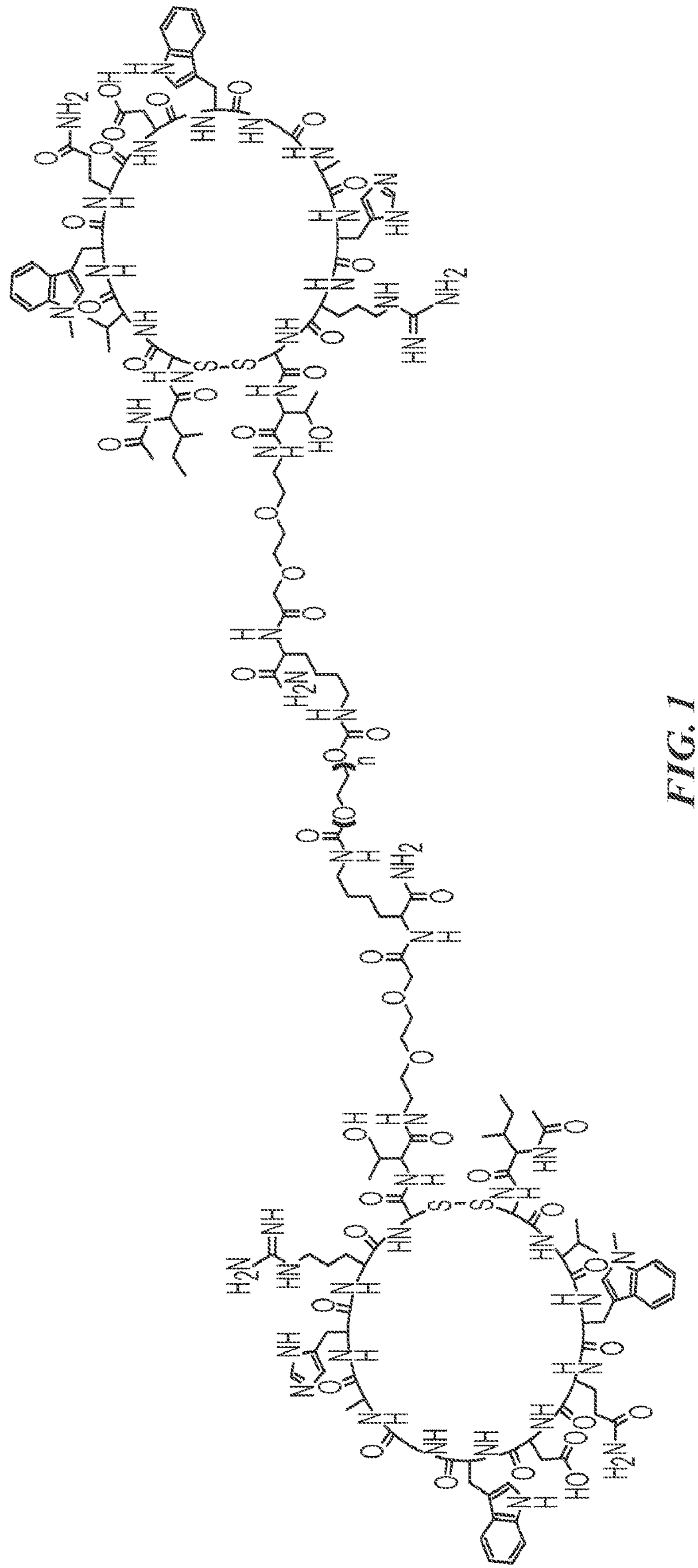
FIG. 1 (assuming a PEG moiety of about 40 kD) shows the structure of CA28-2TS-BF.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Antibody: As used herein, the term "antibody" refers to an immunoglobulin or a derivative thereof containing an immunoglobulin domain capable of binding to an antigen. The antibody can be of any species, e.g., human, rodent, rabbit, goat, chicken, etc. The antibody may be a member of any immunoglobulin class, including any of the human classes: IgG, IgM, IgA, IgD, and IgE, or subclasses thereof such as IgG1, IgG2, etc. In various embodiments of the invention the antibody is a fragment such as an Fab', $F(ab')_2$, scFv (single-chain variable) or other fragment that retains an antigen binding site, or a recombinantly produced scFv fragment, including recombinantly produced fragments. See, e.g., Allen, T., Nature Reviews Cancer, Vol. 2, 750-765, 2002, and references therein. The antibody can be monovalent, bivalent or multivalent. The antibody may be a chimeric or "humanized" antibody in which, for example, a variable domain of rodent origin is fused to a constant domain of human origin, thus retaining the specificity of the rodent antibody. The domain of human origin need not originate directly from a human in the sense that it is first synthesized in a human being. Instead, "human" domains may be generated in rodents whose genome incorporates human immunoglobulin genes. See, e.g., Vaughan, et al., (1998), Nature Biotechnology, 16:535-539. The antibody may be partially or completely humanized. An antibody may be polyclonal or monoclonal, though for purposes of the present invention monoclonal antibodies are generally preferred. Methods for producing antibodies that specifically bind to virtually any molecule of interest are known in the art. For example, monoclonal or polyclonal antibodies can be purified from blood or ascites fluid of an animal that produces the antibody (e.g., following natural exposure to or immunization with the molecule or an antigenic fragment thereof), can be produced using recombinant techniques in cell culture or transgenic organisms, or can be made at least in part by chemical synthesis.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered followed by one or more additional agents. In the separate administration protocol, two or more agents may be administered a few minutes apart, or a few hours apart, a few days apart, or a few weeks apart. In some embodiments, two or more agents may be administered 1-2 weeks apart.

Complement component: As used herein, the terms "complement component" or "complement protein" is a molecule that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, H, and I, and properdin, with factor H being a negative regulator of the pathway. Components of the lectin pathway include, e.g., MBL2, MASP-1, and MASP-2. Complement components also include cell-bound receptors for soluble complement components. Such receptors include, e.g., C5a receptor (C5aR), C3a receptor (C3aR), Complement Receptor 1 (CR1), Complement Receptor 2 (CR2), Complement Receptor 3 (CR3), etc. It will be appreciated that the term "complement component" is not intended to include those molecules and molecular structures that serve as "triggers" for complement activation, e.g., antigen-antibody complexes, foreign structures found on microbial or artificial surfaces, etc.

Complementary DNA: As used herein, a "complementary DNA" or "cDNA" includes recombinant polynucleotides synthesized by reverse transcription of mRNA and from which intervening sequences (introns) have been removed.

Concurrent administration: As used herein, the term "Concurrent administration" with respect to two or more agents, e.g., therapeutic agents, is administration performed using doses and time intervals such that the administered agents are present together within the body, e.g., at one or more sites of action in the body, over a time interval in non-negligible quantities. The time interval can be minutes (e.g., at least 1 minute, 1-30 minutes, 30-60 minutes), hours (e.g., at least 1 hour, 1-2 hours, 2-6 hours, 6-12 hours, 12-24 hours), days (e.g., at least 1 day, 1-2 days, 2-4 days, 4-7 days, etc.), weeks (e.g., at least 1, 2, or 3 weeks, etc.). Accordingly, the agents may, but need not be, administered together as part of a single composition. In addition, the agents may, but need not be, administered essentially simultaneously (e.g., within less than 5 minutes, or within less than 1 minute apart) or within a short time of one another (e.g., less than 1 hour, less than 30 minutes, less than 10 minutes, approximately 5 minutes apart). According to various embodiments of the disclosure, agents administered within such time intervals may be considered to be administered at substantially the same time. In certain embodiments of the disclosure, concurrently administered agents are present at effective concentrations within the body (e.g., in the blood and/or at a site of local complement activation) over the time interval. When administered concurrently, the effective concentration of each of the agents needed to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. The non-negligible concentration of an agent may be, for example, less than approximately 5% of the concentration that would be required to elicit a particular biological response, e.g., a desired biological response.

Host cell: As used herein, the term "host cell" refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO KI, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes.

Identity: As used herein, the term "identity" refers to the overall relatedness between polymeric molecules, e.g., between polypeptide molecules and/or between nucleic acid molecules (e.g., DNA molecules and/or RNA molecules). In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Linked: As used herein, the term "linked", when used with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

Local administration: As used herein, the term "local administration" or "local delivery", in reference to delivery of a complement inhibitor described herein, refers to delivery that does not rely upon transport of the complement inhibitor to its intended target tissue or site via the vascular system. The complement inhibitor described herein may be delivered directly to its intended target tissue or site, or in the vicinity thereof, e.g., in close proximity to the intended target tissue or site. For example, the complement inhibitor may be delivered by injection or implantation of the composition or agent or by injection or implantation of a device containing the composition or agent. Following local administration in the vicinity of a target tissue or site, the complement inhibitor described herein, or one or more components thereof, may diffuse to the intended target tissue or site. It will be understood that once having been locally delivered a fraction of a complement inhibitor described herein (typically only a minor fraction of the administered dose) may enter the vascular system and be transported to another location, including back to its intended target tissue or site. As used herein, the term "local administration" or "local delivery", in reference to delivery of a viral vector described herein, refers to delivery that can rely upon transport of the viral vector to its intended target tissue or site via the vascular system.

Local complement activation: As used herein, the term "local complement activation" refers to complement activation that occurs outside the vascular system.

Operably linked: As used herein, the term "operably linked" refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Recombinant: As used herein, the term "recombinant" is intended to refer to nucleic acids or polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

RNA interference: As used herein, the term "RNA interference" or "RNAi" refers generally to a process in which a double-stranded RNA molecule or a short hairpin RNA molecule reduces or inhibits expression of a nucleic acid sequence with which the double-stranded or short hairpin RNA molecule shares substantial or total homology. Without wishing to be bound by any theory, it is believed that, in nature, the RNAi pathway is initiated by a Type III endonuclease known as Dicer, which cleaves long double-stranded RNA (dsRNA) into double-stranded fragments typically of 21-23 base pairs with 2-base 3' overhangs (although variations in length and overhangs are also contemplated), referred to as "short interfering RNAs" ("siRNAs"). Such siRNAs comprise two single-stranded RNAs (ssRNAs), with an "antisense strand" or "guide strand" that includes a region that is substantially complementary to a target sequence, and a "sense strand" or "passenger strand" that includes a region that is substantially complementary to a region of the antisense strand. Those of ordinary skill in the art will appreciate that a guide strand may be perfectly complementary to a target region of a target RNA or may have less than perfect complementarity to a target region of a target RNA.

Sequential administration: As used herein, the term "sequential administration" of two or more agents refers to administration of two or more agents to a subject such that the agents are not present together in the subject's body, or at a relevant site of activity in the body, at greater than non-negligible concentrations. Administration of the agents may, but need not, alternate. Each agent may be administered multiple times.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Systemic: As used herein, the term "systemic" in reference to complement components, refers to complement proteins that are synthesized by liver hepatocytes and enter the bloodstream, or are synthesized by circulating macrophages or monocytes or other cells and secreted into the bloodstream.

Systemic complement activation: As used herein, the term "systemic complement activation" is complement activation that occurs in the blood, plasma, or serum and/or involves activation of systemic complement proteins at many locations throughout the body, affecting many body tissues, systems, or organs.

Systemic administration: As used herein, the term "systemic administration" and like terms are used herein consistently with their usage in the art to refer to administration of an agent such that the agent becomes widely distributed in the body in significant amounts and has a biological effect, e.g., its desired effect, in the blood and/or reaches its desired site of action via the vascular system. Typical systemic routes of administration include administration by (i) introducing the agent directly into the vascular system or (ii) subcutaneous, oral, pulmonary, or intramuscular administration wherein the agent is absorbed, enters the vascular system, and is carried to one or more desired site(s) of action via the blood.

Target gene: A "target gene", as used herein, refers to a gene whose expression is to be modulated, e.g., inhibited. As used herein, the term "target RNA" refers to an RNA to be degraded or translationally repressed or otherwise inhibited using one or more agents, e.g., one or more miRNAs or siRNAs. A target RNA may also be referred to as a target sequence or target transcript. The RNA may be a primary RNA transcript transcribed from the target gene (e.g., a pre-mRNA) or a processed transcript, e.g., mRNA encoding a polypeptide. As used herein, the term "target portion" or "target region" refers to a contiguous portion of the nucleotide sequence of a target RNA. In some embodiments, a target portion an mRNA is at least long enough to serve as a substrate for RNA interference (RNAi)-mediated cleavage within that portion in the presence of a suitable miRNA or siRNA. A target portion may be from about 8-36 nucleotides in length, e.g., about 10-20 or about 15-30 nucleotides in length. A target portion length may have specific value or subrange within the afore-mentioned ranges. For example, in certain embodiments a target portion may be between about 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent can be an agent that, when administered to a subject, can prevent an undesired side effect, such as an immune response to a viral vector described herein. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. In some embodiments, a therapeutically effective amount of a substance is an amount that is sufficient, when administered to a subject suffering from or susceptible to a disease, disorder, and/or condition, to treat, prevent, and/or delay the onset of an undesired side effect, e.g., an immune response to a viral vector described herein. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or signs of the disease, disorder, and/or condition. In some embodiments, a therapeutically effective amount is administered in a single dose; in some embodiments, multiple unit doses are required to deliver a therapeutically effective amount.

Treating: As used herein, the term "treating" refers to providing treatment, i.e., providing any type of medical or surgical management of a subject. The treatment can be provided in order to reverse, alleviate, inhibit the progression of, prevent or reduce the likelihood of a disease, disorder, or condition, or in order to reverse, alleviate, inhibit or prevent the progression of, prevent or reduce the likelihood of one or more symptoms or manifestations of a disease, disorder or condition. "Prevent" refers to causing a disease, disorder, condition, or symptom or manifestation of such not to occur for at least a period of time in at least some individuals. Treating can include administering an agent to the subject following the development of one or more symptoms or manifestations indicative of a complement-mediated condition, e.g., in order to reverse, alleviate, reduce the severity of, and/or inhibit or prevent the progression of the condition and/or to reverse, alleviate, reduce the severity of, and/or inhibit or one or more symptoms or manifestations of the condition. A composition of the disclosure can be administered to a subject who has developed a complement-mediated disorder or is at increased risk of developing such a disorder relative to a member of the general population. A composition of the disclosure can be administered prophylactically, i.e., before development of any symptom or manifestation of the condition. Typically in this case the subject will be at risk of developing the condition.

Nucleic acid: The term "nucleic acid" includes any nucleotides, analogs thereof, and polymers thereof. The term "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotide linkages"). The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. In some embodiments, the prefix poly-refers to a nucleic acid containing 2 to about 10,000, 2 to about 50,000, or 2 to about 100,000 nucleotide monomer units. In some embodiments, the prefix oligo-refers to a nucleic acid containing 2 to about 200 nucleotide monomer units.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." One of ordinary skill in the art understands that a "viral vector", as described herein, includes viral components in addition to a transgene described herein, e.g., capsid proteins.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

Viral vectors are promising therapeutics for a variety of applications such as gene therapy. Viral vectors can include transgenes that encode, e.g., therapeutic proteins or nucleic acids. Unfortunately, the use of viral vector therapeutics can be unsuccessful due, in part, to immune responses against the viral vector. These immune responses can include antibody, B cell and/or T cell responses and can be specific to viral antigens of the viral vector, such as viral capsid or coat proteins or peptides thereof (see, e.g., Colella et al., Molecular Therapy: Methods & Clinical Development, 8:87-104 (2018)).

The disclosure provides methods and compositions that address such limitations of viral vector therapeutics. In particular, the disclosure provides use of viral vectors in combination with a complement inhibitor (e.g., a complement inhibitor described herein). Without wishing to be bound by theory, it is believed that such combinations can improve viral vector transduction, prevent C3 opsonization of capsids, and/or reduce or prevent immune responses (e.g., antibody, B cell and/or T cell responses). As such, methods of the disclosure can increase efficacy of viral vector therapeutics and/or reduce observed decreases in efficacy of viral vector therapeutics.

I. Gene Therapy/Viral Vectors

Methods and compositions of the disclosure can increase efficacy of any viral vector known in the art or described herein, and the disclosure is not limited to any particular viral vector. For example, and without wishing to be bound by theory, complement inhibitors described herein can be used to protect viral vectors, e.g., during transit from a site of administration to a target cell or tissue; can be used to reduce formation of anti-viral vector neutralizing antibodies (e.g., that may hinder or prevent retreatment with the same viral vector); and/or can prevent or reduce inflammatory reactions that can lead, e.g., to organ damage (e.g., kidney damage). Nonlimiting examples of suitable viral vectors include, for instance, retroviral vectors (e.g., Moloney murine leukemia virus (MMLV), Harvey murine sarcoma virus, murine mammary tumor virus, Rous sarcoma virus), adenoviral vectors, adeno-associated viral (AAV) vectors, SV40-type viral vectors, polyomaviral vectors, Epstein-Barr viral vectors, papilloma viral vectors, herpes viral vectors, vaccinia viral vectors, and polio viral vectors.

Retroviruses are enveloped viruses that belong to the viral family Retroviridae. Once in a host's cell, the virus replicates by using a viral reverse transcriptase enzyme to transcribe its RNA into DNA. The retroviral DNA replicates as part of the host genome, and is referred to as a provirus. A selected nucleic acid can be inserted into a vector and packaged in retroviral particles using techniques known in the art. Protocols for the production of replication-deficient retroviruses are known in the art (see, e.g., Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991)). The recombinant virus can then be isolated and delivered to cells of the subject either in vivo or ex vivo. A number of retroviral systems are known in the art, for example See U.S. Pat. Nos. 5,994,136, 6,165,782, and 6,428,953. Retroviruses include the genus of Alpharetrovirus (e.g., avian leukosis virus), the genus of Betaretrovirus; (e.g., mouse mammary tumor virus) the genus of Deltaretrovirus (e.g., bovine leukemia virus and human T-lymphotropic virus), the genus of Epsilonretrovirus (e.g., Walleye dermal sarcoma virus), and the genus of Lentivirus.

In some embodiments, the retrovirus is a lentivirus of the Retroviridae family. Lentiviral vectors can transduce non-proliferating cells and show low immunogenicity. In some examples, the lentivirus is, but is not limited to, human immunodeficiency viruses (HIV-1 and HIV-2), simian immunodeficiency virus (SIV), feline immunodeficiency virus (FIV), equine infections anemia (EIA), and visna virus. Vectors derived from lentiviruses can achieve significant levels of nucleic acid transfer in vivo.

Herpes simplex virus (HSV)-based viral vectors are also suitable for use as provided herein. Many replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. For a description of HSV-based vectors, see, for example, U.S. Pat. Nos. 5,837,532, 5,846,782, 5,849,572, and 5,804,413, and International Patent Applications WO 91/02788, WO 96/04394, WO 98/15637, and WO 99/06583.

In some embodiments, the vector is an adenovirus vector. Adenoviruses are a large family of viruses containing double stranded DNA. They replicate within the nucleus of a host cell, using the host's cell machinery to synthesize viral RNA, DNA and proteins. Adenoviruses are known in the art to affect both replicating and non-replicating cells, to accommodate large transgenes, and to code for proteins without integrating into the host cell genome. The virus can be made replication-deficient by deleting select genes required for viral replication. The expendable non-replication-essential E3 region is also frequently deleted to allow additional room for a larger DNA insert. The adenovirus on which a viral vector may be based may be from any origin, any subgroup, any subtype, mixture of subtypes, or any serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Non-group C adenoviruses, and even non-human adenoviruses, can be used to prepare replication-deficient adenoviral vectors. Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Applications WO 97/12986 and WO 98/53087. Further examples of adenoviral vectors can be found in U.S. Publication Nos. 20150093831, 20140248305, 20120283318, 20100008889, 20090175897 and 20090088398.

In some embodiments, the viral vector is an adeno-associated virus (AAV) vector. AAV systems are generally well known in the art (see, e.g., Kelleher and Vos, Biotechniques, 17 (6): 1110-17 (1994); Cotten et al., P.N.A.S. U.S.A., 89 (13): 6094-98 (1992); Curiel, Nat Immun, 13 (2-3): 141-64 (1994); Muzyczka, Curr Top Microbiol Immunol, 158:97-129 (1992); and Asokan A, et al., Mol. Ther., 20 (4): 699-708 (2012)). Methods for generating and using AAV vectors are described, for example, in U.S. Pat. Nos. 5,139,941 and 4,797,368. Several AAV serotypes have been characterized, including AAV1, AAV2, AAV3 (e.g., AAV3B), AAV4, AAV5, AAV6, AAV7, AAV8, AAV9, AAV10, and AAV11, as well as variants thereof. In some embodiments, an AAV vector is an AAV2/6, AAV2/8 or AAV2/9 vector (e.g., AAV6, AAV8 or AAV9 serotype having AAV2 ITR). Other AAV vectors are described in, e.g., Sharma et al., Brain Res Bull. 2010 Feb. 15; 81 (2-3): 273. Generally, any AAV serotype may be used to deliver a transgene described herein. However, the serotypes have different tropisms, e.g., they preferentially infect different tissues. In some embodiments, an AAV vector is a self-complementary AAV vector.

In some embodiments, an AAV vector is a naturally occurring AAV. In some embodiments, an AAV vector is a modified AAV (i.e., a variant of a naturally occurring AAV). In some embodiments, a modified AAV vector may be generated by any known vector engineering method. In some embodiments, an AAV vector may be generated by directed evolution, e.g., by DNA shuffling, peptide insertion, or random mutagenesis, in order to introduce modifications into the AAV sequence to improve one or more properties for gene therapy, e.g., to avoid or lessen an immune response or recognition by neutralizing antibodies, and/or for more efficient and/or targeted transduction (Asuri et al., *Molecular Therapy* 20.2 (2012): 329-338). Methods of using directed evolution to engineer an AAV vector can be found, e.g., in U.S. Pat. No. 8,632,764. In some embodiments the modified AAV is modified to include a specific tropism.

The AAV sequences of an AAV vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. In some embodiments, substantially the entire sequences encoding the ITRs are used in an AAV vector, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of an AAV vector of the present disclosure is a "cis-acting" plasmid containing a transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, an AAV vector may be a dual or triple AAV vector, e.g., for the delivery of large transgenes (e.g., transgenes of greater than approximately 5 kb). In some embodiments, a dual AAV vector may include two separate AAV vectors, each including a fragment of the full sequence of the large transgene of interest, and when recombined, the fragments form the full sequence of the large transgene of interest, or a functional portion thereof.

In some embodiments, a triple AAV vector may include three separate AAV vectors, each including a fragment of the sequence of the large transgene of interest, and when recombined, the fragments form the full sequence of the large transgene of interest, or a functional portion thereof.

The multiple AAV vectors of the dual or triple AAV vectors can be delivered to and co-transduced into the same cell, where the two or three fragments of transgene recombine together and generate a single mRNA transcript of the entire large transgene of interest. In some embodiments, the fragmented transgenes include a non-overlapping sequences. In some embodiments, the fragmented transgenes include a specified overlapping sequences.

In some embodiments, the multiple AAV vectors of the dual or triple may be the same type of AAV vector. In some embodiments, the multiple AAV vectors of the dual or triple may be different types of AAV vector. In some embodiments, a first AAV vector, carrying a first fragment of a large transgene of interest may include AAV1, AAV2, AAV3 (e.g., AAV3B), AAV4, AAV5, AAV6, AAV7, AAV8, AAV9, AAV10, AAV11, or a variant thereof. In some embodiments, a second AAV vector, carrying a second fragment of a large transgene of interest may include AAV1, AAV2, AAV3 (e.g., AAV3B), AAV4, AAV5, AAV6, AAV7, AAV8, AAV9, AAV10, AAV11, or a variant thereof. In some embodiments, a third AAV vector, carrying a third fragment of a large transgene of interest may include AAV1, AAV2, AAV3 (e.g., AAV3B), AAV4, AAV5, AAV6, AAV7, AAV8, AAV9, AAV10, AAV11, or a variant thereof. A viral vector may also be based on an alphavirus. Alphaviruses include Sindbis(and VEEV) virus, Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, Semliki Forest virus (SFV), and Venezuelan equine encephalitis virus (VEEV) have all been used to develop viral transfer vectors for transgene delivery. Pseudotyped viruses may be formed by combining alphaviral envelope glycoproteins and retroviral capsids. Examples of alphaviral vectors can be found in U.S. Publication Nos. 20150050243, 20090305344, and 20060177819; the vectors and methods of their making are incorporated herein by reference in their entirety.

In addition to the major elements identified above for an AAV vector, the vector can also include conventional control elements operably linked to the transgene in a manner that permits its transcription, translation and/or expression in a cell transfected with the vector or infected with the virus produced by the disclosure. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters that are native, constitutive, inducible and/or tissue-specific, are known in the art and may be included in a vector described herein. In some embodiments, operably linked coding sequences yield a functional RNA (e.g., miRNA).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, a native promoter, or fragment thereof, for a transgene will be used. In a further embodiment, other native expression control elements, such as enhancer elements, polyadenylation sites or Kozak consensus sequences may also be used to mimic the native expression.

In some embodiments, regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken β-actin promoter, a pol II promoter, or a pol III promoter.

In some embodiments, a viral vector is designed for expressing a transgene described herein in hepatocytes, and viral vector (e.g., an AAV vector) includes one or more liver-specific regulatory elements, which substantially limit expression of the transgene to hepatic cells. Generally, liver-specific regulatory elements can be derived from any gene known to be exclusively expressed in the liver. WO 2009/130208 identifies several genes expressed in a liver-specific fashion, including serpin peptidase inhibitor, clade A member 1, also known as α-antitrypsin (SERPINA1; GeneID 5265), apolipoprotein C-I (APOC1; GeneID 341), apolipoprotein C-IV (APOC4; GeneID 346), apolipoprotein H (APOH; GeneID 350), transthyretin (TTR; GeneID 7276), albumin (ALB; GeneID 213), aldolase B (ALDOB; GeneID 229), cytochrome P450, family 2, subfamily E, polypeptide 1 (CYP2E1; GeneID 1571), fibrinogen alpha chain (FGA; GeneID 2243), transferrin (TF; GeneID 7018), and haptoglobin related protein (HPR; GeneID 3250). In some embodiments, a viral vector described herein includes a liver-specific regulatory element derived from the genomic loci of one or more of these proteins. In some embodiments, a promoter may be the liver-specific promoter thyroxin binding globulin (TBG). Alternatively, other liver-specific promoters may be used (see, e.g., The Liver Specific Gene Promoter Database, Cold Spring Harbor, rulai.cshl.edu/LSPD, such as, e.g., alpha 1 anti-trypsin (A1AT); human albumin (Miyatake et al., J. Virol. 71:5124 32 (1997)); humAlb; hepatitis B virus core promoter (Sandig et al., Gene Ther. 3:1002 9 (1996)); or LSP1. Additional vectors and regulatory elements are described in, e.g., Baruteau et al., J. Inherit. Metab. Dis. 40:497-517 (2017)).

II. Transgenes

The transgene of a viral vector described herein may be a gene therapy transgene and may encode any protein or portion thereof beneficial to a subject, such as one with a disease or disorder. The protein may be an extracellular, intracellular or membrane-bound protein. The protein can be a therapeutic protein. In some embodiments, the subject to whom the gene therapy is administered has a disease or disorder whereby the subject's endogenous version of the protein is defective or produced in limited amounts or not at all. In some such embodiments, the transgene encodes a non-defective version of the protein. In some embodiments, the subject to whom the gene therapy is administered has a disease or disorder mediated by a target gene (e.g., by a level of expression of the target gene and/or level of activity of a target polypeptide), and the transgene encodes an inhibitor of the target gene or target polypeptide. Examples of therapeutic proteins include, but are not limited to, infusible or injectable therapeutic proteins, enzymes, enzyme cofactors, hormones, blood or blood coagulation factors, cytokines and interferons, growth factors, adipokines, etc.

Examples of infusible or injectable therapeutic proteins include, for example, Tocilizumab (Roche/Actemra®), VEGF inhibitors, alpha-1 antitrypsin (Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), taliglucerase alfa (Protalix/Uplyso), agalsidase alfa (Shire/Replagal®), and velaglucerase alfa (Shire).

Examples of enzymes include lysozyme, oxidoreductases, transferases, hydrolases, lyases, isomerases, asparaginases, uricases, glycosidases, proteases, nucleases, collagenases, hyaluronidases, heparinases, heparanases, kinases, phosphatases, lysins and ligases. Other examples of enzymes include those that used for enzyme replacement therapy including, but not limited to, imiglucerase (e.g., CEREZYME™), a-galactosidase A (a-gal A) (e.g., agalsidase beta, FABRYZYME™), acid α-glucosidase (GAA) (e.g., alglucosidase alfa, LUMIZYME™, MYOZYME™), and arylsulfatase B (e.g., laronidase, ALDURAZYME™, idursulfase, ELAPRASE™, arylsulfatase B, NAGLAZYME™).

Examples of hormones include, but are not limited to, gonadotropins, thyroid-stimulating hormone, melanocortins, pituitary hormones, vasopressin, oxytocin, growth hormones, prolactin, orexins, natriuretic hormones, parathyroid hormone, calcitonins, erythropoietin, and pancreatic hormones.

Examples of blood or blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, von Heldebrant Factor, prekallikrein (Fletcher factor), high-molecular weight kininogen (HMWK) (Fitzgerald factor), fibronectin, fibrin, thrombin, antithrombin, such as antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGFα), Transforming growth factor beta (TGFβ), Tumour necrosis factor-alpha (TNFα), Vascular endothelial growth factor (VEGF), Wnt Signaling Pathway, placental growth factor (PIGF), [(Foetal Bovine Somatotrophin)] (FBS), IL-1, IL-2, IL-3, IL-4, IL-5, IL-6, and IL-7. Examples of adipokines include leptin and adiponectin.

Additional examples of therapeutic proteins include, but are not limited to, receptors, signaling proteins, cytoskeletal proteins, scaffold proteins, transcription factors, structural proteins, membrane proteins, cytosolic proteins, binding proteins, nuclear proteins, secreted proteins, golgi proteins, endoplasmic reticulum proteins, mitochondrial proteins, and vesicular proteins, etc.

The transgene of a gene therapy viral vector provided herein may encode a functional version of any protein that, through some defect in the endogenous version in a subject (including a defect in the expression of an endogenous version), results in a disease or disorder in the subject. In some embodiments, the endogenous version of a protein in a subject may be absent or underexpressed. Examples of such diseases or disorders include, but are not limited to, lysosomal storage diseases/disorders, such as Santavuori-Haltia disease (Infantile Neuronal Ceroid Lipofuscinosis Type 1), Jansky-Bielschowsky Disease (late infantile neuronal ceroid lipofuscinosis, Type 2), Batten disease (juvenile neuronal ceroid lipofuscinosis, Type 3), Kufs disease (neuronal ceroid lipofuscinosis, Type 4), Von Gierke disease (glycogen storage disease, Type Ia), glycogen storage disease, Type Ib, Pompe disease (glycogen storage disease, Type II), Forbes or Cori disease (glycogen storage disease, Type III), mucolipidosis II (I-Cell disease), mucolipidosis III (Pseudo-Hurler polydystrophy), mucolipdosis IV (sialolipidosis), cystinosis (adult nonnephropathic type), cystinosis (infantile nephropathic type), cystinosis (juvenile or adolescent nephropathic), Salla disease/infantile sialic acid storage disorder, and saposin deficiencies; disorders of lipid and sphingolipid degradation, such as GM1 gangliosidosis (infantile, late infantile/juvenile, and adult/chronic), Tay-Sachs disease, Sandhoff disease, GM2 gangliodisosis, Ab variant, Fabry disease, Gaucher disease, Types I, II and III, metachromatic leukidystrophy, Krabbe disease (early and late onset), Neimann-Pick disease, Types A, B, C1, and C2, Farber disease, and Wolman disease (cholesteryl esther storage disease); disorders of mucopolysaccharide degradation, such as Hurler syndrome (MPSI), Scheie syndrome (MPS IS), Hurler-Scheie syndrome (MPS IH/S), Hunter syndrome (MPS II), Sanfillippo A syndrome (MPS IIIA), Sanfillippo B syndrome (MPS IIIB), Sanfillippo C syndrome (MPS IIIC), Sanfillippo D syndrome (MPS IIID), Morquio A syndrome (MPS IVA), Morquio B syndrome (MPS IVB), Maroteaux-Lamy syndrome (MPS VI), and Sly syndrome (MPS VII); disorders of glycoprotein degradation, such as alpha mannosidosis, beta mannosidosis, fucosidosis, asparylglucosaminuria, mucolipidosis I (sialidosis), galactosialidosis, Schindler disease, and Schindler disease, Type II/Kanzaki disease; and leukodystrophy diseases/disorders, such as abetalipoproteinemia, neonatal adrenoleukodystrophy, Canavan disease, cerebrotendinous xanthromatosis, Pelizaeus Merzbacher disease, Tangier disease, Refum disease, infantile, and Refum disease, classic.

Additional examples of such diseases/disorders of a subject as provided herein include, but are not limited to, acid maltase deficiency (e.g., Pompe disease, glycogenosis type 2, lysosomal storage disease); carnitine deficiency; carnitine palmityl transferase deficiency; debrancher enzyme deficiency (e.g., Cori or Forbes disease, glycogenosis type 3); lactate dehydrogenase deficiency (e.g., glycogenosis type 11); myoadenylate deaminase deficiency; phosphofructokinase deficiency (e.g., Tarui disease, glycogenosis type 7); phosphogylcerate kinase deficiency (e.g., glycogenosis type 9); phosphogylcerate mutase deficiency (e.g., glycogenosis type 10); phosphorylase deficiency (e.g., McArdle disease, myophosphorylase deficiency, glycogenosis type 5); Gaucher's Disease (e.g., chromosome 1, enzyme glucocerebrosidase affected); Achondroplasia (e.g., chromosome 4, fibroblast growth factor receptor 3 affected); Huntington's Disease (e.g., chromosome 4, huntingtin); Hemochromatosis (e.g., chromosome 6, HFE protein); Cystic Fibrosis (e.g., chromosome 7, CFTR); Friedreich's Ataxia (chromosome 9, frataxin); Best Disease (chromosome 11, VMD2); Sickle Cell Disease (chromosome 11, hemoglobin); Phenylketoniuria (chromosome 12, phenylalanine hydroxylase); Marfan's Syndrome (chromosome 15, fibrillin); Myotonic Dystophy (chromosome 19, dystophia myotonica protein kinase); Adrenoleukodystrophy (x-chromosome, lignoceroyl-CoA ligase in peroxisomes); Duchene's Muscular Dystrophy (x-chromosome, dystrophin); Rett Syndrome (x-chromosome, methylCpG-binding protein 2); Leber's Hereditary Optic Neuropathy (mitochondria, respiratory proteins); Mitochondria Encephalopathy, Lactic Acidosis and Stroke (MELAS) (mitochondria, transfer RNA); and Enzyme deficiencies of the Urea Cycle.

Still additional examples of such diseases or disorders include, but are not limited to, Sickle Cell Anemia, Myotubular Myopathy, Hemophilia B, Lipoprotein lipase deficiency, Ornithine Transcarbamylase Deficiency, Crigler-Najjar Syndrome, Mucolipidosis IV, Niemann-Pick A, Sanfilippo A, Sanfilippo B, Sanfilippo C, Sanfilippo D, b-thalassaemia and Duchenne Muscular Dystrophy. Still further examples of diseases or disorders include those that are the result of defects in lipid and sphingolipid degradation, mucopolysaccharide degradation, glycoprotein degradation, leukodystrophies, etc.

The functional versions of the defective proteins of any one of the disease or disorders provided herein may be encoded by the transgene of a gene therapy viral vector and are also considered therapeutic proteins. Therapeutic proteins also include Myophosphorylase, glucocerebrosidase, fibroblast growth factor receptor 3, huntingtin, HFE protein, CFTR, frataxin, VMD2, hemoglobin, phenylalanine hydroxylase, fibrillin, dystophia myotonica protein kinase, lignoceroyl-CoA ligase, dystrophin, methylCpG-binding protein 2, Beta hemoglobin, Myotubularin, Cathepsin A, Factor IX, Lipoprotein lipase, Beta galactosidase, Ornithine Transcarbamylase, Iduronate-2-Sulfatase, Acid-Alpha Glucosidase, UDP-glucuronosyltransferase 1-1, GlcNAc-1-phosphotransferase, GlcNAc-1-phosphotransferase, Mucolipin-1, Microsomal triglyceride transfer protein, Sphingomyelinase, Acid ceramidase, Lysosomal acid lipase, Alpha-L-iduronidase, Heparan N-sulfatase, alpha-N-acetylglucosaminidase, acetyl-CoA alpha-glucosaminide acetyltransferase, N-acetylglucosamine 6-sulfatase, N-acetylgalactosamine-6 sulfatase, Alpha-mannosidase, Alpha-galactosidase A, Cystic fibrosis conductance transmembrane regulator, and respiratory proteins.

As further examples, therapeutic proteins also include functional versions of proteins associated with disorders of lipid and sphingolipid degradation (e.g., β-Galactosidase-1, β-Hexosaminidase A, β-Hexosaminidases A and B, GM2 Activator Protein, 8-Galactosidase A, Glucocerebrosidase, Glucocerebrosidase, Glucocerebrosidase, Arylsulfatase A, Galactosylceramidase, Sphingomyelinase, Sphingomyelinase, NPC1, HE1 protein (Cholesterol Trafficking Defect), Acid Ceramidase, Lysosomal Acid Lipase); disorders of mucopolysaccharide degradation (e.g., L-Iduronidase, L-Iduronidase, L-Iduronidase, Iduronate Sulfatase, Heparan N-Sulfatase, N-Acetylglucosaminidase, Acetyl-CoA-Glucosaminidase, Acetyltransferase, Acetylglucosamine-6-Sulfatase, Galactosamine-6-Sulfatase, Arylsulfatase B, Glucuronidase); disorders of glycoprotein degradation (e.g., Mannosidase, mannosidase, 1-fucosidase, Aspartylglycosaminidase, Neuraminidase, Lysosomal protective protein, Lysosomal 8-N-acetylgalactosaminidase, Lysosomal 8-N-acetylgalactosaminidase); lysosomal storage disorders (e.g., Palmitoyl-protein thioesterase, at least 4 subtypes, Lysosomal membrane protein, Unknown, Glucose-6-phosphatase, Glucose-6-phosphate translocase, Acid maltase, Debrancher enzyme amylo-1,6 glucosidase, N-acetylglucosamine-1-phosphotransferase, N-acetylglucosamine-1-phosphotransferase, Ganglioside sialidase (neuraminidase), Lysosomal cystine transport protein, Lysosomal cystine transport protein, Lysosomal cystine transport protein, Sialic acid transport protein Saposins, A, B, C, D) and leukodystrophies (e.g., Microsomal triglyceride transfer protein/apolipoprotein B, Peroxisomal membrane transfer protein, Peroxins, Aspartoacylase, Sterol-27-hydroxlase, Proteolipid protein, ABC1 transporter, Peroxisome membrane protein 3 or Peroxisome biogenesis factor 1, Phytanic acid oxidase).

The viral vectors provided herein may be used for gene editing. In such embodiments, the transgene of the viral vector is a gene editing transgene. Such a transgene encodes an agent or component that is involved in a gene editing process. Generally, such a process results in long-lasting or permanent modifications to genomic DNA, such as targeted DNA insertion, replacement, mutagenesis or removal. Gene editing may include the delivery of nucleic acids encoding a DNA sequence of interest and inserting the sequence of interest at a targeted site in genomic DNA using endonucleases. Thus, gene editing transgenes may comprise these nucleic acids encoding a DNA sequence of interest for insertion. In some embodiments, the DNA sequence for insertion is a DNA sequence encoding any one of the therapeutic proteins described herein. Additionally or alternatively, the gene editing transgene may comprise nucleic acids that encode one of more components that can alone or in combination with other components carry out the gene editing process. The gene editing transgenes provided herein may encode an endonuclease and/or a guide RNA, etc.

Endonucleases can create breaks in double-stranded DNA at desired locations in a genome and use the host cell's mechanisms to repair the break using homologous recombination, nonhomologous end-joining, etc. Classes of endonucleases that can be used for gene editing include, but are not limited to, meganucleases (see, e.g., U.S. Pat. Nos. 8,802,437, 8,445,251 and 8,338,157; and U.S. Publication Nos. 20130224863, 20110113509 and 20110033935), zinc-finger nucleases (ZFNs) (see, e.g., U.S. Pat. Nos. 8,956,828; 8,921,112; 8,846,578; 8,569,253), transcription activator-like effector nucleases (TALENs) (see, e.g., U.S. Pat. No. 8,697,853; as well as U.S. Publication Nos. 20150118216, 20150079064, and 20140087426), clustered regularly interspaced short palindromic repeat(s) (CRISPR) and homing endonucleases (see, e.g., U.S. Publication No. 20150166969; and U.S. Pat. No. 9,005,973).

The gene editing transgene of the viral vectors provided herein may encode any one of the endonucleases provided herein. For example, the CRISPR (clustered regularly interspaced short palindromic repeats)/Cas system can be used for gene editing. In a CRISPR/Cas system, guide RNA (gRNA) is encoded genomically or episomally (e.g., on a plasmid). The gRNA forms a complex with an endonuclease, such as Cas9 endonuclease, following transcription. The complex is then guided by the specificity determining sequence (SDS) of the gRNA to a DNA target sequence, typically located in the genome of a cell. Cas9 or Cas9 endonuclease refers to an RNA-guided endonuclease comprising a Cas9 protein, or a fragment thereof (e.g., a protein comprising an active or inactive DNA cleavage domain of Cas9 or a partially inactive DNA cleavage domain (e.g., a Cas9 nickase), and/or the gRNA binding domain of Cas9). Cas9 recognizes a short motif in the CRISPR repeat sequences (the PAM or protospacer adjacent motif) to help distinguish self versus non-self. Cas9 endonuclease and guide RNA (e.g., single guide RNA) sequences and structures are well known to those of skill in the art (see, e.g., Ferretti et al., Proc. Natl. Acad. Sci. U.S.A. 98:4658-4663 (2001); Deltcheva et al., Nature 471:602-607 (2011); and Jinek et al., Science 337:816-821 (2012)).

The viral vectors provided herein may be used for gene expression modulation. In such embodiments, the transgene of the viral vector is a gene expression modulating transgene. Such a transgene encodes a gene expression modulator that can enhance, inhibit (e.g., silence) or modulate the expression of one or more endogenous genes. The endogenous gene may encode any one of the proteins as provided herein provided the protein is an endogenous protein of the subject. Accordingly, the subject may be one with any one of the diseases or disorders provided herein where there would be a benefit provided by gene expression modulation.

Gene expression modulators include DNA-binding proteins (e.g., artificial transcription factors, such as those of U.S. Publication No. 20140296129; and transcriptional silencer protein NRF of U.S. Publication No. 20030125286) as well as therapeutic RNAs. Therapeutic RNAs include, but are not limited to, inhibitors of mRNA translation (antisense) (see, e.g., U.S. Publication Nos. 20050020529 and 20050271733), agents of RNA interference (RNAi) (see, e.g., U.S. Pat. Nos. 8,993,530, 8,877,917, 8,293,719, 7,947, 659, 7,919,473, 7,790,878, 7,737,265, 7,592,322; and U.S. Publication Nos. 20150197746, 20140350071, 20140315835, 20130156845 and 20100267805), catalytically active RNA molecules (ribozymes) (see, e.g., Hasselhoff, et al., Nature, 334:585, 1988; and U.S. Publication No. 20050020529), transfer RNA (tRNA) and RNAs that bind proteins and other molecular ligands (aptamers). Gene expression modulators include any agents of the foregoing and include antisense nucleic acids, RNAi molecules (e.g., double-stranded RNAs (dsRNAs), single-stranded RNAs (ssRNAs), micro RNAs (miRNAs), short interfering RNAs (siRNAs), short hairpin RNAs (shRNAs)) and triplex-forming oligonucleotides (TFOs). Gene expression modulators also may include modified versions of any of the foregoing RNA molecules and, thus, include modified mRNAs, such as synthetic chemically modified RNAs.

Exemplary transgenes encode interfering RNA, antisense RNA, ribozymes, and aptamers that decrease the level of an angiogenic factor in a cell. For example, an RNAi can be a miRNA, an shRNA, or an siRNA that reduces the level of vascular endothelial growth factor (VEGF) in a cell. For example, an RNAi can be an shRNA or siRNA that reduces the level of VEGF or VEGF receptor (VEGFR) in a cell. RNAi agents that target VEGF include, e.g., an RNAi described in U.S. Patent Publication No. 2011/0224282. For example, an siRNA specific for VEGF-A, VEGFR1, or VEGFR2 would be suitable. Suitable nucleic acid gene products also include a ribozyme specific for VEGF-A, VEGFR1, or VEGFR2; an antisense specific for VEGF-A, VEGFR1, or VEGFR2; siRNA specific for VEGF-A, VEGFR1, or VEGFR2; etc. Also suitable as a gene product is an miRNA that reduces the level of VEGF by regulating VEGF gene expression, e.g., through post-transcriptional repression or mRNA degradation. Examples of suitable miRNA include, e.g., miR-15b, miR-16, miR-20a, and miR-20b. See, e.g., Hua et al. (2006) PLOS ONE 1: e116. Also suitable is an anti-VEGF aptamer (e.g., EYE001). For anti-VEGF aptamers, see, e.g., Ng et al. (2006) Nature Reviews Drug Discovery5: 123; and U.S. Pat. Nos. 6,426, 335; 6,168,778; 6,147,204; 6,051,698; and 6,011,020. For example, an aptamer can be directed against VEGF165, the isoform primarily responsible for pathological ocular neovascularization and vascular permeability.

In some embodiments, a transgene encodes a polypeptide (e.g., an antibody or fusion protein) that inhibits or reduces activity of one or more polypeptides described herein. For example, in some embodiments, a transgene encodes an anti-angiogenic polypeptide including, e.g., vascular endothelial growth factor (VEGF) antagonists. Suitable VEGF antagonists include, but are not limited to, inhibitors of VEGFR1 tyrosine kinase activity; inhibitors of VEGFR2 tyrosine kinase activity; an antibody to VEGF; an antibody to VEGFR1; an antibody to VEGFR2; a soluble VEGFR; and the like (see, e.g., Takayama et al. (2000) Cancer Res. 60:2169-2177; Mori et al. (2000) Gene Ther. 7:1027-1033; and Mahasreshti et al. (2001) Clin. CancerRes. 7:2057-2066; and U.S. Patent Publication No. 20030181377). Antibodies specific for VEGF include, e.g., bevacizumab (AVASTIN™) and ranibizumab (also known as rhuFAb V2). Also suitable for use are anti-angiogenic polypeptides such as endostatin, PEDF, and angiostatin.

Anti-angiogenic polypeptides include, e.g., recombinant polypeptides comprising VEGF receptors. For example, a suitable anti-angiogenic polypeptide can be the soluble form of the VEGFR-1, known as sFlt-1 (Kendall et al. (1996) Biochem. Biophys. Res. Commun.226:324). Suitable anti-angiogenic polypeptides also include an immunoglobulin-like (Ig) domain 2 of a first VEGF receptor (e.g., Flt1), alone or in combination with an Ig domain 3 of a second VEGF receptor (e.g., Flk1 or Flt4); an anti-angiogenic polypeptide can also include a stabilization and/or a multimerization component. Such recombinant anti-angiogenic polypeptides are described in, e.g., U.S. Pat. No. 7,521,049. Anti-VEGF antibodies that are suitable as heterologous gene products include single chain Fv (scFv) antibodies. See, e.g., U.S. Pat. Nos. 7,758,859; and 7,740,844, for anti-VEGF antibodies. Additional transgenes are described in, e.g., Bordet et al., Drug Discov Today. 2019 Jun. 5. pii: S1359-6446 (18) 30472-0. doi: 10.1016/j.drudis.2019.05.038. Such transgenes can be used to treat ocular disorders, e.g., age-related macular degeneration.

In some embodiments, the gene therapy comprises an adeno-associated virus, serotype 9 (AAV9) vector comprising a truncated human dystrophin gene (mini-dystrophin) under the control of a muscle specific promoter. In some embodiments, the mini-dystrophin gene comprises a 6-8 kb sequence of the full length dystrophin gene. In some embodiments, the mini-dystrophin gene may contain a fragment of the full dystrophin gene sequence, while still containing the minimal amount of information required for production of function dystrophin protein. In some embodiments, the mini-dystrophin genes contain at least the R16/R17 nNOS binding domain sequence of the dystrophin gene (e.g., as described in Zhang et al. *Human Gene Ther.*2012

January; 23 (1): 98-103). For example, in some embodiments the gene therapy may be PF-06939926. The gene therapy may be administered, e.g., by IV infusion, to a subject suffering from Duchenne muscular dystrophy (DMD). In some embodiments, the mini-dystrophin gene therapy may be delivered using more than one AAV vector, such as a dual or triple AAV vector.

In some embodiments, the gene therapy comprises an AAV9 vector comprising a micro-dystrophin gene under the control of a muscle specific promoter. The micro-dystrophin gene may contain a fragment of the full dystrophin gene sequence, while still containing the minimal amount of information required for production of function dystrophin protein. In some embodiments, a micro-dystrophin gene may comprise the sequence of the dystrophin gene with one or more of the R1-R24 segments of spectrin-like repeats removed. For example, in some embodiments the gene therapy may be SGT-001. In some embodiments, the micro-dystrophin gene may include ΔDysM3 is the first synthetic micro-dystrophin. Δ3990, ΔR4-23/ΔC and μDys5R (as described in Duan 2018 *Molecular Therapy* 26 (10)). In some embodiments, the micro-dystrophin gene therapy may be delivered using more than one AAV vector, each containing a different micro-dystrophin gene. The gene therapy may be administered, e.g., by IV infusion, to a subject suffering from DMD.

In some embodiments, the gene therapy comprises an adeno-associated virus, serotype 5 (AAV5) vector comprising a human Factor IX gene. The gene therapy may be administered, e.g., by IV infusion, to a subject suffering from hemophilia B. In some embodiments, a gene therapy vector encodes a functional version that has gain-of-function activity (e.g., increased expression or activity relative to wild type). For example, for hemophilia involving lack of Factor IX, a Factor IX variant that contains the gain-of-function mutation known as Padua (R338L) which leads to an enhancement of expression of Factor IX, may be used. For example, in some embodiments, the gene therapy is AMT-061.

In some embodiments, the gene therapy comprises an AAV Serotype 8 (AAV8) vector comprising a transgene encoding human ornithine transcarbamylase (OTC). The gene therapy may be administered, e.g., by IV infusion, to subjects suffering from OTC deficiency. In some embodiments the gene therapy is DTX301.

In some embodiments, the gene therapy comprises an adeno-associated virus, serotype 5 (AAV5) vector comprising a human Factor VIII gene. The gene therapy may be administered, e.g., by IV infusion, to a subject suffering from hemophilia A. In some embodiments, the gene therapy is Valoctocogene Roxaparvovec.

In some embodiments, the gene therapy comprises an AAV8 vector comprising the human GAA gene under the control of the LSP promoter. The gene therapy may be administered, e.g., by IV infusion, to a subject suffering from Pompe disease.

In some embodiments, the gene therapy comprises an AAV8 vector comprising a transgene encoding human glucose-6-phosphatase (G6Pase). The gene therapy may be administered, e.g., by IV infusion, to a subject suffering from glycogen storage disease type Ia (GSDIa).

In some embodiments, the gene therapy comprises an adeno-associated virus serotype 9 (AAV9) vector comprising a transgene encoding the human lysosome-associated membrane protein 2 isoform B (LAMP2B) (e.g., RP-A501). In some embodiments, the gene therapy is administered, e.g., by IV infusion, to a subject suffering from Danon Disease.

In some embodiments, the gene therapy comprises an AAV vector, e.g., an AAV8 vector, comprising a transgene that encodes human LDL receptor. The gene therapy may be administered, e.g., by IV infusion, to a subject suffering from familial hypercholesterolemia (e.g., homozygous familial hypercholesterolemia). In some embodiments, the gene therapy comprises AAV8.TBG.hLDLR.

In some embodiments, the gene therapy comprises an adeno-associated virus serotype 2 vector (AAV2) comprising a normal human CHM gene (encoding REP1). The gene therapy may be administered sub-retinally to a subject suffering from or at risk of choroideremia.

In some embodiments, the gene therapy comprises an AAV2 vector comprising a transgene that encodes human RPE65, e.g., AAV2-hRPE65v2. The gene therapy may be administered, e.g., subretinally, to a subject suffering from Leber Congenital Amaurosis.

In some embodiments, the gene therapy comprises an adeno-associated virus 2/6 (AAV2/6) vector encoding a B-domain deleted human Factor VIII (e.g., SB-525). In some embodiments, the gene therapy comprises an adeno-associated virus 8 vector encoding a B-domain deleted human Factor VIII (e.g., BAX 888). The gene therapy providing B-domain deleted human Factor VIII may be administered, e.g., by IV infusion, to a subject suffering from hemophilia A.

In some embodiments, the gene therapy comprises an AAV9 vector comprising a human CLN3 transgene. The therapy may be administered, e.g., intrathecally, to a subject having a CLN3 mutation. In some embodiments, the gene therapy comprises an AAV9 vector comprising a human CLN6 transgene. The therapy may be administered, e.g., intrathecally, to a subject having a CLN6 mutation.

In some embodiments, the gene therapy comprises an AAV8 vector containing a functional copy of the human MTM1 (hMTM1) gene (e.g., AT132). The gene therapy may be administered, e.g., by IV infusion, to a subject suffering from X-Linked Myotubular Myopathy.

In some embodiments, a viral vector described herein includes (i) a transgene described herein and (ii) a nucleic acid encoding a complement inhibitor described herein.

The sequence of a transgene may also include an expression control sequence. Expression control DNA sequences include promoters, enhancers, and operators, and are generally selected based on the expression systems in which the expression construct is to be utilized. In some embodiments, promoter and enhancer sequences are selected for the ability to increase gene expression, while operator sequences may be selected for the ability to regulate gene expression. The transgene may also include sequences that facilitate, and preferably promote, homologous recombination in a host cell. The transgene may also include sequences that are necessary for replication in a host cell.

Exemplary expression control sequences include promoter sequences, e.g., cytomegalovirus promoter; Rous sarcoma virus promoter; and simian virus 40 promoter; as well as any other types of promoters that are disclosed elsewhere herein or are otherwise known in the art. Generally, promoters are operatively linked upstream (i.e., 5') of the sequence coding for a desired expression product. The transgene also may include a suitable polyadenylation sequence (e.g., the SV40 or human growth hormone gene polyadenylation sequence) operably linked downstream (i.e., 3') of the coding sequence.

III. Production of Viral Vectors

Methods for obtaining viral vectors are known in the art. For example, to produce AAV vectors, the methods typically involve culturing a host cell which contains a nucleic acid sequence encoding an AAV capsid protein or fragment thereof; a functional rep gene; a recombinant AAV vector composed of AAV inverted terminal repeats (ITRs) and a transgene; and/or sufficient helper functions to permit packaging of the recombinant AAV vector into the AAV capsid proteins.

The components to be cultured in a host cell to package an AAV vector in an AAV capsid may be provided to the host cell in trans. Alternatively, any one or more of the required components (e.g., recombinant AAV vector, rep sequences, cap sequences, and/or helper functions) may be provided by a stable host cell that has been engineered to contain one or more of the required components using methods known to those of skill in the art. In some embodiments, such a stable host cell contains the required component(s) under the control of an inducible promoter. In other embodiments, the required component(s) may be under the control of a constitutive promoter. In other embodiments, a selected stable host cell may contain selected component(s) under the control of a constitutive promoter and other selected component(s) under the control of one or more inducible promoters. For example, a stable host cell may be generated that is derived from 293 cells (which contain E1 helper functions under the control of a constitutive promoter), but that contain the rep and/or cap proteins under the control of inducible promoters. Other stable host cells may be generated by one of skill in the art using routine methods.

Recombinant AAV vector, rep sequences, cap sequences, and helper functions required for producing an AAV of the disclosure may be delivered to a packaging host cell using any appropriate genetic element (e.g., vector). A selected genetic element may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y.). Similarly, methods of generating AAV virions are well known and any suitable method can be used with the present disclosure (see, e.g., K. Fisher et al, J. Virol., 70:520-532 (1993) and U.S. Pat. No. 5,478,745).

In some embodiments, recombinant AAVs may be produced using a triple transfection method (e.g., as described in U.S. Pat. No. 6,001,650). In some embodiments, recombinant AAVs are produced by transfecting a host cell with a recombinant AAV vector (comprising a transgene) to be packaged into AAV particles, an AAV helper function vector, and an accessory function vector. An AAV helper function vector encodes "AAV helper function" sequences (i.e., rep and cap), which function in trans for productive AAV replication and encapsidation. In some embodiments, the AAV helper function vector supports efficient AAV vector production without generating any detectable wild-type AAV virions (i.e., AAV virions containing functional rep and cap genes). Non-limiting examples of vectors suitable for use with the present disclosure include pHLP19 (see, e.g., U.S. Pat. No. 6,001,650) and pRep6cap6 vector (see, e.g., U.S. Pat. No. 6,156,303). An accessory function vector encodes nucleotide sequences for non-AAV derived viral and/or cellular functions upon which AAV is dependent for replication (i.e., "accessory functions"). Accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any known helper viruses such as adenovirus, herpesvirus (other than herpes simplex virus type-1), and vaccinia virus.

In some embodiments, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art (see, e.g., Graham et al. (1973) Virology, 52:456; Sambrook et al. (1989) Molecular Cloning, a laboratory manual, Cold Spring Harbor Laboratories, New York, Davis et al. (1986) Basic Methods in Molecular Biology, Elsevier; and Chu et al. (1981) Gene 13:197). Such techniques can be used to introduce one or more exogenous nucleic acids, such as a nucleotide integration vector and other nucleic acid molecules, into suitable host cells.

In some embodiments, a host cell is a mammalian cell. A host cell may be used as a recipient of an AAV helper construct, an AAV minigene plasmid, an accessory function vector, and/or other transfer DNA associated with the production of recombinant AAVs. The term includes the progeny of an original cell that has been transfected. Thus, a "host cell" as used herein may refer to a cell that has been transfected with an exogenous DNA sequence. It is understood that the progeny of a single parental cell may not necessarily be completely identical in morphology or in genomic or total DNA complement as the original parent, due to natural, accidental, or deliberate mutation.

Additional methods for generating and isolating AAV viral vectors suitable for delivery to a subject are described in, e.g., U.S. Pat. Nos. 7,790,449; 7,282,199; WO 2003/042397; WO 2005/033321, WO 2006/110689; and U.S. Pat. No. 7,588,772. In one system, a producer cell line is transiently transfected with a construct that encodes the transgene flanked by ITRs and a construct(s) that encodes rep and cap. In another system, a packaging cell line that stably supplies rep and cap is transiently transfected with a construct encoding the transgene flanked by ITRs. In each of these systems, AAV virions are produced in response to infection with helper adenovirus or herpesvirus, and AAVs are separated from contaminating virus. Other systems do not require infection with helper virus to recover the AAV—the helper functions (i.e., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of the cells with constructs that encode the helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect host cells by infection with baculovirus-based vectors. Such production systems are known in the art (see generally, e.g., Zhang et al., 2009, Human Gene Therapy 20:922-929). Methods of making and using these and other AAV production systems are also described in U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The foregoing methods for producing recombinant vectors are not meant to be limiting, and other suitable methods will be apparent to the skilled artisan.

IV. Complement System

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by and amplified at, e.g., microbial surfaces and various complex polysaccharides. In this pathway, hydrolysis of C3 to C3 ($H_2O$), which occurs spontaneously at a low level, leads to binding of factor B, which is cleaved by factor D, generating a fluid phase C3 convertase that activates complement by cleaving C3 into C3a and C3b. C3b binds to targets such as cell surfaces and forms a complex with factor B, which is later cleaved by factor D, resulting in a C3 convertase. Surface-bound C3 convertases cleave and activate additional C3 molecules, resulting in rapid C3b deposition in close proximity to the site of activation and leading to formation of additional C3 convertase, which in turn generates additional C3b. This process results in a cycle of C3 cleavage and C3 convertase formation that significantly amplifies the response. Cleavage of C3 and binding of another molecule of C3b to the C3 convertase gives rise to a C5 convertase. C3 and C5 convertases of this pathway are regulated by cellular molecules CR1, DAF, MCP, CD59, and fH. The mode of action of these proteins involves either decay accelerating activity (i.e., ability to dissociate convertases), ability to serve as cofactors in the degradation of C3b or C4b by factor I, or both. Normally the presence of complement regulatory proteins on cell surfaces prevents significant complement activation from occurring thereon.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above. Further details are found, e.g., in Kuby Immunology, 6th ed., 2006; Paul, W. E., Fundamental Immunology, Lippincott Williams & Wilkins; 6th ed., 2008; and Walport M J., Complement. First of two parts. N Engl J Med., 344 (14): 1058-66, 2001.

Complement activity is regulated by various mammalian proteins referred to as complement control proteins (CCPs) or regulators of complement activation (RCA) proteins (U.S. Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b: C4b receptor), complement receptor type 2 (CR2), membrane cofactor protein (MCP; CD46), decay-accelerating factor (DAF), complement factor H (fH), and C4b-binding protein (C4 bp). CD59 is a membrane-bound complement regulatory protein unrelated structurally to the CCPs. Complement regulatory proteins normally serve to limit complement activation that might otherwise occur on cells and tissues of the mammalian, e.g., human host. Thus, "self" cells are normally protected from the deleterious effects that would otherwise ensue were complement activation to proceed on these cells. Deficiencies or defects in complement regulatory protein(s) are involved in the pathogenesis of a variety of complement-mediated disorders, e.g., as discussed herein.

V. Complement Inhibitors (i) Compstatin Analogs

Compstatin is a cyclic peptide that binds to C3 and inhibits complement activation. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., Protein Sci., 7 (3): 619-27, 1998) to refer to a peptide having the same sequence as SEQ ID NO: 2 disclosed in U.S. Pat. No. 6,319,897, but amidated at the C terminus as shown in Table 1 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32 (Pt 1): 28-32, 2004, Mallik, B., et al., *J. Med. Chem.,* 274-286, 2005; Katragadda, M., et al. *J. Med. Chem.,* 49:4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof.

The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 μM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more. In certain embodiments the $IC_{50}$ of the compstatin analog is between about 0.2 μM and about 0.5 μM. In certain embodiments the $IC_{50}$ of the compstatin analog is between about 0.1 μM and about 0.2 μM. In certain embodiments the $IC_{50}$ of the compstatin analog is between about 0.05 μM and about 0.1 μM. In certain embodiments the $IC_{50}$ of the compstatin analog is between about 0.001 μM and about 0.05 μM.

The $K_d$ of compstatin binding to C3 can be measured using isothermal titration calorimetry (Katragadda, et al., *J. Biol. Chem.,* 279 (53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 μM and 1.0 μM, between 0.05 μM and 0.1 μM, between 0.025 μM and 0.05 μM, between 0.015 μM and 0.025 μM, between 0.01 μM and 0.015 μM, or between 0.001 μM and 0.01 μM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-NaI), 1-naphthylalanine (1-NaI), 2-indanylglycine carboxylic acid (2Ig1), dihydrotrpytophan (Dht), 4-benzoyl-L-phenylalanine (Bpa), 2-cx-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH-W), 5-hydroxy-L-tryptophan (5OH—W), 6-hydroxy-L-tryptophan (6OH—W), 1-methyl-L-tryptophan (1MeW), 4-methyl-L-tryptophan (4MeW), 5-methyl-L-tryptophan (5MeW), 7-aza-L-tryptophan (7aW), «-methyl-L-tryptophan (aMeW), β-methyl-L-tryptophan (BMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. *Biochemistry* 41:10262-10269, 2002 (describing, inter alia, singly- and multiply-halogenated Trp analogs); Babitzke & Yanofsky, *J. Biol. Chem.* 270:12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N (a) methyl tryptophan or 5-methyltryptophan is used. In some embodiments, an analog comprising a 1-alkanyol substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X"aa)$_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly, where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-napthylalanine, 1-napthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is (X'aa) n and the other of which is located within (X"aa) m. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments, one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X"aa4 in SEQ ID NO: 5 (or corresponding positions in other sequences) with addition of a $CH_2$, to form a homocysteine at X'aa2 or X"aa4, and introduction of a thioether bond, to form a cystathionine. In one embodiment, the cystathionine is a gamma-cystathionine. In another embodiment, the cystathionine is a delta-cystathionine. Another modification in accordance with the present invention comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 6); wherein:

Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal-OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-NaI), 1-naphthylalanine (1-NaI), 2-indanylglycine carboxylic acid (Ig1), dihydrotrpytophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the-OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine ($—NH_2$ or $—NHR^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 7); wherein:

- Xaa1 is Ile, Val, Leu, Ac-Ile, Ac-Val, Ac-Leu or a dipeptide comprising Gly-Ile or Ac-Gly-Ile;
- Xaa2 and Xaa2* are independently selected from Trp and analogs of Trp;
- Xaa3 is His, Ala or an analog of Ala, Phe, Trp, or an analog of Trp;
- Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by-$NH_2$; and the two Cys residues are joined by a disulfide bond. In some embodiments, Xaa4 is Leu, Nle, His, or Phe or a dipeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments, Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 1 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 1 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 1 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 1 contains at least one N-methyl glycine, e.g., at the position corresponding to position 8 of compstatin and/or at the position corresponding to position 13 of compstatin. In some embodiments, one or more of the compstatin analogs in Table 1 contains at least one N-methyl isoleucine, e.g., at the position corresponding to position 13 of compstatin. For example, a Thr at or near the C-terminal end of a peptide whose sequence is listed in Table 1 or any other compstatin analog sequence may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4. In some embodiments the N-methylated amino acids comprise N-methyl Gly in a core sequence such as SEQ ID NO: 5, SEQ ID NO: 6, or SEQ ID NO: 7.

TABLE 1

| Peptide | Sequence | SEQ ID NO: | Activity over compstatin |
|---|---|---|---|
| Compstatin | *H*-ICVVQDWGHHRCT-*CONH2* | 8 | * |
| Ac-compstatin | *Ac*-ICVVQDWGHHRCT-*CONH2* | 9 | 3xmore |
| Ac-V4Y/H9A | *Ac*-ICV**Y**QDWG**A**HRCT-*CONH2* | 10 | 14xmore |
| Ac-V4W/H9A-OH | *Ac*-ICV**W**QDWG**A**HRCT-*COOH* | 11 | 27xmore |
| Ac-V4W/H9A | *Ac*-ICV**W**QDWG**A**HRCT-*CONH2* | 12 | 45xmore |
| Ac-V4W/H9A/T13dT-OH | *Ac*-ICV**W**QDWG**A**HRC**dT**-*COOH* | 13 | 55xmore |
| Ac-V4(2-Nal)/H9A | *Ac*-ICV**(2-Nal)**QDWG**A**HRCT-*CONH2* | 14 | 99xmore |
| Ac V4(2-Nal)/H9A-OH | *Ac*-ICV**(2-Nal)**QDWG**A**HRCT-*COOH* | 15 | 38xmore |
| Ac V4(1-Nal)/H9A-OH | *Ac*-ICV**(1-Nal)**QDWG**A**HRCT-*COOH* | 16 | 30xmore |
| Ac-V42lgl/H9A | *Ac*-ICV**(2-lgl)**QDWG**A**HRCT-*CONH2* | 17 | 39xmore |
| Ac-V42lgl/H9A-OH | *Ac*-ICV**(2-Igl)**QDWG**A**HRCT-*COOH* | 18 | 37xmore |
| Ac-V4Dht/H9A-OH | *Ac*-ICV**Dht**QDWG**A**HRCT-*COOH* | 19 | 5xmore |
| Ac-V4(Bpa)/H9A-OH | *Ac*-ICV**(Bpa)**QDWG**A**HRCT-*COOH* | 20 | 49xmore |
| Ac-V4(Bpa)/H9A | *Ac*-ICV**(Bpa)**QDWG**A**HRCT-*CONH2* | 21 | 86xmore |
| Ac-V4(Bta)/H9A-OH | *Ac*-ICV**(Bta)**QDWG**A**HRCT-*COOH* | 22 | 65xmore |
| Ac-V4(Bta)/H9A | Ac-ICV**(Bta)**QDWG**A**HRCT-*CONH2* | 23 | 64xmore |

TABLE 1-continued

| Peptide | Sequence | SEQ ID NO: | Activity over compstatin |
|---|---|---|---|
| Ac-V4W/H9(2-Abu) | *Ac*-ICV**W**QDWG(2-**Abu)**HRCT-*CONH2* | 24 | 64xmore |
| +G/V4W/H9A+AN-OH | H-**G**ICV**W**QDWG**A**HRCTA**N**-*COOH* | 25 | 38xmore |
| Ac-V4(5fW)/H9A | *Ac*-ICV**(5fW)**QDWG**A**HRCT-$CONH_2$ | 26 | 31xmore |
| Ac-V4(5-MeW)/H9A | *Ac*-ICV**(5-methyl-W)**QDWG**A**HRCT-$CONH_2$ | 27 | 67xmore |
| Ac-V4(1-MeW)/H9A | *Ac*-ICV**(1-methyl-W)**QDWG**A**HRCT-$CONH_2$ | 28 | 264xmore |
| Ac-V4W/W7(5fW)/H9A | *Ac*-ICV**W**QD**(5fW)**G**A**HRCT-$CONH_2$ | 29 | 121xmore |
| Ac-V4(5fW)/W7(5fW)/H9A | *Ac*-ICV**(5fW)**QD**(5fW)**G**A**HRCT-$CONH_2$ | 30 | NA |
| Ac-V4(5-MeW)/W7(5fW)H9A | *Ac*-ICV**(5-methyl-W)**QD**(5fW)**G**A**HRCT-$CONH_2$ | 31 | NA |
| Ac-V4(1MeW)/W7(5fW)/H9A | *Ac*-ICV**(1-methyl-W)**QD**(5fW)**G**A**HRCT-$CONH_2$ | 32 | 264xmore |
| +G/V4(6fW)/W7(6fW)H9A+N-OH | *H*-GICV**(6fW)**QD(6fW)G**A**HRCT**N**-*COOH* | 33 | 126xmore |
| Ac-V4(1-formyl-W)/H9A | *Ac*-ICV**(1-formyl-W**QDWG**A**HRCT-$CONH_2$ | 34 | 264xmore |
| Ac-V4(5-methoxy-W)/H9A | *Ac*-ICV**(1-methyoxy-W)**QDWG**A**HRCT-$CONH_2$ | 35 | 76xmore |
| G/V4(5f-W)/W7(5fW)/H9A+N-OH | *H*-GICV(**(5fW**)QD(**5fW**)G**A**HRCT**N**-*COOH* | 36 | 112xmore |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety $B^{1a}$ is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$ For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., $NH_2$). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments, Xaa0 and/or XaaN in $B^{1a}$-Xaa0 and/or XaaN-$B^2$a may function mainly to increase affinity or activity of the compound, while $B^{1a}$ and/or $B^{2a}$ may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^2$a. where SEQUENCE represents any of SEQ ID NOs: 5-36, wherein $B^1a$ and $B^{2a}$ may independently be present or absent. For example, in some embodiments a compstatin analog comprises $B^{1a}$-Xaa0-X'aa1-X'aa2-X'aa3-X'aa4-Gln-Asp-Xaa-Gly-X"aa1-X"aa2-X"aa3-X"aa4-X"aa5-XaaN-$B^2a$ (SEQ ID NO: 69), where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises $B^{1a}$-Xaa0-Xaa1-Cys-Val-Xaa2-Gln-Asp-Xaa2*-Gly-Xaa3-His-Arg-Cys-Xaa4-XaaN-$B^2a$ (SEQ ID NO: 70), where Xaa1, Xaa2, Xaa2*, Xaa3, and Xaa4 are as set forth above for SEQ ID NO: 6 or wherein Xaa1, Xaa2, Xaa2*, Xaa3, and Xaa4 are as set forth for SEQ ID NO: 6 or SEQ ID NO: 7.

In some embodiments a compstatin analog comprises $B^{1a}$-Xaa0-Xaa1-Xaa2-Xaa3-Xaa4-Xaa5-Xaa6-Xaa7-Xaa8-Xaa9-Xaa10-Xaa11-Xaa12-Xaa13-XaaN-$B^2a$ (SEQ ID NO: 71) wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, m Val, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence $B^1$-Ile-[Cys-Val-Trp(Me)-Gln-Asp-Trp-mGly-Ala-His-Arg-Cys]-mIle-$B^2$ (SEQ ID NO: 72). The two Cys residues are joined by a disulfide bond in the active compounds. In some embodiments the peptide is acetylated at the N-terminus and/or amidated at the C-terminus. In some embodiments $B^1$ comprises $B^{1a}$_Xaa0 and/or $B^2$ comprises XaaN-$B^{2a}$, as described above. For example, in some embodiments $B^1$ comprises or consists of Gly, mGly, Tyr, Phe, Arg, Trp, Thr, Tyr(Me), mPhe, mVal, mIle, *mAla*, DTyr, DPhe, DTrp, DCha, DAla and $B^2$ comprises $NH_2$. e.g., a carboxy terminal —OH of mIle is replaced by $NH_2$ . . . . In some embodiments $B^1$ comprises or consists of mGly, Tyr, DTyr, or Tyr(Me) and $B^2$ comprises $NH_2$, e.g., a carboxy terminal —OH of mIle is replaced by $NH_2$. In some embodiments an Ile at position Xaa1 is replaced by Gly. Complement inhibition potency and/or C3b binding parameters of selected compstatin analogs are described in WO/2010/127336 (PCT/US2010/033345) and/or in Qu, et al., Immunobiology (2012), doi: 10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 1, but where the Ac-group is replaced by an alternate blocking moiety $B^1$, as described herein. In some embodiments the-$NH_2$ group is replaced by an alternate blocking moiety $B^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., Mol. Immunol., 35:160, 1998; Soulika, A. M., et al., *Mol. Immunol.* 43 (12): 2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 1, e.g., SEQ ID NO: 14, 21, 28, 29, 32, 33, 34, 36, 37, 69, 70, 71, or 72, or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, 36, 37, 69, 70, 71, or 72, or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 1, e.g., SEQ ID NO: 14, 21, 28, 29, 32, 33, 34, or 36, or in some embodiments SEQ ID NO: 30, 31, 37, 69, 70, 71, 72, or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed. Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

In certain embodiments, a compstatin analog may be or comprise a cell-reactive compstatin analog. Cell-reactive compstatin analogs are compounds that comprise a compstatin analog moiety and a cell-reactive functional group that is capable of reacting with a functional group exposed at the surface of a cell, e.g., under physiological conditions, to form a covalent bond. The cell-reactive compstatin analog thus becomes covalently attached to the cell. Without wishing to be bound by any particular theory, a cell-tethered compstatin analog protects the cell from complement-mediated damage by, for example, binding to C3 (which may be in the form of $C3(H_2O)$) at the cell surface and/or in the vicinity of the cell and inhibiting C3 cleavage and activation, and/or by binding to C3b and inhibiting its deposition on the cell or participation in the complement activation cascade. In some aspects of the invention, isolated cells are contacted with a cell-reactive compstatin analog ex vivo (outside the body). In some aspects of the invention, the cells are present in an isolated tissue or organ, e.g., a tissue or organ to be transplanted into a subject. In some aspects of the invention, cells are contacted with a cell-reactive compstatin analog in vivo, by administering the cell-reactive compstatin analog to a subject. The cell-reactive compstatin analog becomes covalently attached to cells in vivo. In some aspects, the inventive approach protects cells, tissues, and/or organs from the deleterious effects of complement activation for at least two weeks, without need for retreatment during that time.

In some embodiments, the invention provides and/or utilizes compstatin analogs comprising a targeting moiety that binds non-covalently to a target molecule present at the surface of cells or tissues or to an extracellular substance not attached to cells or tissues. Such compstatin analogs are referred to herein as "targeted compstatin analogs"). Often the target molecule is a protein or carbohydrate attached to the cell membrane and exposed at the cell surface. The targeting moiety targets the compstatin analog to a cell, tissue, or location susceptible to complement activation. In some aspects of the invention, isolated cells are contacted with a targeted compstatin analog ex vivo (outside the body). In some aspects of the invention, the cells are present in an isolated tissue or organ, e.g., a tissue or organ to be transplanted into a subject. In some aspects of the invention, a targeted compstatin analog is administered to a subject and becomes non-covalently attached to a cell, tissue, or extracellular substance in vivo. In some aspects, the inventive approach protects cells, tissues, and/or organs from the deleterious effects of complement activation for at least two weeks, without need for retreatment during that time. In some embodiments, a targeted compstatin analog comprises both a targeting moiety and a cell-reactive moiety. The targeting moiety targets the compstatin analog, e.g., to a particular cell type, by binding non-covalently to a molecule on such cells. The cell-reactive moiety then binds covalently to the cell or extracellular substance. In other embodiments, a targeted compstatin analog does not comprise a cell-reactive moiety.

In some aspects, a compstatin analog may be or comprise a long-acting compstatin analog, wherein the long-acting compstatin analogs comprise a moiety such as polyethylene glycol (PEG) that prolongs the lifetime of the compound in the body (e.g., by reducing its clearance from the blood). In some embodiments, a long-acting compstatin analog does not comprise a targeting moiety or a cell-reactive moiety. In some embodiments, a long-acting compstatin analog comprises a targeting moiety and/or a cell-reactive moiety.

A compstatin analog, optionally linked to a cell-reactive moiety or targeting moiety, can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F.M. & Harris, Adv. Drug Deliv. Rev. 54, 453-456, 2002; Davis, F. F., Adv. Drug Deliv. Rev. 54, 457-458, 2002); Hinds, K. D. & Kim, S. W. *Adv. Drug Deliv. Rev.* 54, 505-530 (2002; Roberts, M. J., Bentley, M. D. & Harris, J. M. *Adv. Drug Deliv. Rev.* 54, 459-476; 2002); Wang, Y. S. et al. *Adv. Drug Deliv. Rev.* 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, CA, which also provides details of appropriate conjugation procedures. In another embodiment a compstatin analog is fused to the Fc domain of an immunoglobulin or a portion thereof. In some other embodiments a compstatin analog is conjugated to an albumin moiety or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, the compstatin analog comprises an amino acid having a side chain comprising a primary or secondary amine, e.g., a Lys residue. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. The spacer may, for example, comprise a substituted or unsubstituted, saturated or unsaturated alkyl chain, oligo (ethylene glycol) chain, and/or other moieties, e.g., as described herein with regard to linkers. The length of the chain may be, e.g., between 2 and 20 carbon atoms. In other embodiments the spacer is a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

(ii) Compstatin Mimetics

The structure of compstatin is known in the art, and NMR structures for a number of compstatin analogs having higher activity than compstatin are also known (Malik, supra). Structural information may be used to design compstatin mimetics.

In one embodiment, the compstatin mimetic is any compound that competes with compstatin or any compstatin analog (e.g., a compstatin analog whose sequence is set forth in Table 1) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure. In certain embodiments the compstatin mimetic is a compound that could substitute for a peptide having a sequence set forth in Table 1, e.g., SEQ ID NO: 14, 21, 28, 29, 32, 33, 34, or 36 or in certain embodiments SEQ ID NO: 30 or 31 or other compstatin analog sequence, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49:3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2 (5): 447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far. It will be appreciated that compstatin mimetics could be used in the cell-reactive compounds of the invention, and the invention provides such cell-reactive compstatin mimetics.

(iii) Cell-reactive or Long-Acting Compstatin Analogs

As noted above, in certain embodiments, the invention provides and/or utilizes a variety of cell-reactive compstatin analogs. In some aspects, a cell-reactive compstatin analog comprises a compound of formula A-L-M, wherein A is a moiety that comprises a cell-reactive functional group J, L is an optionally present linking portion, and M comprises a compstatin analog moiety. The compstatin analog moiety can comprise any compstatin analog, e.g., any compstatin analog described above, in various embodiments. Formula A-L-M encompasses embodiments in which A-L is present at the N-terminus of the compstatin analog moiety, embodiments in which A-L is present at the C-terminus of the compstatin analog moiety, embodiments in which A-L is attached to a side chain of an amino acid of the compstatin analog moiety, and embodiments where the same or different A-Ls are present at both ends of M. It will be appreciated that when certain compstatin analog(s) are present as a compstatin analog moiety in a compound of formula A-L-M, a functional group of the compstatin analog will have reacted with a functional group of L to form a covalent bond to A or L. For example, a cell-reactive compstatin analog in which the compstatin analog moiety comprises a compstatin analog that contains an amino acid with a side chain containing a primary amine ($NH_2$) group (which compstatin analog can be represented by formula $R^1$—($NH_2$)), can have a formula $R^1$—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compound described above. In some embodiments, a blocking moiety at the N-terminus or C-terminus of a compstatin analog, e.g., a compstatin analog described herein, is replaced by A-L in the structure of a cell-reactive compstatin analog. In some embodiments, A or L comprises a blocking moiety. In some embodiments, a cell-reactive compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a cell-reactive moiety. In some embodiments in which a cell-reactive compstatin analog comprises multiple compstatin analog moieties, the molar activity of the cell-reactive compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

Cell-reactive moiety A can comprise any of a variety of different cell-reactive functional groups J, in various embodiments. In general, a cell-reactive functional group may be selected based at least in part on factors such as (a) the particular functional group to be targeted; (b) the ability of the reactive functional group to react with the target functional group under physiologically acceptable ex vivo conditions (e.g., physiologically acceptable pH and osmolarity) and/or in vivo conditions (e.g., in blood); (c) the specificity of the reaction between the reactive functional group and the target functional group under physiologically acceptable ex vivo conditions and/or in vivo; (d) the stability (e.g., under in vivo conditions) of the covalent bond that would result from reaction of the reactive functional group with its target functional group; (e) the ease of synthesizing a cell-reactive compstatin analog comprising the reactive functional group, etc. In some embodiments, a reactive functional group that reacts with its target chemical group without releasing a leaving group is selected. In some embodiments, a reactive functional group that results in release of a leaving group upon reaction with a target is selected. Compounds containing such groups may be useful, e.g., to monitor progress and/or extent of a reaction. In some embodiments, a leaving group is physiologically acceptable to cells, tissues, or organs in the amount generated (e.g., based on concentration and/or absolute amount generated) and/or is medically acceptable to a subject in the amount generated in vivo (e.g., based on concentration in a relevant body fluid such as blood and/or based on the absolute amount generated). In some embodiments, a leaving group generated ex vivo is at least in part removed, e.g., by washing cells or by washing or perfusing a tissue or organ, e.g., with saline.

In many embodiments, a cell-reactive functional group of use in the invention reacts with a side chain of an amino acid residue and/or with an N-terminal amino group or C-terminal carboxyl group of a protein. In some embodiments, the cell-reactive functional group is reactive with sulfhydryl (—SH) groups, which are found in the side chains of cysteine residues. In some embodiments, a maleimide group is used. Maleimide groups react with sulfhydryl groups of cysteine residues of proteins at physiologic pH and form a stable thioether linkage. In some embodiments, a haloacetyl group, such as an iodoacetyl or a bromoacetyl group, is used. Haloacetyls react with sulfhydryl groups at physiologic pH. The reaction of the iodoacetyl group proceeds by nucleophilic substitution of iodine with a sulfur atom from a sulfhydryl group resulting in a stable thioether linkage. In other embodiments, an iodoacetamide group is used. In some embodiments, the cell-reactive functional group reacts with amino (—$NH_2$) groups, which are present at the N-termini of proteins and in the side chain of lysine residues (ε-amino group). In some embodiments an activated ester, e.g., a succinimidyl ester (i.e., NHS ester) is used. For example, N-hydroxysuccinimide (NHS) or its water-soluble analog (sulfo-NHS) can be used in the synthesis, whereby the resulting cell-reactive compstatin analog comprises an NHS ester. In some embodiments, the cell-reactive functional group reacts with carboxyl (—COOH) groups, which are present at the C-termini of proteins and in the side chains of various amino acid residues. In some embodiments, the cell-reactive compstatin analog is reactive with hydroxyl (—OH) groups, which are present in the side chains of various amino acids and in carbohydrate moieties of glycosylated proteins.

In general, linking portion L can comprise any one or more aliphatic and/or aromatic moieties consistent with the formation of a stable compound joining the linked moieties. The term "stable", as used herein, preferably refers to compounds which possess stability sufficient to allow manufacture and which maintain the integrity of the compound for a sufficient period of time, e.g., to be useful for one or more purposes described herein. In some embodiments, L comprises a saturated or unsaturated, substituted or unsubstituted, branched or unbranched, aliphatic chain having a length of between 1 and 30, between 1 and 20, between 1 and 10, between 1 and 6, or 5 or less carbon atoms, where length refers to the number of C atoms in the main (longest) chain. In some embodiments, the aliphatic chain comprises one or more heteroatoms (O, N, S), which may be independently selected. In some embodiments, at least 50% of the atoms in the main chain of L are carbon atoms. In some embodiments, L comprises a saturated alkyl moiety $(CH_2)$ n, wherein n is between 1 and 30.

In some embodiments, L comprises one or more heteroatoms and has a length of between 1 and 1000, between 1 and 800, between 1 and 600, between 1 and 400, between 1 and 300, between 1 and 200, between 1 and 100, between 1 and 50, between 1 and 30, or between 1 and 10 total carbon atoms in a chain. In some embodiments, L comprises an oligo (ethylene glycol) moiety $(—(O—CH_2—CH_2—)_n)$ wherein n is between 1 and 500, between 1 and 400, between 1 and 300, between 1 and 200, between 1 and 100, between 10 and 200, between 200 and 300, between 100 and 200, between 40 and 500, between 30 and 500, between 20 and 500, between 10 and 500, between 1 and 40, between 1 and 30, between 1 and 20, or between 1 and 10.

In some embodiments, L comprises an unsaturated moiety such as —CH═CH— or —$CH_2$—CH═CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(═O)—N—); an ester moiety (—CO—O—); a carbonyl moiety (—C(═O)—); an imine moiety (—C═N—); a thioether moiety (—C—S—C—); an amino acid residue; and/or any moiety that can be formed by the reaction of two compatible reactive functional groups. In certain embodiments, one or more moieties of a linking portion or cell-reactive moiety is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; Cl; Br; I; —NO2; —CN; —CF3; —CH2CF3; —CHC12; —CH2OH; —CH2CH2OH; —CH2NH2; —CH2SO2CH3; —or —GRG1 wherein G is —O—, —S—, —NRG2—, —C(═O)—, —S(═O)—, —SO2—, —C(═O)O—, —C(═O) NRG2—, —OC(═O)—, —NRG2C(═O)—, —OC(═O)O—, —OC(═O) NRG2—, —NRG2C(═O) O—, —NRG2C(═O) NRG2—, —C(═S)—, —C(═S) S—, —SC(═S)—, —SC(═S)S—, —C(═NRG2)—, —C(═NRG2)O—, —C(═NRG2) NRG3—, —OC (=NRG2)—, —NRG2C(=NRG3)—, —NRG2SO2—, —NRG2SO2NRG3—, or —SO2NRG2—, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the methods described herein, e.g., useful for the treatment of one or more disorders and/or for contacting a cell, tissue, or organ, as described herein, and/or useful as intermediates in the manufacture of one or more such compounds.

L can comprise one or more of any of the moieties described in the preceding paragraph, in various embodiments. In some embodiments, L comprises two or more different moieties linked to one another to form a structure typically having a length of between 1 to about 60 atoms, between 1 to about 50 atoms, e.g., between 1 and 40, between 1 and 30, between 1 and 20, between 1 and 10, or between 1 and 6 atoms, where length refers to the number of atoms in the main (longest) chain. In some embodiments, L comprises two or more different moieties linked to one another to form a structure typically having between 1 to about 40, e.g., between 1 and 30, e.g., between 1 and 20, between 1 and 10, or between 1 and 6 carbon atoms in the main (longest) chain. In general, the structure of such a cell-reactive compstatin analog can be represented by formula A-$(L^{Pj})$j-M, wherein j is typically between 1 and 10, and each $L^{Pj}$ is independently selected from among the moieties described in the preceding paragraph. In many embodiments, L comprises one or more carbon-containing chains such as —$(CH_2)$n- and/or —(O—$CH_2$—$CH_2$—)n, which are joined covalently to each other and/or to a cell-reactive functional group or compstatin analog, e.g., by moieties (e.g., amide, ester, or ether moieties) that result from the reaction of two compatible reactive functional groups. In some embodiments, L comprises an oligo (ethylene glycol) moiety and/or a saturated alkyl chain. In some embodiments, L comprises $(CH_2)_m$—C(═O)—NH—$(CH_2CH_2O)_n(CH_2)_p$C(═O)— or —$(CH_2)_m$—C(═O)—NH—$(CH_2)_p(OCH_2CH_2)_n$C(═O)—. In some embodiments, m, n, and p are selected so that the number of carbons in the chain is between 1 and 500, e.g., between 2 and 400, between 2 and 300, between 2 and 200, between 2 and 100, between 2 and 50, between 4 and 40, between 6 and 30, or between 8 and 20. In some embodiments, m is between 2 and 10, n is between 1 and 500, and/or p is between 2 and 10. In some embodiments, m is between 2 and 10, n is between 1 and 400, and/or p is between 2 and 10. In some embodiments, m is between 2 and 10, n is between 1 and 300, and/or p is between 2 and 10. In some embodiments, m is between 2 and 10, n is between 1 and 200, and/or p is between 2 and 10. In some embodiments, m is between 2 and 10, n is between 1 and 100, and/or p is between 2 and 10. In some embodiments, m is between 2 and 10, n is between 1 and 50, and/or p is between 2 and 10. In some embodiments, m is between 2 and 10, n is between 1 and 25, and/or p is between 2 and 10. In some embodiments, m is between 2 and 10, n is between 1 and 8, and/or p is between 2 and 10. Optionally, at least one —$CH_2$— is replaced by CH—R, wherein R can be any substituent. Optionally, at least one —$CH_2$— is replaced by a heteroatom, cyclic ring system, amide, ester, or ether moiety. In some embodiments, L does not comprise an alkyl group having more than 3 carbon atoms in the longest chain. In some embodiments, L does not comprise an alkyl group having more than 4, 5, 6, 7, 8, 9, 10, or 11 carbon atoms in the longest chain.

In some embodiments of the invention, A comprises a cell-reactive functional group J and a linker $L^1$ comprising a linking portion $L^{P1}$ and a reactive functional group that reacts with the compstatin analog to generate A-M In some embodiments, a bifunctional linker $L^2$ comprising two reactive functional groups and a linking portion $L^{P2}$ is used. The reactive functional groups of L react with appropriate reactive functional groups of A and M to produce a cell-reactive compstatin analog A-L-M. In some embodiments, the compstatin analog comprises a linker $L^3$ comprising a linking portion $L^{P3}$. For example, as discussed below, a linker comprising a reactive functional group may be present at the N- or C-terminus or a moiety comprising a reactive functional group may be attached to the N- or C-terminus via a linker. Thus L may contain multiple linking portions LP contributed, e.g., by A, by linker(s) used to join A and M, and/or by the compstatin analog. It will be understood that, when present in the structure A-L-M, certain reactive functional group(s) present prior to reaction in $L^1$, $L^2$, $L^3$, etc., will have undergone reaction, so that only a portion of said reactive functional group(s) will be present in the final structure A-L-M, and the compound will contain moieties formed by reaction of said functional groups. In general, if a compound contains two or more linking portions, the linking portions can be the same or different, and can be independently selected in various embodiments. Multiple linking portions LP can be attached to one another to form a larger linking portion L, and at least some of such linking portions can have one or more compstatin analog(s) and/or cell-reactive functional group(s) attached thereto. In molecules comprising multiple compstatin analogs, the compstatin analogs can be the same or different and, if different, can be independently selected. The same applies to the linking portions and reactive functional groups. The invention encompasses the use of multivalent compstatin analogs comprising one or more cell-reactive functional group(s) and use of concatamers of compstatin analogs comprising one or more cell-reactive functional group(s). In some embodiments, at least one linkage is a stable non-covalent linkage such as a biotin/(strept) avidin linkage or other noncovalent linkage of approximately equivalent strength.

In some embodiments a cell-reactive compstatin analog comprises a compstatin analog in which any of SEQ ID NOs: 3-36, 69, 70, 71, or 72 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring. In some embodiments, the amino acid(s) is/are L-amino acids. In some embodiments, any one or more of the amino acid(s) is a D-amino acid. If multiple amino acids are added, the amino acids can be independently selected. In some embodiments, the reactive functional group (e.g., a primary or secondary amine) is used as a target for addition of a moiety comprising a cell-reactive functional group. Amino acids having a side chain that comprises a primary or secondary amine include lysine (Lys) and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry, Volumes* 1-4, Wiley-VCH (2009-2011); Blaskovich, M., Handbook on Syntheses of Amino Acids General Routes to Amino Acids, Oxford University Press, 2010. The invention encompasses embodiments in which one or more non-standard amino acid(s) is/are used to provide a target for addition of a moiety comprising a cell-reactive functional group. Any one or more of the amino acid(s) may be protected as appropriate during synthesis of the compound. For example, one or more amino acid(s) may be protected during reaction(s) involving the target amino acid side chain. In some embodiments, wherein a sulfhydryl-containing amino acid is used as a target for addition of a moiety comprising a cell-reactive functional group, the sulfhydryl is protected while the compound is being cyclized by formation of an intramolecular disulfide bond between other amino acids such as cysteines.

In the discussion in this paragraph, an amino acid having a side chain containing an amine group is used as an example. The invention encompasses analogous embodiments in which an amino acid having a side chain containing a different reactive functional group is used. In some embodiments, an amino acid having a side chain comprising a primary or secondary amine is attached directly to the N-terminus or C-terminus of any of SEQ ID NOs: 3-36, 37, 69, 70, 71, or 72 or via a peptide bond. In some embodiments, an amino acid having a side chain comprising a primary or secondary amine is attached to the N- or C-terminus of any of SEQ ID NOs: 3-36, 37, 69, 70, 71, or 72, or via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein. Thus in some embodiments, a cell-reactive compstatin analog comprises a compstatin analog moiety M of formula B1-R1-M1-R2-B2, wherein $M_1$ represents any of SEQ ID NOs: 3-36, 37, 69, 70, 71, or 72, either R1 or R2 may be absent, at least one of R1 and R2 comprises an amino acid having a side chain that contains a primary or secondary amine, and B1 and B2 are optionally present blocking moieties. R1 and/or R2 may be joined to $M_1$ by a peptide bond or a non-peptide bond. R1 and/or R2 may comprise a linking portion $L^{P3}$. For example, R1 can have formula $M_2$-$L^{P3}$ and/or R2 can have formula $L^{P3}$-$M_2$ wherein $L^{P3}$ is a linking portion, and $M_2$ comprises at least one amino acid having a side chain comprising a primary or secondary amine. For example, $M_2$ can be Lys or an amino acid chain comprising Lys. In some embodiments, $L^{P3}$ comprises of consists of one or more amino acids. For example, $L^{P3}$ can be between 1 and about 20 amino acids in length, e.g., between 4 and 20 amino acids in length. In some embodiments, $L^{P3}$ comprises or consist of multiple Gly, Ser, and/or Ala residues. In some embodiments, $L^{P3}$ does not comprise an amino acid that comprises a reactive SH group, such as Cys. In some embodiments, $L^{P3}$ comprises an oligo (ethylene glycol) moiety and/or a saturated alkyl chain. In some embodiments, $L^{P3}$ is attached to the N-terminal amino acid of $M_1$ via an amide bond. In some embodiments, $L^{P3}$ is attached to the C-terminal amino acid of $M_1$ via an amide bond. The compound may be further extended at either or both termini by addition of further linking portion(s) and/or amino acid(s). The amino acids can the same or different and, if different, can be independently selected. In some embodiments, two or more amino acids having side chains comprising reactive functional groups are used, wherein the reactive functional groups can be the same or different. The two or more reactive functional groups can be used as targets for addition of two or more moieties. In some embodiments, two or more cell-reactive moieties are added. In some embodiments, a cell-reactive moiety and a targeting moiety are added. In some embodiments, a linker and/or cell-reactive moiety is attached to an amino acid side chain after incorporation of the amino acid into a peptide chain. In some embodiments, a linker and/or cell-reactive moiety is already attached to the amino acid side chain prior to use of the amino acid in the synthesis of a cell-reactive compstatin analog. For example, a Lys derivative having a linker attached to its side chain can be used. The linker may comprise a cell-reactive functional group or may subsequently be modified to comprise a cell-reactive functional group.

Certain cell-reactive compstatin analogs are described in further detail below. In the following discussion, a peptide having the amino acid sequence Ile-Cys*-Val-(1Me) Trp-Gln-Asp-Trp-Gly-Ala-His-Arg-Cys*-Thr (SEQ ID NO: 37) (corresponding to the compstatin analog of SEQ ID NO: 28, wherein asterisks in SEQ ID NO: 37 represent cysteines joined by a disulfide bond in the active compound, and (1Me) Trp represents 1-methyl-tryptophan)), is used as an exemplary compstatin analog moiety; maleimide (abbreviated Mal) is used as an example of a cell-reactive functional group; $(CH2)_n$ and $(O—CH2—CH2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and are represented in italics, i.e., as Ac and $NH_2$ respectively. It will be appreciated that the compounds can be prepared using a variety of synthetic approaches and using a variety of precursors. The discussion of various synthetic approaches and precursors below is not intended to limit the invention.

In general, any of the features of any of the compounds described below or herein can be freely combined with feature(s) of other compounds described below or elsewhere herein, and the invention encompasses such embodiments.

In some embodiments, the cell-reactive moiety is provided by a cell-reactive compound comprising a maleimide group (as a cell-reactive functional group) and an alkanoic acid (RCOOH), where R is an alkyl group. For example, 6-malemeidocaproic acid (Mal-$(CH_2)_5$—COOH), depicted below, can be used.

Compound I

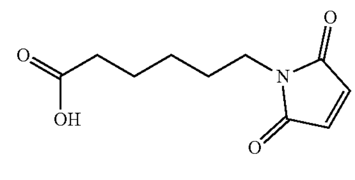

In some embodiments, the cell-reactive moiety is provided by a derivative of an alkanoic acid in which the carboxylic acid moiety has been activated, e.g., the OH moiety has been converted to a better leaving group. For example, the carboxyl group of compound I may be reacted with EDC, followed by reaction with NHS (which can optionally be provided as water-soluble sulfo-NHS), resulting in an N-hydroxysuccinimide ester derivative of 6-malemeidocaproic acid, i.e., 6-maleimidohexanoic acid N-hydroxysuccinimide (NHS) ester (depicted below).

Compound II

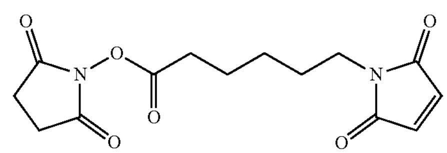

The compound of SEQ ID NO: 37 can be modified at the N- and/or C-terminus to generate a cell-reactive compstatin analog. For example, compound II can be used to generate the following cell-reactive compstatin analog by reaction with the N-terminal amino group of Ile.

Maleimide-$(CH_2)_5$—C(═O)—Ile-Cys*-Val-(1Me) Trp-Gln-Asp-Trp-Gly-Ala-His-Arg-Cys*-Thr-$NH_2$ (SEQ ID NO: 38). It will be appreciated that in SEQ ID NO: 38 the-C(═O) moiety is attached to the immediately C-terminal amino acid (Ile), via a C—N bond, wherein the N is part of the amino acid and is not shown.

In other embodiments, a maleimide group is linked to Thr at the C-terminus, resulting in the following cell-reactive compstatin analog:

(SEQ ID NO: 39)
Ac-Ile-Cys*-Val-(1Me)Trp-Gln-Asp-Trp-Gly-Ala-

His-Arg-Cys*-Thr-(C═O)-$(CH_2)_5$-maleimide.

In some embodiments, a cell-reactive compstatin analog can be synthesized using bifunctional linker (e.g., a heterobifunctional linker). An exemplary heterobifunctional linker comprising $(CH_2—CH_2—O)_n$ and $(CH_2)_m$ (where m=2) moieties is shown below:

Compound III

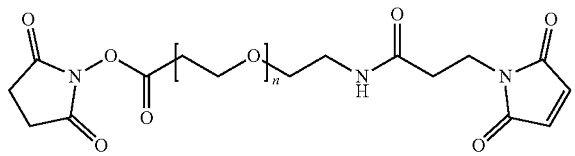

Compound III comprises a maleimide group as a cell-reactive functional group and an NHS ester moiety that reacts readily with an amino group (e.g., an N-terminal amino group or an amino group of an amino acid side chain).

An embodiment of compound III in which n=2 can be used to generate the following cell-reactive compstatin analog using the compstatin analog of SEQ ID NO: 37:

(SEQ ID NO: 40)

Maleimide- $(CH_2)_2$—C(═O)—NH—$CH_2CH_2OCH_2CH_2OCH_2CH_2$C(═O)-Ile-

-continued

Cys*-Val-(1Me)Trp-Gln-Asp-Trp-Gly-Ala-His-Arg-

Cys*-Thr-$NH_2$

It will be appreciated that in the compound of SEQ ID NO: 40 a —C(═O) moiety is attached to the N-terminal amino acid (Ile residue via a C—N bond, wherein the N is part of the amino acid and is not shown. In some embodiments a linker has the formula of Compound III wherein n≥1. Exemplary values for n in a $(CH_2—CH_2—O)_n$ moiety are provided herein.

In some embodiments, the alkyl chain that links the maleimide moiety to the rest of the molecule contains more or fewer methylene units, the oligo (ethylene glycol) moiety contains more or fewer ethylene glycol units, and/or there are more or fewer methylene units flanking either or both sides of the oligo (ethylene glycol) moiety, as compared with the compound of SEQ ID NO: 39 or SEQ ID NO: 40. Exemplary cell-reactive compstatin analogs illustrative of a few such variations are presented below (SEQ ID NOs: 41-46):

(SEQ ID NO: 41)

Maleimide-$(CH_2)_2$—C(═O)—NH—$CH_2CH_2OCH_2CH_2$C(═O)-

Ile-Cys*-Val-(1Me)Trp-Gln-Asp-Trp-Gly-Ala-His-

Arg-Cys*-Thr-$NH_2$ (SEQ ID NO: 42)

Maleimide- $(CH_2)_3$—C(═O)—NH—$CH_2CH_2OCH_2CH_2OCH_2$C(═O)-Ile-Cys*-

Val-(1Me)Trp-Gln-Asp-Trp-Gly-Ala-His-Arg-Cys*-

Thr-$NH_2$ (SEQ ID NO: 43)

Maleimide- $(CH_2)_5$—C(═O)—NH—$CH_2CH_2OCH_2CH_2OCH_2$C(═O)-Ile-Cys*-

Val-(1Me)Trp-Gln-Asp-Trp-Gly-Ala-His-Arg-Cys*-

Thr-$NH_2$ (SEQ ID NO: 44)

Maleimide- $(CH_2)_4$—C(═O)—NH—$CH_2CH_2OCH_2CH_2OCH_2CH_2$C(═O)-Ile-

Cys*-Val-(1Me)Trp-Gln-Asp-Trp-Gly-Ala-His-Arg-

Cys*-Thr-$NH_2$ (SEQ ID NO: 45)

Maleimide- $(CH_2)_2$—C(═O)—NH—$CH_2CH_2OCH_2CH_2OCH_2CH_2$C(═O)-Ile-

Cys*-Val-(1Me)Trp-Gln-Asp-Trp-Gly-Ala-His-Arg-

Cys*-Thr-$NH_2$ (SEQ ID NO: 46)

Maleimide- $(CH_2)_5$—C(═O)—NH—$CH_2CH_2OCH_2CH_2OCH_2$C(═O)-Ile-Cys*-

Val-(1Me)Trp-Gln-Asp-Trp-Gly-Ala-His-Arg-Cys*-

Thr-$NH_2$

In some embodiments, SEQ ID NO: 37 is extended to comprise a Lys residue at the N- or C-terminus of the peptide, e.g., as exemplified below for a C-terminal linkage:

(SEQ ID NO: 47)
Ac-Ile-Cys*-Val-(1Me)Trp-Gln-Asp-Trp-Gly-Ala-His-Arg-Cys*-Thr-Lys-$NH_2$.

In some embodiments, a Lys residue is attached to the N- or C-terminus of SEQ ID NO: 37 via a peptide linker, e.g., as exemplified below for a C-terminal linkage:

(SEQ ID NO: 48)
Ac-Ile-Cys*-Val-(1Me)Trp-Gln-Asp-Trp-Gly-Ala-His-Arg-Cys*-Thr-$(Gly)_5$-Lys-$NH_2$.

In some embodiments, a linker comprising a primary or secondary amine is added to the N- or C-terminus of a compstatin analog. In some embodiments, the linker comprises an alkyl chain and/or an oligo (ethylene glycol) moiety. For example, $NH_2(CH_2CH_2O)nCH_2C(=O)OH$ (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 11-amino-3,6,9-trioxaundecanoic acid), can be used. In some embodiments, the resulting compound is as follows (wherein the portion contributed by the linker is shown in bold):

(SEQ ID NO: 49)
NH2(CH2)5C(=O)-Ile-Cys-Val-(1Me)Trp-Gln-Asp-Trp-Gly-Ala-His-Arg-Cys-Thr-$NH_2$ (SEQ ID NO: 50)
NH2(CH2CH2O)2CH2C(=O)-Ile-Cys-Val-(1Me)Trp-Gln-Asp-Trp-Gly-Ala-His-Arg-Cys-Thr-$NH_2$

In some embodiments, a Lys residue is attached to the N- or C-terminus of SEQ ID NO: 37 via a linker comprising a non-peptide portion. For example, the linker can comprise an alkyl chain, oligo (ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

(SEQ ID NO: 51)
Ac-Ile-Cys*-Val-(1Me)Trp-Gln-Asp-Trp-Gly-Ala-His-Arg-Cys*-Thr-NH-CH2CH2OCH2CH2OCH2—C(=O)-Lys-$NH_2$

It will be appreciated that in SEQ ID NOs: 49 and 50, a —C(=O) moiety is attached to the adjacent Ile residue via a C—N bond, wherein the N is part of the amino acid and is not shown. Similarly, in SEQ ID NO: 51, a —C(=O) moiety is attached to the adjacent Lys residue via a C—N bond, wherein the N is part of the amino acid and is not shown. It will also be appreciated that that in SEQ ID NO: 51 the NH moiety is attached to the immediately N-terminal amino acid (Thr), via a C—N bond, wherein the C is the carbonyl carbon of the amino acid and is not shown.

The compounds of SEQ ID NOs: 47-51 can readily be modified at the primary amine group to produce a cell-reactive compstatin analog. For example, the compounds of SEQ ID NOs: 47-51 (or other compounds comprising a primary or secondary amine and a compstatin analog moiety) can be reacted with 6-maleimidocaproic acid N-succinimidyl ester to produce the following cell-reactive compstatin analogs:

(SEQ ID NO: 52)
Ac-Ile-Cys*-Val-(1Me)Trp-Gln-Asp-Trp-Gly-Ala-His-Arg-Cys*-Thr-Lys-(C(=O)—$(CH_2)_5$-Mal)-$NH_2$.

(SEQ ID NO: 53)
Ac-Ile-Cys*-Val-(1Me)Trp-Gln-Asp-Trp-Gly-Ala-His-Arg-Cys*-Thr-$(Gly)_5$-Lys-(C(=O)—$(CH_2)_5$-Mal)-$NH_2$.

(SEQ ID NO: 54)
Mal-$(CH_2)_5$—(C(=O)—NH(CH2)5C(=O)-Ile-Cys-Val-(1Me)Trp-Gln-Asp-Trp-Gly-Ala-His-Arg-Cys-Thr-$NH_2$ (SEQ ID NO: 55)
Mal-$(CH_2)_5$—(C(=O)NH(CH2CH2O)2CH2C(=O)-Ile-Cys-Val-(1Me)Trp-Gln-Asp-Trp-Gly-Ala-His-Arg-Cys-Thr-$NH_2$ (SEQ ID NO: 56)
Ac-Ile-Cys*-Val-(1Me)Trp-Gln-Asp-Trp-Gly-Ala-His-Arg-Cys*-Thr-NH—CH2CH2OCH2CH2OCH2—C(=O)-Lys-(C(=O)—$(CH_2)_5$-Mal)-$NH_2$

In another embodiment, a cell-reactive compstatin analog is represented as:

(SEQ ID NO: 57)
Cys*-Val-(1Me)Trp-Gln-Asp-Trp-Gly-Ala-His-Arg-Cys*-Thr-Lys-C(=O)—$CH_2(OCH_2CH_2)_2NH$(C(=O)—$(CH_2)_5$-Mal)-$NH_2$.

The invention provides variants of SEQ ID NOs: 38-57 in which-Ile-Cys*-Val-(1Me) Trp-Gln-Asp-Trp-Gly-Ala-His-Arg-Cys*-Thr- is replaced by an amino acid sequence comprising the amino acid sequence of any other compstatin analog, e.g., of any of SEQ ID NOs 3-27, 29-36, 37, 69, 70, 71, or 72 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Other bifunctional cross-linkers comprising a maleimide as a cell-reactive moiety and an NHS ester as an amine-reactive moiety of use in various embodiments of the invention include, e.g., succinimidyl 4-(p-maleimidophenyl) butyrate (SMPB); succinimidyl 4-(N-maleimidomethyl)-cyclohexane-1-carboxylate (SMCC); N-γ-maleimidobutyryl-oxysuccinimide ester (GMBS). Addition of a sulfonate to the NHS ring results in water-soluble analogs such as sulfo-succinimidyl (4-iodoacetyl)-aminobenzoate (sulfo-SIAB), sulfo-succinimidyl 4-(N-maleimidomethyl)-cyclohexane-1-carboxylate (sulfo-SMCC), sulfo-succinimidyl 4-(p-maleimidophenyl) butyrate (sulfo-SMPB), sulfo-N-γ-maleimidobutyryl-oxysuccinimide ester (sulfo-GMBS) etc., which can avoid the need for an organic solvent. In some embodiments, a long chain version of any of the foregoing, comprising a spacer arm between the NHS ester moiety and the remainder of the molecule, is used. The spacer can comprise, e.g., an alkyl chain. An example is succinimidyl-4-[N-Maleimidomethyl]cyclohexane-1-carboxy-[6-amido-caproate].

In some embodiments, a bifunctional linker comprising an NHS ester (as an amine-reactive moiety) and an iodoacetyl group (reactive with sulfhydryl groups) is used. Such linkers include, e.g., N-succinimidyl (4-iodoacetyl)-aminobenzoate (SIAB); succinimidyl 6-[(iodoacetyl)-amino] hexanoate (SIAX); succinimidyl 6-[6-(((iodoacetyl)amino)-hexanoyl) amino]hexanoate (SIAXX); succinimidyl 4-((iodoacetyl)amino)methyl)-cyclohexane-1 -carboxylate (SIAC); and succinimidyl 6-((((4-(iodoacetyl)amino) methyl-cyclohexane-1-carbonyl)amino) hexanoate (SIACX).

In some embodiments, a bifunctional linker comprising an NHS ester (as an amine-reactive moiety) and a pyridy disulfide group (as a cell-reactive moiety reactive with sulfhydryl groups) is used. Examples include N-succinimidyl 3-(2-pyridyldithio) propionate (SPDP); succinimidyloxycarbonyl-α-methyl-α-(2-pyridyldithio) toluene (SMPT) and versions comprising a sulfonate on the NHS ring and/or a spacer comprising an alkyl chain between the NHS ester moiety and the rest of the molecule (e.g., succinimidyl 6-(3-[2-pyridyldithio]-propionamido) hexanoate) (LC-SPDP). Variations of such linkers that include additional or different moieties could be used. For example, a longer or shorter alkyl chain could be used in a spacer, or an oligo (ethylene glycol) moiety instead of an alkyl chain.

In general, a cell-reactive compstatin analog can be synthesized using a variety of approaches. Cell-reactive compounds that comprise a cell-reactive functional group and a linker can often be purchased as preformed building blocks. For example, 6-malemeidocaproic acid and 6-maleimidocaproic acid N-hydroxysuccinimide ester can be purchased from various suppliers. Alternately, such compounds can be synthesized using methods known in the art. See, e.g., Keller O, Rudinger J. Helv Chim Acta. 58 (2): 531-41, 1975 and Hashida S, et al., J Appl Biochem., 6 (1-2): 56-63, 1984. See also, Hermanson, G. supra, and references therein, for discussion of methods and reagents of use for synthesizing conjugates. In general, the invention encompasses any method of producing a compound comprising a compstatin analog moiety and a cell-reactive functional group, and the resulting compounds.

In some embodiments, an amino acid having a linker attached to a side chain is used in the synthesis of a linear peptide. The linear peptide can be synthesized using standard methods for peptide synthesis known in the art, e.g., standard solid-phase peptide synthesis. The linear peptide is then cyclized (e.g., by oxidation of the Cys residues to form an intramolecular disulfide). The cyclic compound may then be reacted with a linker comprising a cell-reactive functional group. In other embodiments, a moiety comprising a cell-reactive functional group is reacted with a linear compound prior to cyclization thereof. In general, reactive functional groups can be appropriately protected to avoid undesired reaction with each other during synthesis of a cell-reactive compstatin analog. The cell-reactive functional group, any of the amino acid side chains, and/or either or both termini of the peptide may be protected during the reaction and subsequently deprotected. For example, SH groups of Cys residues and/or SH-reactive moieties such as maleimides can be protected until after cyclization to avoid reaction between them. The reaction conditions are selected based at least in part on the requirements of the particular reactive functional group(s) to achieve reasonable yield in a reasonable time period. Temperature, pH, and the concentration of the reagents can be adjusted to achieve the desired extent or rate of reaction. See, e.g., Hermanson, supra. The desired product can be purified, e.g., to remove unreacted compound comprising the cell-reactive functional group, unreacted compstatin analog, linker(s), products other than the desired cell-reactive compstatin analog that may have been generated in the reaction, other substances present in the reaction mixture, etc. Compositions and methods for making the cell-reactive compstatin analogs, and intermediates in the synthesis, are aspects of the invention.

In some aspects of the invention, linker(s) described above are used in the production of compstatin analogs comprising a moiety such as a polyethylene glycol (PEG) chain or other polymer(s) that, e.g., stabilize the compound, increase its lifetime in the body, increase its solubility, decrease its immunogenicity, and/or increase its resistance to degradation. Without limiting the invention in any way, such a moiety may be referred to herein as a "clearance reducing moiety" (CRM), and a compstatin analog comprising such a moiety may be referred to as a "long-acting compstatin analog" (LACA). In some embodiments, a long-acting compstatin analog has an average plasma half-life of at least 1 day, e.g., 1-3 days, 3-7 days, 7-14 days, or 14-28 days, when administered IV at a dose of 10 mg/kg to humans or to non-human primates, or a dose of about 1-3 mg/kg, 3-5 mg/kg, 5-10 mg/kg, e.g., 7 mg/kg. In some embodiments, a long-acting compstatin analog has an average plasma half-life of at least 1 day, e.g., 1-3 days, 3 7 days, 7-14 days, or 14-28 days, when administered subcutaneously at, e.g., a dose of about 1-3 mg/kg, 3-5 mg/kg, 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5, 5.5, 6, 6.5, 7, 7.5, 8, 8.5, 9, 9.5 or 10 days when administered intravenously at, e.g., a dose of about 1-3 mg/kg, 3-5 mg/kg, or 5-10 mg/kg, e.g., 7 mg/kg to humans or to non-human primates. In some embodiments, a long-acting compstatin analog has an average plasma half-life (e.g., a terminal half-life) of between about 4-10, 5-9, 5-8, 6-9, 7-9, or 8-9 days, e.g., about 4, 4.5, 5, 5.5, 6, 6.5, 7, 7.5, 8, 8.5, 9, 9.5 or 10 days, when administered subcutaneously at, e.g., a dose of about 1-3 mg/kg, 3-5 mg/kg, 5-10 mg/kg, e.g., 7 mg/kg to humans or to non-human primates. In certain embodiments a long-acting compstatin analog is characterized in that it is extensively absorbed from the site of administration during the time period following subcutaneous injection and provides, e.g., at or after about 1-2 days following administration, a blood level comparable to that which would be achieved had the same amount of compound been administered intravenously instead. In some embodiments, the blood level at or after about 2, 3, 4, 5, 6, 7, 8, or more days following administration of a subcutaneous dose is within about 5%, 10%, 15%, 20%, or 25% of the blood level which would be achieved had the same amount of compound been administered intravenously instead. In some embodiments, average plasma half-life of a long-acting compstatin analog following administration IV at a dose of 10 mg/kg to humans or to non-human primates is increased by at least a factor of 2, e.g., by a factor of 2-5, 5-10, 10-50, or 50-100-fold or 100-150-fold or 150-200 fold as compared with that of a corresponding compstatin analog having the same amino acid sequence (and, if applicable, one or more blocking moiet(ies)) but not comprising the CRM. It will be understood that in various embodiments such an increase in half-life may be observed following administration via other routes such as subcutaneous administration and/or using other doses, e.g., other doses described herein, e.g., 20 mg/kg.

As noted above, in some embodiments a compstatin analog of any of SEQ ID NOs: 3-36, 37, 69, 70, 71, or 72 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring, which facilitate conjugation with a reactive functional group to attach a CRM to the compstatin analog. It will be understood that a corresponding compstatin analog not comprising the CRM may also lack one or more such amino acids which are present in the long-acting compstatin analog to which it corresponds. Thus, a corresponding compstatin analog comprising any of SEQ ID NOs: 3-36, 37, 69, 70, 71, or 72 and lacking a CRM will be understood to "have the same amino acid sequence" as SEQ ID NO: 3-36, 37, 69, 70, 71, or 72, respectively. For example, a corresponding compstatin analog comprising the amino acid sequence of SEQ ID NO: 14, 21, 28, 29, 32, 33, 34, or 36 and lacking a CRM will be understood to "have the same amino acid sequence" as SEQ ID NO: 14, 21, 28, 29, 32, 33, 34, or 36, respectively.

In some embodiments, a plasma half-life is a terminal half-life after administration of a single IV dose. In some embodiments, a plasma half-life is a terminal half-life after steady state has been reached following administration of multiple IV doses. In some embodiments, a long-acting compstatin analog achieves a Cmax in plasma at least 5-fold as great as that of a corresponding compstatin analog not comprising the CRM, e.g., between 5- and 50-fold as great, following administration of a single IV dose to a primate, or following administration of multiple IV doses. In some embodiments, a long-acting compstatin analog achieves a Cmax in plasma between 10- and 20-fold as great as that of a corresponding compstatin analog not comprising the CRM following administration of a single IV dose to a primate, or following administration of multiple IV doses.

In some embodiments a primate is human. In some embodiments a primate is a non-human primate, e.g., a monkey, such as a Cynomolgus monkey or Rhesus monkey.

In some embodiments, renal clearance of a long-acting compstatin analog during the first 24 hours following administration IV at a dose of 10 mg/kg or 20 mg/kg to humans or to non-human primates is reduced by at least a factor of 2, e.g., by a factor of 2-5, 5-10, 10-50, or 50-100-fold or 100-150-fold or 150-200 fold as compared with renal clearance of a corresponding compstatin analog. It will be understood that in various embodiments such a reduction in renal clearance may be observed following administration via other routes such as subcutaneous administration and/or using other doses, e.g., other doses described herein, e.g., 20 mg/kg.

The concentration of compstatin analog can be measured in blood and/or urine samples using, e.g., UV, HPLC, mass spectrometry (MS) or antibody to the CRM, or combinations of such methods, such as LC/MS or LC/MS/MS. Pharmacokinetic parameters such as half-life and clearance can be determined using methods known to those of ordinary skill in the art. Pharmacokinetic analysis can be performed, e.g., with WinNonlin software v 5.2 (Pharsight Corporation, St. Louis, MO) or other suitable programs.

In certain embodiments a CRM is stable in physiological conditions for at least 24 hours or more. In certain embodiments a CRM is stable in mammalian, e.g., primate, e.g., human or non-human primate (e.g., monkey) blood, plasma, or serum for at least 24 hours. In various embodiments at least 50%, 60%, 70%, 80%, 90%, 95%, 96%, 97%, 98%, 99%, or more, of the CRM molecules remains intact upon incubation in physiological conditions for 24 hours, 48 hours, 72 hours, 96 hours, 120 hours, 144 hours, 168 hours, or more. In various embodiments at least 50%, 60%, 70%, 80%, 90%, 95%, 96%, 97%, 98%, 99%, or more, of the CRM molecules remains intact upon incubation in blood, plasma, or serum at 37 degrees C. for 48 hours, 72 hours, 96 hours, 120 hours, 144 hours, 168 hours, or more. Incubation may be performed using a CRM at a concentration of between 1 microgram/ml to about 100 mg/ml in various embodiments. Samples may be analyzed at various time points. Size or intactness may be assessed using, e.g., chromatography (e.g., HPLC), mass spectrometry, Western blot, or any other suitable method. Such stability characteristics may be conferred on a moiety conjugated to the CRM. In various embodiments, a long-acting compstatin analog comprising a CRM may have any of the afore-mentioned stability characteristics. In some aspects intact with regard to a long-acting compstatin analog means that the compstatin analog moiety remains conjugated to the CRM and the CRM size remains about the same as at the start of incubation or administration.

In some embodiments, a long-acting compstatin analog has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CRM. In some embodiments wherein a long-acting compstatin analog comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties.

In some embodiments, a polyethylene glycol (PEG) comprises a $(CH_2CH_2O)_n$ moiety having a molecular weight of at least 500 daltons.

In some embodiments, a linker described above comprises an $(CH_2CH_2O)_n$ moiety having an average molecular weight of about 500; 1,000; 1,500; 2,000; 5,000; 10,000; 20,000; 30,000; 40,000; 50,000; 60,000; 70,000; 80,000; 90,000; and 100,000 daltons.

In some embodiments the average molecular weight of a PEG is at least 20,000 daltons, up to about 100,000; 120,000; 140,000; 160,000; 180,000; or 200,000 daltons. "Average molecular weight" refers to the number average molecular weight. In some embodiments, the polydispersity D of a $(CH_2CH_2O)_n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)n$ moiety is monodisperse and the polydispersity of a $(CH_2CH_2O)n$ moiety is 1.0. Such monodisperse $(CH_2CH_2O)_n$ moieties are known in the art and are commercially available from Quanta BioDesign (Powell, OH), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)_n$ moieties is between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)_n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments the average total molecular weight of the compound or $(CH_2CH_2O)_n$ moieties is at least 20,000 daltons, up to about 100,000; 120,000; 140,000; 160,000; 180,000; or 200,000 daltons. In some embodiments n is between about 30 and about 3000.

In some embodiments a compstatin analog moiety is attached at each end of a linear PEG. A bifunctional PEG having a reactive functional group at each end of the chain may be used, e.g., as described above. In some embodiments the reactive functional groups are identical while in some embodiments different reactive functional groups are present at each end.

In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)_n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a long-acting compstatin analog thus may comprise, e.g., 3-10 compstatin analog moieties, e.g., 4-8 compstatin analog moieties, each attached to a $(CH_2CH_2O)_n$ chain via a functional group at the end of the chain. In some embodiments a long-acting compstatin analog may comprise, e.g., 10-100 compstatin analog moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a compstatin analog moiety attached thereto. In some embodiments at least about 30%, 40%, 50%, 60%, 70%, 80%, 90%, 95%, or 100% of the chains has a compstatin analog moiety attached thereto.

In general and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group ($OCH_3$) but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A $R^1O—(CH_2CH_2O)_n—T—$ Reactive functional group wherein "Reactive functional group" and n are as defined above and described in classes and subclasses herein;

R1 is hydrogen, aliphatic, or any suitable end group; and

T is a covalent bond or a C1-12 straight or branched, hydrocarbon chain wherein one or more carbon units of T are optionally and independently replaced by —O—, —S—, —$N(R^x)$—, —C(O)—, —C(O)O—, —OC(O)—, —$N(R^x)C(O)$—, —$C(O)N(R^x)$—, —S(O)—, —$S(O)_2$—, —$N(R^x)SO_2$—, or —$SO_2N(R^x)$—; and each $R^x$ is independently hydrogen or $C_{1-6}$ aliphatic.

Exemplary monofunctional PEGs of formula A include:

Formula I

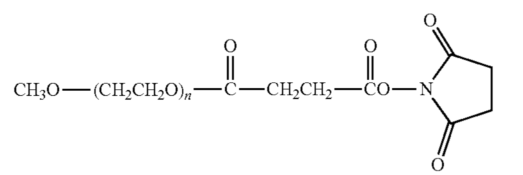

In Formula I, the moiety comprising the reactive functional group has the general structure —CO—$(CH_2)_m$—COO—NHS, where m=2. In some embodiments, a monofunctional PEGs has the structure of Formula I, where m is between 1 and 10, e.g., between 1 and 5. For example, in some embodiments m is 3, as shown below:

Formula Ia

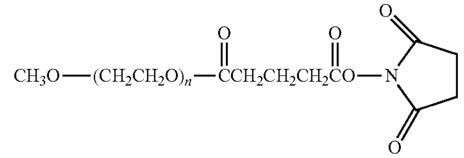

Formula II

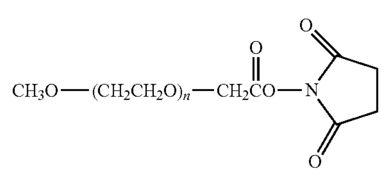

In Formula II, the moiety comprising the reactive functional group has the general structure —$(CH_2)_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

Formula III

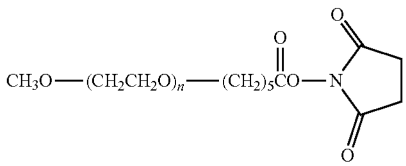

Formula IIIa

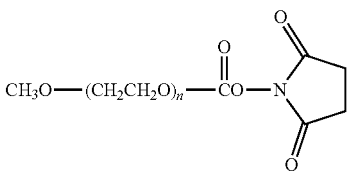

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —$(CH_2CH_2O)_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

Formula B

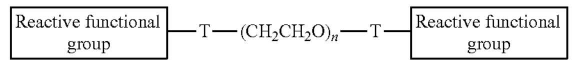

wherein each T and "Reactive functional group" is independently as defined above and described in classes and subclasses herein, and n is as defined above and described in classes and subclasses herein.

Exemplary bifunctional PEGs of formula B include:

Formula IV

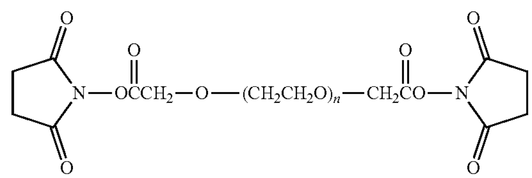

In Formula IV, the moiety comprising the reactive functional group has the general structure —$(CH_2)_m$—COO—NHS, where m=1. In some embodiments, a bifunctional PEG has the structure of Formula IV, where m is between 1 and 10, e.g., between 1 and 5. In certain embodiments m is 0, e.g., embodiments the moiety comprising the reactive functional group has the general structure —COO—NHS. For example, in some embodiments a bifunctional PEG has the structure of Formula IVa, as shown below:

Formula IVa

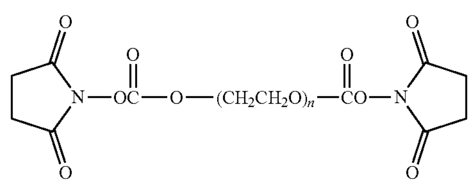

Formula V

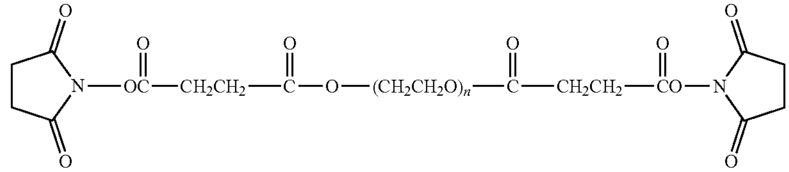

In Formula V, the moiety comprising the reactive functional group has the general structure —CO—$(CH_2)_m$—COO—NHS, where m=2. In some embodiments, a bifunctional PEGs has the structure of Formula V, where m is between 1 and 10, e.g., between 1 and 5. In certain embodiments, for example, m is 2, as shown below:

Formula Va

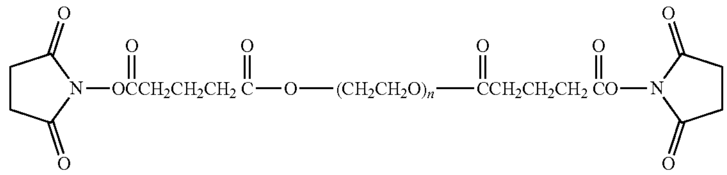

In some embodiments, the present invention provides a compstatin analog conjugated to a polymer. In certain embodiments, the present invention provides compstatin analog conjugates of PEG-containing compounds and genera depicted herein. In some embodiments, a functional group (for example, an amine, hydroxyl, or thiol group) on a compstatin analog is reacted with a PEG-containing compound having a "reactive functional group" as described herein, to generate such conjugates. By way of example, Formulae III and IV, respectively, can form compstatin analog conjugates having the structure:

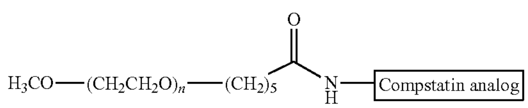

or

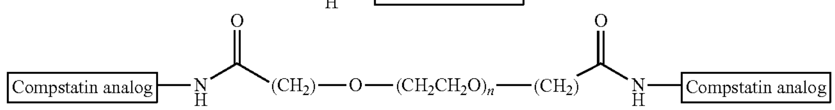

wherein,

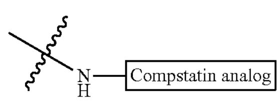

represents the attachment point of an amine group on a compstatin analog. In certain embodiments, an amine group is a lysine side chain group.

It will be appreciated that corresponding conjugates can be formed with any of the PEG-containing compounds and genera depicted herein, depending on the choice of reactive functional group and/or compstatin functional group. For example, Formulae IVa and Va, respectively, can form compstatin analog conjugates having the following structures

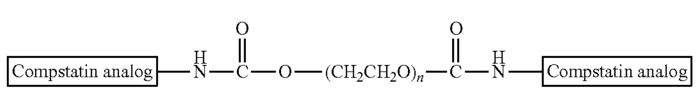

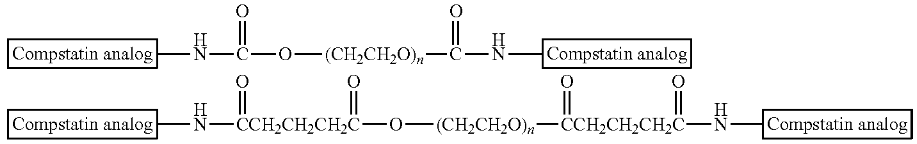

In certain embodiments, the PEG component of such conjugates has an average molecular weight of between about 10 kD-100 kD, about 10 kD-90 kD, about 10 kD-80 kD, about 10 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In certain embodiments, the PEG component of such conjugates has an average molecular weight of about 10 kD. In certain embodiments, the PEG component of such conjugates has an average molecular weight of about 40 kD.

The term "bifunctional" or "bifunctionalized" is sometimes used herein to refer to a compound comprising two compstatin analog moieties linked to a CRM. Such compounds may be designated with the letter "BF". In some embodiments a bifunctionalized compound is symmetrical. In some embodiments the linkages between the CRM and each of the compstatin analog moieties of a bifunctionalized compound are the same. In some embodiments, each linkage between a CRM and a compstatin analog of a bifunctionalized compound comprises a carbamate. In some embodiments, each linkage between a CRM and a compstatin analog of a bifunctionalized compound comprises a carbamate and does not comprise an ester. In some embodiments, each compstatin analog of a bifunctionalized compound is directly linked to a CRM via a carbamate. In some embodiments, each compstatin analog of a bifunctionalized compound is directly linked to a CRM via a carbamate, and the bifunctionalized compound has the structure:

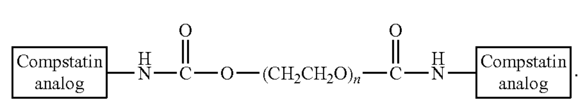.

In some embodiments of formulae and embodiments described herein,

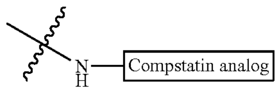

represents point of attachment of a lysine side chain group in a compstatin analog having the structure:

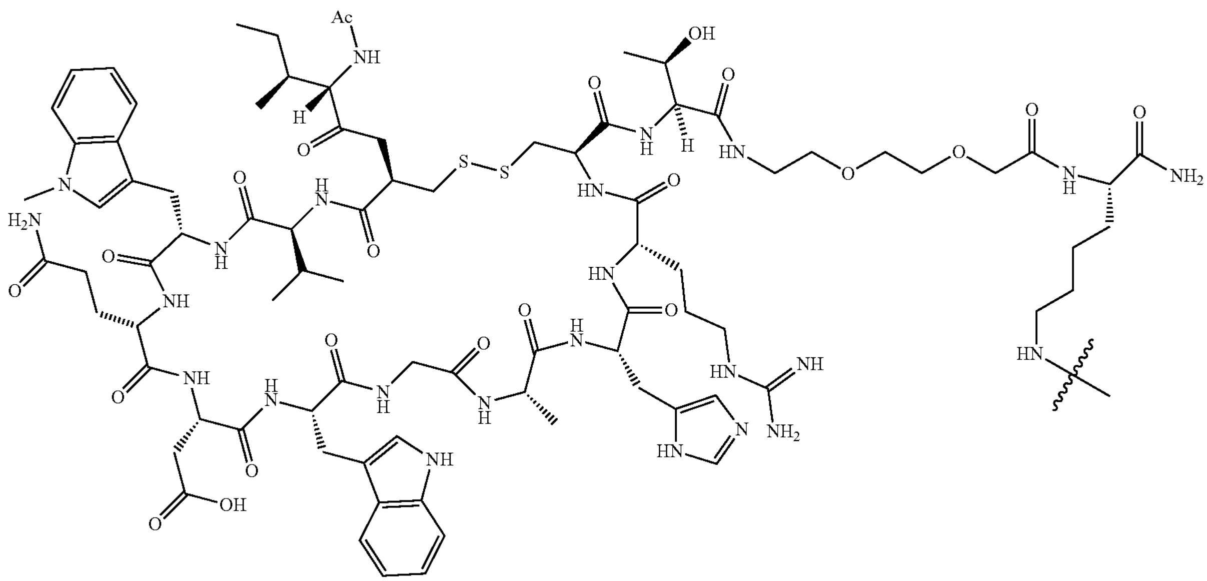 [SMILES: *NCCCC[C@H](NC(=O)COCCOCCNC(=O)[C@@H](NC(=O)[C@@H]1CSSC[C@H](CC(=O)[C@@H](NC(C)=O)[C@@H](C)CC)C(=O)N[C@@H](C(C)C)C(=O)N[C@@H](Cc2cn(C)c3ccccc23)C(=O)N[C@@H](CCC(N)=O)C(=O)N[C@@H](CC(=O)O)C(=O)N[C@@H](Cc2c[nH]c3ccccc23)C(=O)NCC(=O)N[C@@H](C)C(=O)N[C@@H](Cc2cnc[nH]2)C(=O)N[C@@H](CCCNC(=N)N)C(=O)N1)[C@@H](C)O)C(N)=O]

wherein the symbol "∿∿" denotes the point of attachment of a chemical moiety to the remainder of a molecule or chemical formula.

In some embodiments, a branched, comb, or star-shaped PEG comprises a moiety comprising a reactive functional group at the end of each of multiple $-(CH_2CH_2O)_n$ chains. The reactive functional groups may be the same or there may be at least two different groups. In some embodiments, a branched, comb, or star-shaped PEG is of the following formulae:

Formula C

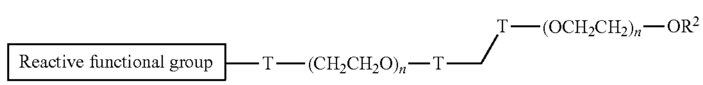

Formula D

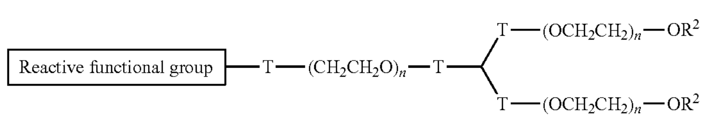

Formula E

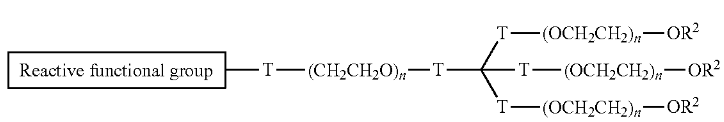

-continued

Formula F

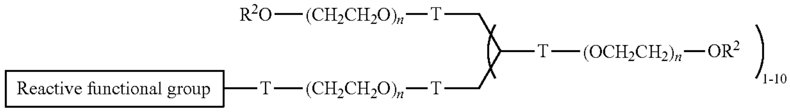

Formula G

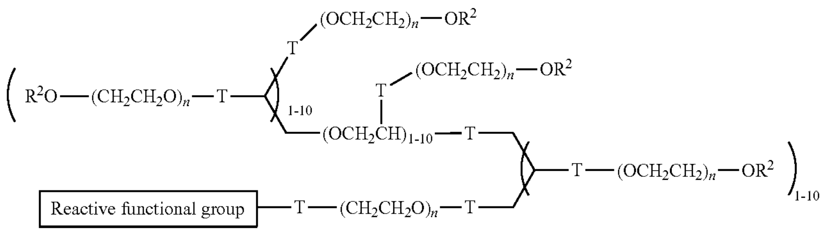

Formula H

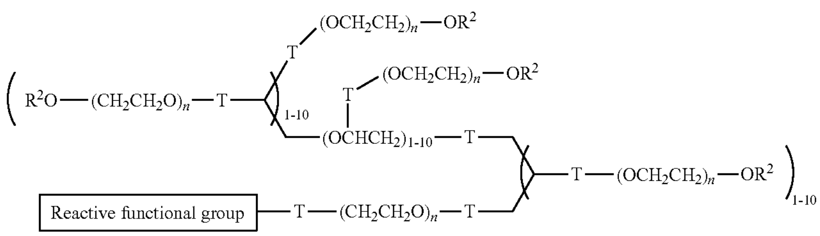

wherein each $R^2$ is independently a "Reactive functional group" or $R^1$, and each T, n, and "Reactive functional group" is independently as defined above and described in classes and subclasses herein. The structure of exemplary branched PEGs (having 8 arms, or branches) comprising NHS moieties as reactive functional groups is depicted below:

Formula VI

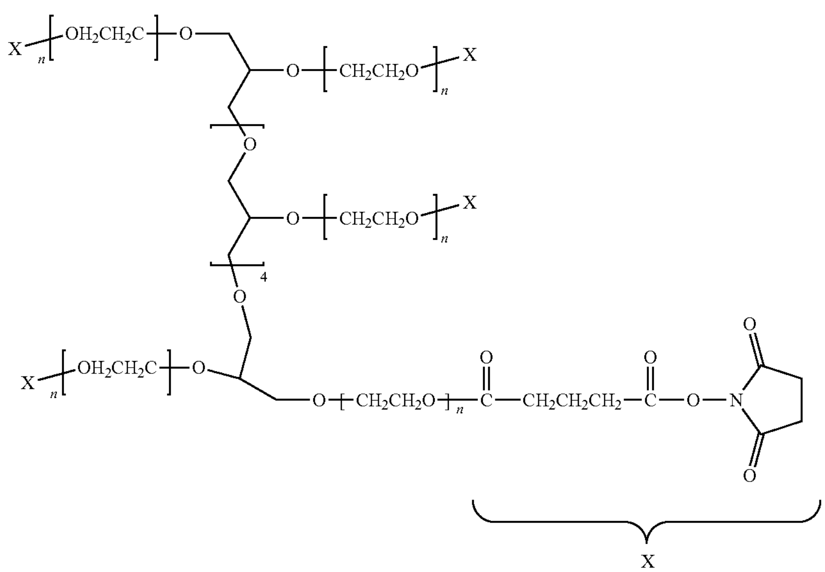

-continued

Formula VII

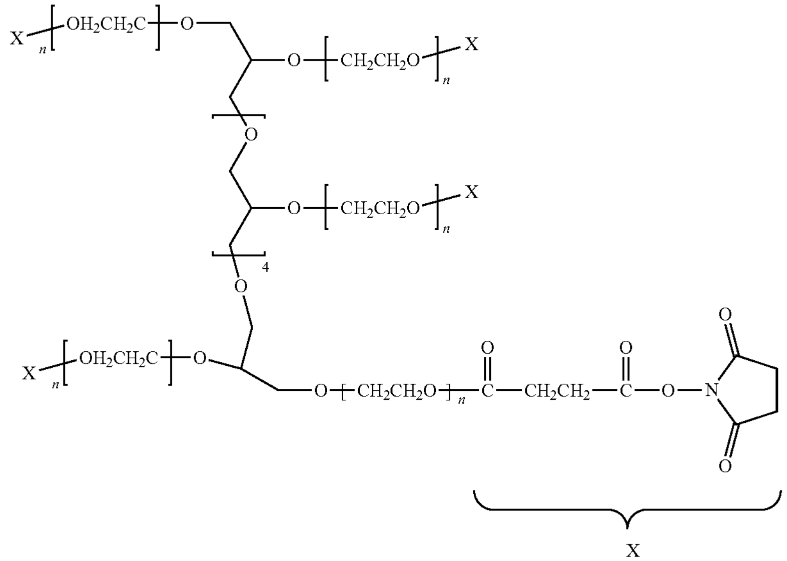

The structure of exemplary branched PEGs (having 4 arms, or branches) comprising NHS moieties as reactive functional groups is depicted below:

Formula VIII

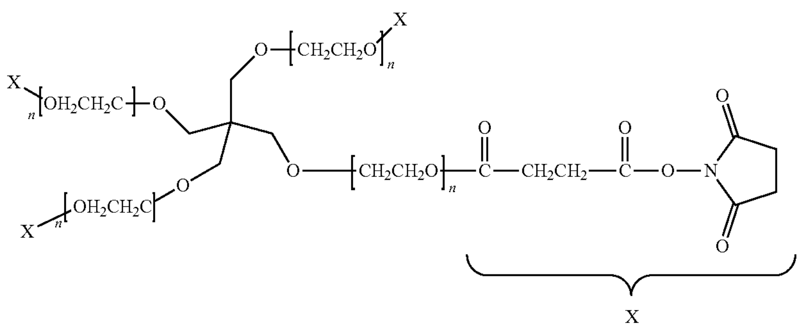

Formula IX

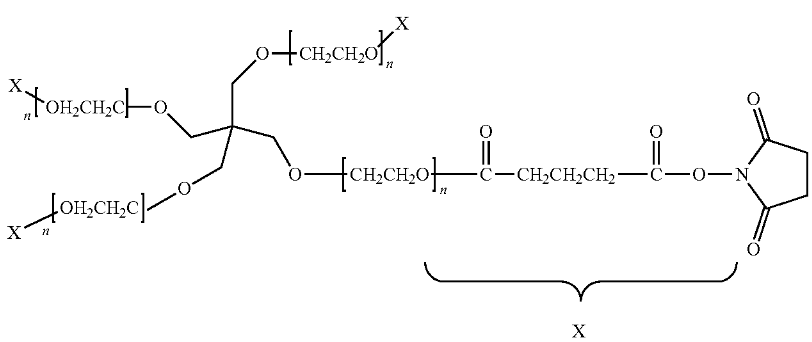

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a $—CH_2CH_2OH$ or $—CH_2CH_2OR$ group, as described above.

In some embodiments a branched PEG has the structure of Formula VII, VIII, or IX (or variants thereof having different numbers of branches) with the proviso that x is

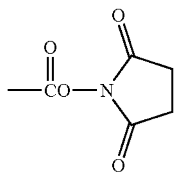

In some embodiments a branched PEG has the structure of Formula VII, VIII, or IX (or variants thereof having different numbers of branches) with the proviso that x is

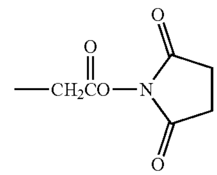

Of course the methylene ($CH_2$) group in the above x moiety may instead comprise a longer alkyl chain $(CH_2)_m$, where m is up to 2, 3, 4, 5, 6, 8, 10, 20, or 30, or may comprise one or more other moieties described herein.

In some embodiments, exemplary branched PEGs having NHS or maleimide reactive groups are depicted below:

Formula X

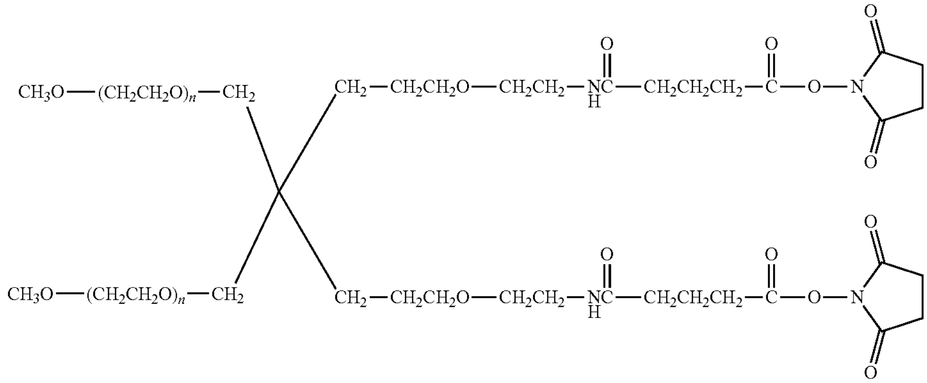

Formula XI

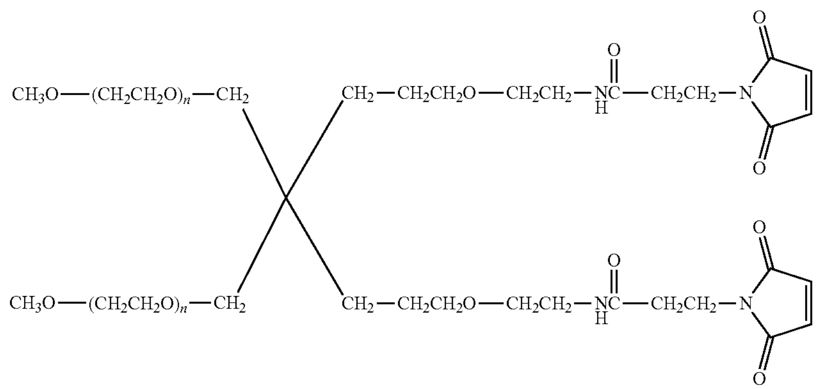

In some embodiments, a variant of Formula X or XI are used, wherein 3 or each of the 4 branches comprise a reactive functional group.

Still other examples of PEGs may be represented as follows:

Formula XII

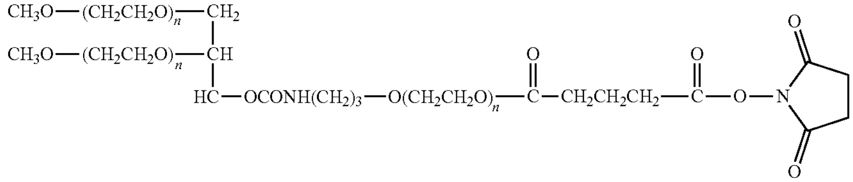

Formula XIII

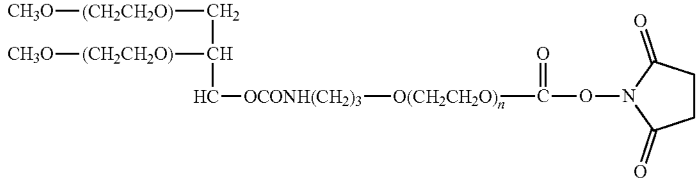

As noted above, it will be appreciated that, as described herein, in various embodiments any of a variety of moieties may be incorporated between the peptide component and $(CH_2CH_2O)_n$—R moiety of a long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the compound from the CRM. In some embodiments, such release may enhance the in vivo tissue penetration and/or activity of the compound. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a reactive functional group are as follows:

Formula XIV

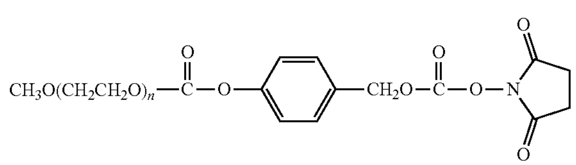

Formula XV

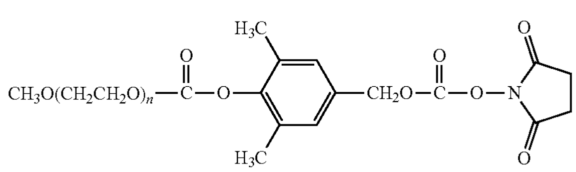

Formula XVI

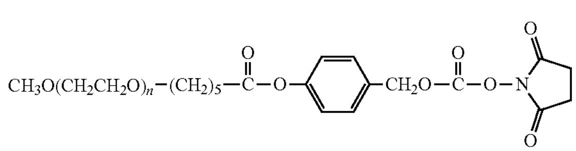

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Monofunctional, bifunctional, branched, and other PEGs comprising one or more reactive functional groups may, in some embodiments, be obtained from, e.g., NOF America Corp. White Plains, NY or BOC Sciences 45-16 Ramsey Road Shirley, NY 11967, USA, among others, or may be prepared using methods known in the art.

In some embodiments, a linkage between a CRM and a compstatin analog comprises a carbamate. In some embodiments, a compstatin analog is directly linked to a CRM via a carbamate. In some embodiments, a linkage between a CRM and a compstatin analog does not comprise an ester. In some embodiments, a linkage between a CRM and a compstatin analog comprises a carbamate and does not comprise an ester. In some embodiments, a linkage between a CRM and a compstatin analog comprises a carbamate and does not comprise a bond that is more susceptible to hydrolysis in aqueous medium than a carbamate. In some embodiments the CRM comprises or consists of a PEG moiety.

In some embodiments, a linkage between a CRM and a compstatin analog comprises an amide. In some embodiments, a compstatin analog is directly linked to a CRM via an amide. In some embodiments, a linkage between a CRM and a compstatin analog comprises an amide and does not comprise an ester. In some embodiments, a linkage between a CRM and a compstatin analog comprises an amide and does not comprise a bond that is more susceptible to hydrolysis in aqueous medium than an amide. In some embodiments the CRM comprises or consists of a PEG moiety.

In some embodiments, one or more compstatin analogs of a multifunctionalized compound (e.g., a bifunctionalized, trifunctionalized, or more extensively functionalized compound) is linked to a CRM by a linkage comprising a carbamate. In some embodiments, one or more compstatin analogs of a multifunctionalized compound (e.g., a bifunctionalized, trifunctionalized, or more extensively functionalized compound) is linked to a CRM by a linkage that does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise an ester. In some embodiments, one or more compstatin analogs of a multifunctionalized compound (e.g., a bifunctionalized, trifunctionalized, or more extensively functionalized compound) is linked to a CRM by a linkage that comprises a carbamate and does not comprise a bond that is more susceptible to hydrolysis in aqueous medium than a carbamate. In some embodiments, each compstatin analog of a multifunctionalized compound (e.g., a bifunctionalized, trifunctionalized, or more extensively functionalized compound) is directly linked to a CRM via a carbamate.

In some embodiments the CRM comprises or consists of a PEG moiety. In some embodiments, one or more compstatin analogs of a multifunctionalized compound (e.g., a bifunctionalized, trifunctionalized, or more extensively functionalized compound) is linked to a CRM by a linkage comprising an amide. In some embodiments, one or more compstatin analogs of a multifunctionalized compound (e.g., a bifunctionalized, trifunctionalized, or more extensively functionalized compound) is linked to a CRM by a linkage that comprises an amide and does not comprise an ester. In some embodiments, one or more compstatin analogs of a multifunctionalized compound (e.g., a bifunctionalized, trifunctionalized, or more extensively functionalized compound) is linked to a CRM by a linkage that comprises an amide and does not comprise a bond that is more susceptible to hydrolysis in aqueous medium than an amide. In some embodiments, each compstatin analog of a multifunctionalized compound (e.g., a bifunctionalized, trifunctionalized, or more extensively functionalized compound) is directly linked to a CRM via an amide. In some embodiments the CRM comprises or consists of a PEG moiety.

In some embodiments, the present invention provides a compstatin analog conjugated with a polymer, wherein the polymer is other than PEG. In some embodiments, a polymer is a polyoxazoline (POZ). Exemplary mono- and polyfunctionalized polyoxazoline derivatives for direct conjugation, or for conjugation via a linker, are depicted below:

$Z\text{-}T\text{-}[N(COR^x)CH_2CH_2]_n\text{-}T\text{-}R^1$;

$R^1—\{[N(CO\text{-}T\text{-}Z)CH_2CH_2]_m—[N(COR^x)CH_2CH_2]_n\}^a\text{-}T\text{-}R^1$;

$R^1—\{[N(CO\text{-}T\text{-}Z^1)CH_2CH_2]_p—[N(COR^x)CH_2CH_2]—[N(CO\text{-}T\text{-}Z^2)CH_2CH_2]_m\}^a\text{-}T\text{-}R^1$;

$R^1—\{[N(CO\text{-}T\text{-}Z^1)CH_2CH_2]_p—[N(COR^x)CH_2CH_2]_n—[N(CO\text{-}T\text{-}Z^2)CH_2CH_2]_m\}^a\text{-}T\text{-}Z$;

$R^1—[N(COR^x)CH_2CH_2]_n\text{-}T\text{-}B(—R^1)(\text{-}T\text{-}Z)\text{-}T\text{-}[N(COR^x)CH_2CH_2]_m—R^1$;

wherein:

each of Z, $Z^1$ and $Z^2$ is independently a reactive functional group as defined above and described in classes and subclasses herein;

each of T, $R^x$, and $R^1$ is independently as defined above and described in classes and subclasses herein;

each of m, n, and p is independently an integer 0-1000, with the limitation that the sum of m, n, and p for each formula is not 0;

a is “ran,” which indicates a random copolymer, or “block,” which indicates a block copolymer;

B is a branching moiety that is linked with or without a linker to the other parts of the polymer. Other examples of functionalized polyoxazoline derivatives for conjugation are extensively described in the art, including but not limited to those described in PCT Patent Application Publication Nos. WO/2010/006282, WO/2009/089542, WO/2009/043027 and WO/2008/106186, the entirety of each of which is hereby incorporated by reference.

Exemplary compstatin analog conjugates with polyoxazoline polymers are depicted below:

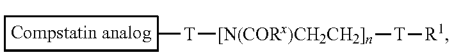,

-continued

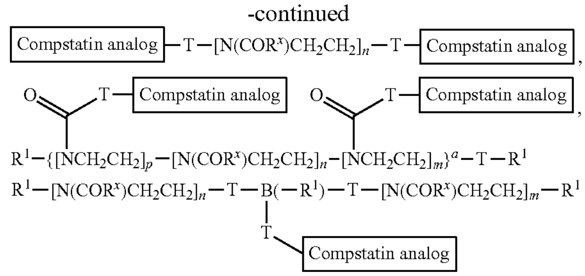

wherein each variable is independently as defined above and described in classes and subclasses herein.

In some embodiments, the present invention provides a compstatin analog conjugated with a polymer, wherein the compstatin analog is connected to the polymer via one or more linkers. In some embodiments, a polymer is selected from PEG-containing compounds and genera described above and in classes and subclasses herein. In some embodiments, the present invention provides compstatin analog conjugates of PEG-containing compounds and genera depicted herein, wherein the compstatin analog is connected to the PEG-containing moieties via one or more linkers. Mono- and poly-functional PEGs that comprise one or more reactive functional groups for conjugation are defined above and described in classes and subclasses herein, including but not limited to those of formula A, I, Ia, II, III, IIIa, B, IV, IVa, V, Va, C, D, E, F, G, H, VI, VII, VIII, IX, X, XI, XII, XIII, XIV, XV, or XVI.

Suitable linkers for connecting a compstatin analog and a polymer moiety such as PEG or polyoxazoline are extensively described above and in classes and subclasses herein. In some embodiments, a linker has multiple functional groups, wherein one functional group is connected to a compstatin analog and another is connected to a polymer moiety. In some embodiments, a linker is a bifunctional compound. In some embodiments, a linker has the structure of $NH_2(CH_2CH_2O)nCH_2C(═O)OH$, wherein n is 1 to 1000. In some embodiments, a linker is 8-amino-3,6-dioxaoctanoic acid (AEEAc). In some embodiments, a linker is activated for conjugation with a polymer moiety or a functional group of a compstatin analog. For example, in some embodiments, the carboxyl group of AEEAc is activated before conjugation with the amine group of the side chain of a lysine group.

In some embodiments, a suitable functional group (for example, an amine, hydroxyl, thiol, or carboxylic acid group) on a compstatin analog is used for conjugation with a polymer moiety, either directly or via a linker. In some embodiments, a compstatin analog is conjugated through an amine group to a PEG moiety via a linker. In some embodiments, an amine group is the α-amino group of an amino acid residue. In some embodiments, an amine group is the amine group of the lysine side chain. In some embodiments, a compstatin analog is conjugated to a PEG moiety through the amino group of a lysine side chain (¿-amino group) via a linker having the structure of $NH_2(CH_2CH_2O)nCH_2C(═O)OH$, wherein n is 1 to 1000. In some embodiments, a compstatin analog is conjugated to the PEG moiety through the amino group of a lysine side chain via an AEEAc linker. In some embodiments, the $NH_2(CH_2CH_2O)nCH_2C(═O)OH$ linker introduces a $—NH(CH_2CH_2O)nCH_2C(═O)—$ moiety on a compstatin lysine side chain after conjugation. In some embodiments, the AEEAc linker introduces a $—NH(CH_2CH_2O)_2CH_2C(═O)—$ moiety on a compstatin lysine side chain after conjugation.

In some embodiments, a compstatin analog is conjugated to a polymer moiety via a linker, wherein the linker comprises an AEEAc moiety and an amino acid residue. In some embodiments, a compstatin analog is conjugated to a polymer moiety via a linker, wherein the linker comprises an AEEAc moiety and a lysine residue. In some embodiments, a polymer is PEG. In some embodiments, the C-terminus of a compstatin analog is connected to the amino group of AEEAc, and the C-terminus of AEEAc is connected to a lysine residue. In some embodiments, the C-terminus of a compstatin analog is connected to the amino group of AEEAc, and the C-terminus of AEEAc is connected to the α-amino group of a lysine residue. In some embodiments, the C-terminus of a compstatin analog is connected to the amino group of AEEAc, the C-terminus of AEEAc is connected to the α-amino group of the lysine residue, and a polymer moiety, such as a PEG moiety, is conjugated through the s-amino group of said lysine residue. In some embodiments, the C-terminus of the lysine residue is modified. In some embodiments, the C-terminus of the lysine residue is modified by amidation. In some embodiments, the N-terminus of a compstatin analog is modified. In some embodiments, the N-terminus of a compstatin analog is acetylated.

Exemplary conjugates comprising an AEEAc linker and a polymer are depicted below, wherein

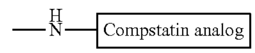

represents the attachment point of an amine group on a compstatin analog,

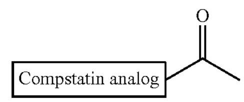

represents a compstatin analog attaching through its C-terminus, and wherein each of the other variables is independently as defined above and described in classes and subclasses herewith. In some embodiments, an amine group is the amino group of a lysine side chain.

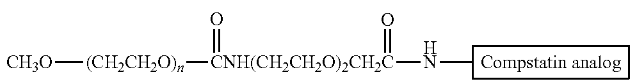

,

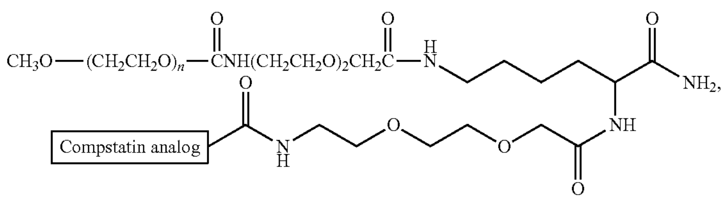

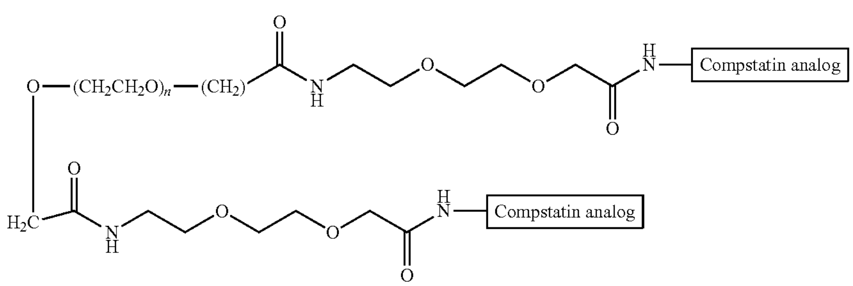

,

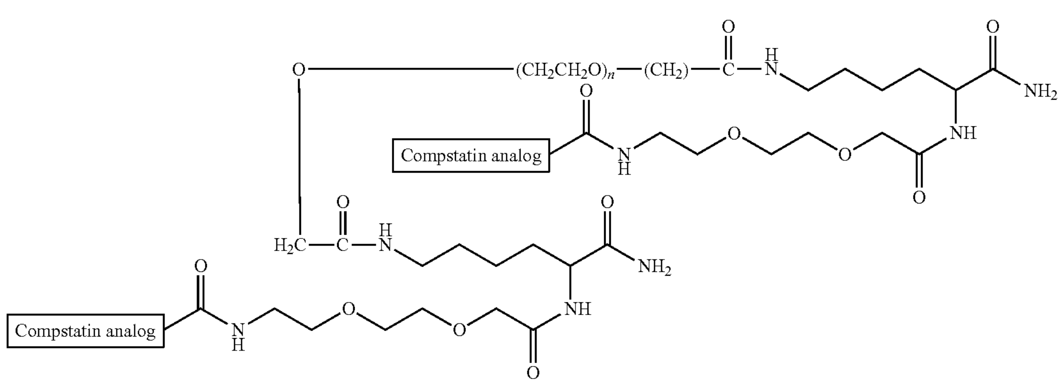

-continued
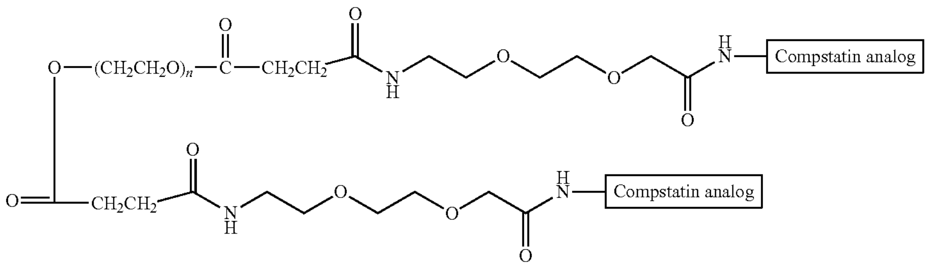
,
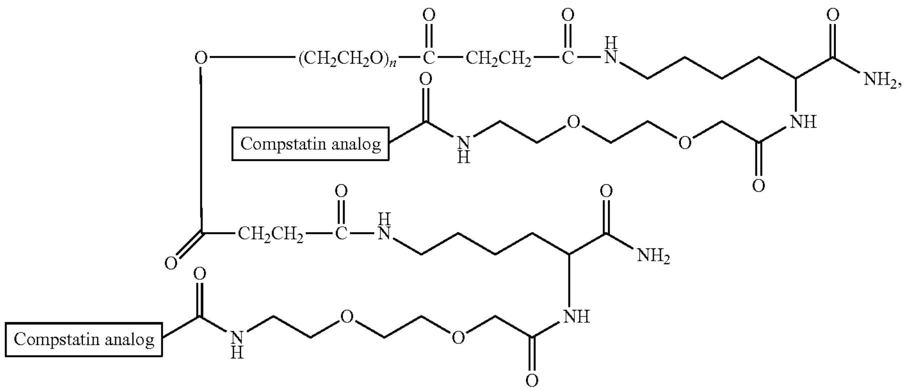
Compstatin analog—$NHC(O)CH_2(OCH_2CH_2)_2NH$—T—$[N(COR^x)CH_2CH_2]_n$—T—$R^1$,
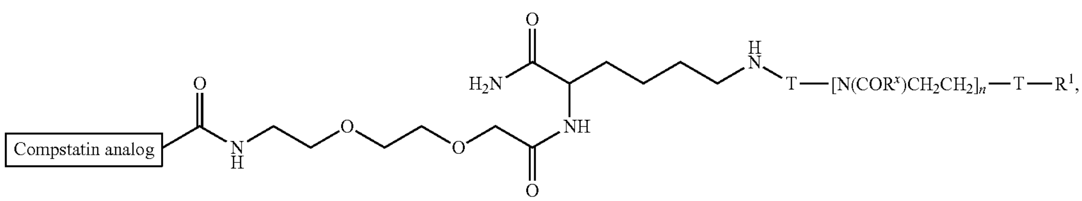
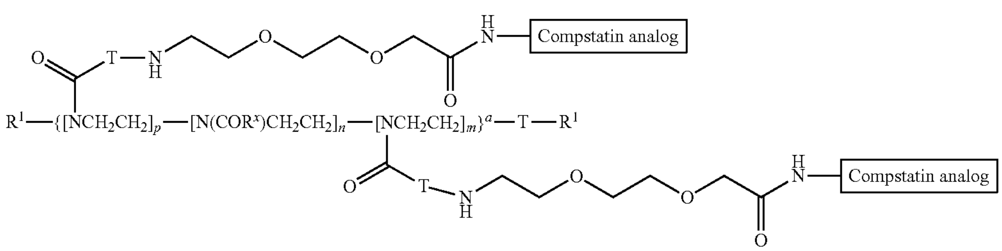
,
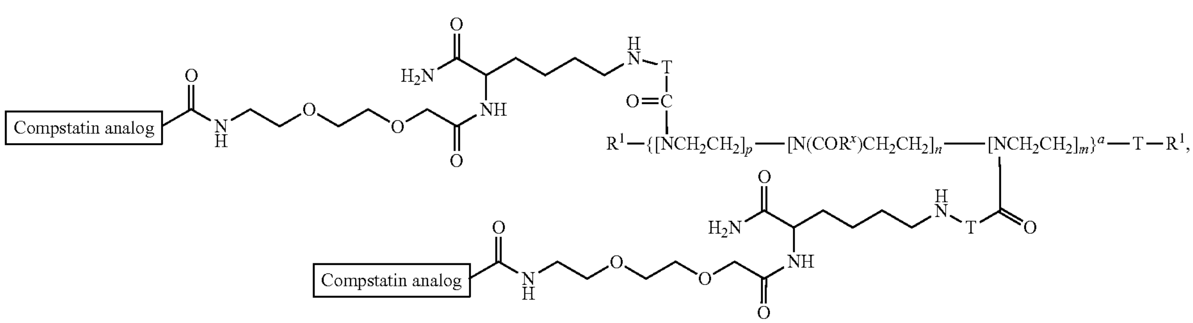
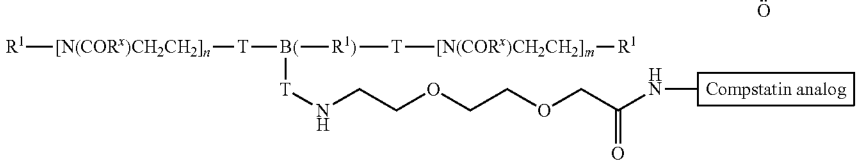
, -continued

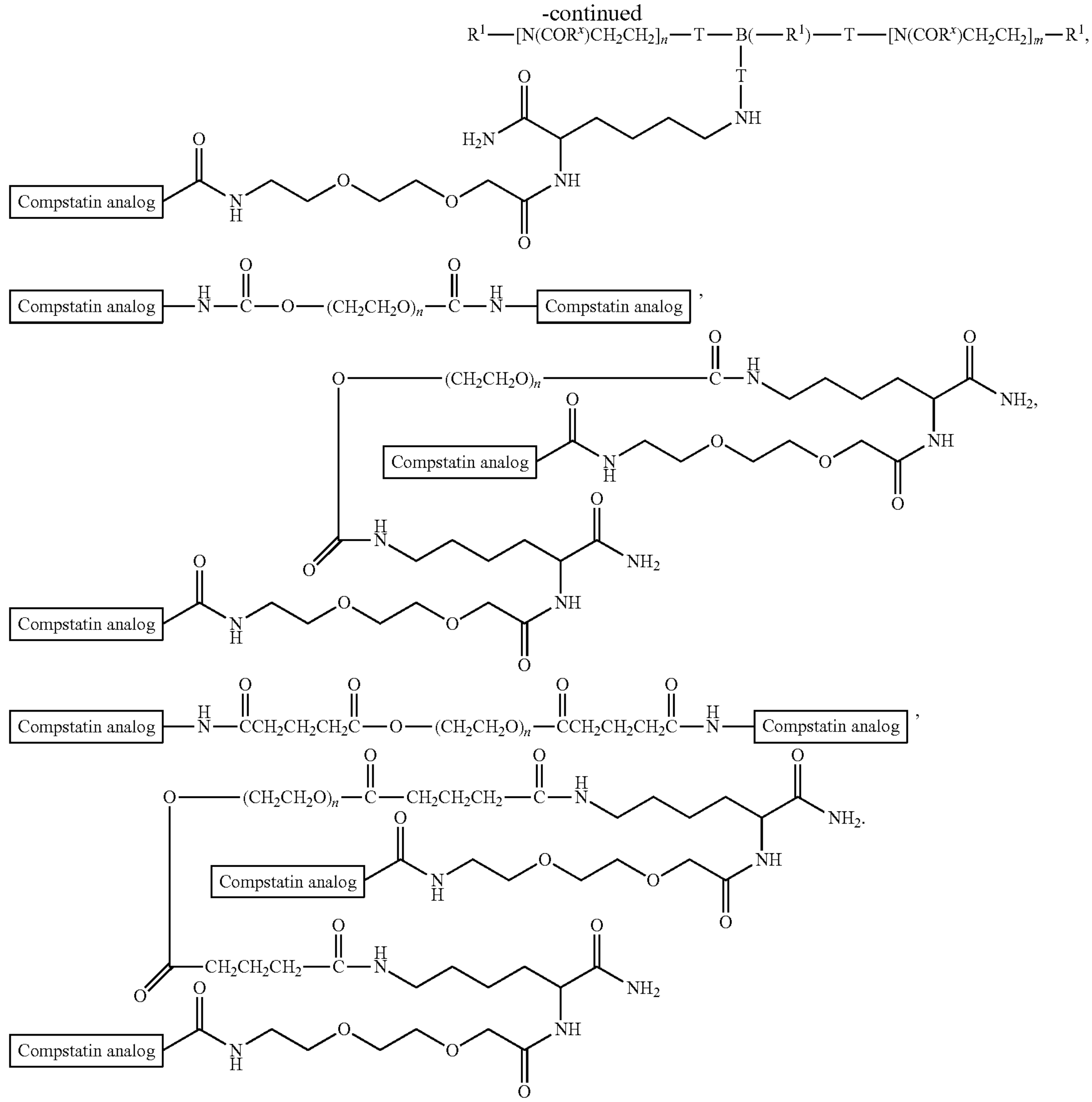

In certain embodiments a compstatin analog may be represented as M-AEEAc-Lys-$B_2$, wherein $B_2$ is a blocking moiety, e.g., $NH_2$, M represents any of SEQ ID NOs: 3-36, 37, 69, 70, 71, or 72, with the proviso that the C-terminal amino acid of any of SEQ ID NOs: 3-36, 37, 69, 70, 71, or 72 is linked via a peptide bond to AEEAc-Lys-B2. The NHS moiety of a monofunctional or multifunctional (e.g., bifunctional) PEG reacts with the free amine of the lysine side chain to generate a monofunctionalized (one compstatin analog moiety) or multifunctionalized (multiple compstatin analog moieties) long-acting compstatin analog. In various embodiments any amino acid comprising a side chain that comprises a reactive functional group may be used instead of Lys (or in addition to Lys). A monofunctional or multifunctional PEG comprising a suitable reactive functional group may be reacted with such side chain in a manner analogous to the reaction of NHS-ester activated PEGs with Lys.

With regard to any of the above formulae and structures, it is to be understood that embodiments in which the compstatin analog component comprises any compstatin analog described herein, e.g., any compstatin analog of SEQ ID NOs; 3-36, 37, 69, 70, 71, or 72, are expressly disclosed. For example, and without limitation, a compstatin analog may comprise the amino acid sequence of SEQ ID NO: 28. An exemplary long-acting compstatin analog in which the compstatin analog component comprises the amino acid sequence of SEQ ID NO: 28 is depicted in FIG. 1. It will be understood that the PEG moiety may have a variety of different molecular weights or average molecular weights in various embodiments, as described herein. For example, individual PEG chains within a preparation may vary in molecular weight and/or different preparations may have different average molecular weights and/or polydispersity, as described herein. In certain embodiments, the PEG moiety in the compound of FIG. 1 has an average molecular weight of between about 5 kD-100 kD, about 5 kD-90 kD, about 10 kD-80 kD, about 20 kD-70 kD, about 20 kD-60 kD, about 20 kD-50 kD, about 30 kD-80 kD, about 30 kD-70 kD, about 30 kD-60 kD, about 30 kD-50 kD, about 30 kD-45 kD, about 35 kD-50 kD, about 35 kD-45 kD, about 36 kD-44 kD, about 37 kD-43 kD, about 38 kD-42 kD, or about 39 kD-41 kD. In some embodiments the PEG moiety in the compound of FIG. 1 has an average molecular weight between about 30 kD and about 50 kD, e.g., between about 35 kD and about 45 kD, between about 37.5 kD and about 42.5 kD. In certain embodiments in which the PEG moiety has an average molecular weight of about 40 kD, e.g., 37.5 kD-42.5 kD, 38 kD, 39 kD, 40 kD, 41 kD, 42 kD, the compound is sometimes referred to herein as CA28-2TS-BF. In some embodiments the PEG moiety in the compound of FIG. 1 has an average molecular weight between about 10 kD. In certain embodiments a compound comprising a CRM, e.g., a PEG moiety, that has an average molecular weight of about 40 kD, e.g., 37.5 kD-42.5 kD, 38 kD, 39 kD, 40 kD, 41 kD, 42 kD, the compound has a terminal half-life of at least about 5 days, e.g., about 5-10 days, e.g., about 5, 6, 7, 8, 9 days, when administered IV or subcutaneously to non-human primates or humans, e.g., at a dose of about 1-3 mg/kg, 3-5 mg/kg, or 5-10 mg/kg.

In some aspects, the present invention relates to use of click chemistry in connection with compstatin analogs. "Click chemistry" is well known in the art and is useful in some aspects of the present invention. Click chemistry embodies, in certain embodiments, versatile cycloaddition reactions between azides and alkynes that enable a number of useful applications. Methods of carrying out click chemistry are known in the art, and are described by Kolb, H. C.; Sharpless, K. B., Drug Disc. Today, 2003, 1128-1137; Moses, J. E.; Moorhouse, A. D.; *Chem. Soc. Rev.,* 2007, 1249-1262; the entire contents of each are hereby incorporated by reference. Click chemistry is a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques and synthetic methods permit the introduction of azides and alkyne-bearing non-canonical amino acids into peptides, proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125, 11782-11783.

As used herein, the term "click chemistry group" is sometimes used to refer\ to a reactive functional group capable of participating in a click chemistry reaction with an appropriate second reactive functional group, which second reactive functional group is also a click chemistry group. The first and second click chemistry groups, or entities (e.g., molecules) comprising such groups, may be referred to as complementary. First and second entities, e.g., molecules, that comprise complementary click chemistry groups, may be referred to as click chemistry partners. An entity or molecule comprising a click chemistry group may be referred to as "click-functionalized". A bond formed by reaction of complementary click chemistry partners may be referred to as a "click chemistry bond".

In some embodiments, the present invention provides click-functionalized compstatin analogs for, e.g., conjugation to a complementary moiety on a partner molecule or biomolecule. In some embodiments, a complementary partner molecule or biomolecule is a polymer, peptide, protein, or a molecule that functions as a clearance-reducing moiety. In some embodiments, the "click-functionalized" moiety is an alkyne or an alkyne derivative which is capable of undergoing [3+2] cycloaddition reactions with complementary azide-bearing molecules and biomolecules. In another embodiment, the "click-functionalized" functionality is an azide or an azide derivative which is capable of undergoing [3+2] cycloaddition reactions with complementary alkyne-bearing molecules and biomolecules (i.e. click chemistry).

In some embodiments, a click-functionalized compstatin analog bears an azide group on any side chain group of the compstatin analog. In some embodiments, a click-functionalized compstatin analog bears an azide group on a lysine side chain group.

In some embodiments, a click-functionalized compstatin analog bears an alkyne group on any side chain group of the compstatin compstatin analog. In some embodiments, a click-functionalized compstatin analog bears an alkyne group on a lysine side chain group.

In some embodiments, the present invention provides compstatin conjugates comprising a compstatin analog, a molecule that functions as a clearance-reducing moiety, and a triazole linker. In some embodiments, a triazole linker is the result of click conjugation chemistry between a compstatin conjugate and a molecule that functions as a clearance-reducing moiety. In some embodiments the CRM may be any CRM disclosed herein. For example, the CRM may be a PEG, a polypeptide, or a POZ.

In some embodiments, the present invention provides compstatin conjugates comprising a compstatin analog, a PEG moiety, and a triazole linker. In some embodiments, a triazole linker is the result of click conjugation chemistry between a compstatin conjugate and a PEG moiety.

In some embodiments, the present invention provides compstatin conjugates comprising a compstatin analog, a polyoxazoline moiety, and a triazole linker. In some embodiments, a triazole linker is the result of click conjugation chemistry between a compstatin conjugate and a polyoxazoline moiety.

In some embodiments, click chemistry between a compstatin analog and another moiety is transition metal catalyzed. Copper-containing molecules which catalyze the "click" reaction include, but are not limited to, copper wire, copper bromide (CuBr), copper chloride (CuCl), copper sulfate ($CuSO_4$), copper sulfate pentahydrate ($CuSO_4 \cdot 5H_2O$), copper acetate ($Cu_2(AcO_4)$), copper iodide (CuI), $[Cu(MeCN)_4](OTf)$, $[Cu(MeCN)_4](PF_6)$, colloidal copper sources, and immobilized copper sources. In some embodiments other metals, such as ruthenium. Reducing agents as well as organic and inorganic metal-binding ligands can be used in conjunction with metal catalysts and include, but are not limited to, sodium ascorbate, tris (triazolyl) amine ligands, tris (carboxyethyl)phosphine (TCEP), sulfonated bathophenanthroline ligands, and benzimidazole-based ligands.

In some embodiments, compstatin analogs are conjugated to other moieties using metal free click chemistry (also known as copper free click chemistry) to give a metal free composition or conjugates. In contrast to standard click chemistry, also known as copper assisted click chemistry (CuACC), metal free click chemistry occurs between either a strained, cyclic alkyne or an alkyne precursor such as an oxanorbornadiene, and an azide group. As the name implies, no metal catalyst is necessary for the reaction to occur. Examples of such chemistries include reactions involving cyclooctyne derivatives (Codelli, et. al. *J. Am. Chem. Soc.,* 2008, 130, 11486-11493; Jewett, et. al. *J. Am. Chem. Soc.,* 2010, 132, 3688-3690; Ning, et. al. *Angew. Chem. Int. Ed.,* 2008, 47, 2253-2255), difluoro-oxanorbornene derivatives (van Berkel, et. al. *ChemBioChem,* 2007, 8, 1504-1508), or nitrile oxide derivatives (Lutz, et. al. *Macromolecules,* 2009, 42, 5411-5413). In certain embodiments a metal-free click chemistry reaction is a metal-free [3+2] cycloaddition reaction, Diels-Alder reaction, or thiol-alkene radical addition reaction. Exemplary click chemistry reactions and click chemistry groups are described in, e.g., Joerg Lahann, Click Chemistry for Biotechnology and Materials Science, 2009, John Wiley & Sons Ltd, ISBN 978-O-470-69970-6; Becer, Hoogenboom, and Schubert, Click Chemistry beyond Metal-Catalyzed Cycloaddition, Angewandte Chemie International Edition (2009) 48:4900-4908. In certain embodiments a click chemistry group comprises a diarylcyclooctyne.

Certain examples of metal free click chemistry are shown in the scheme below.

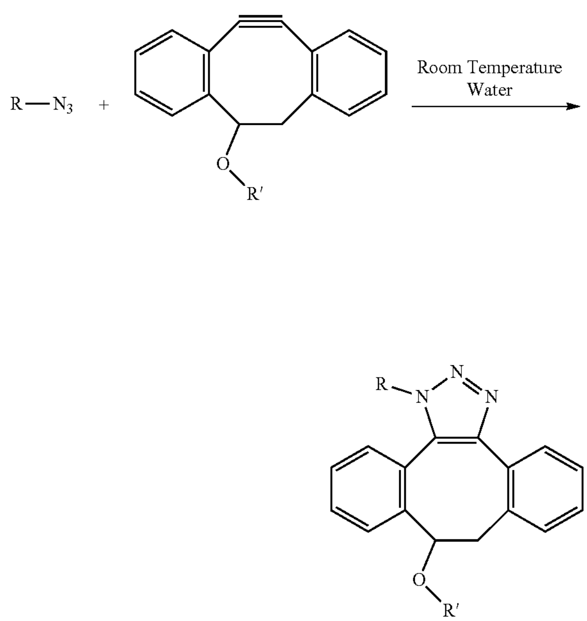

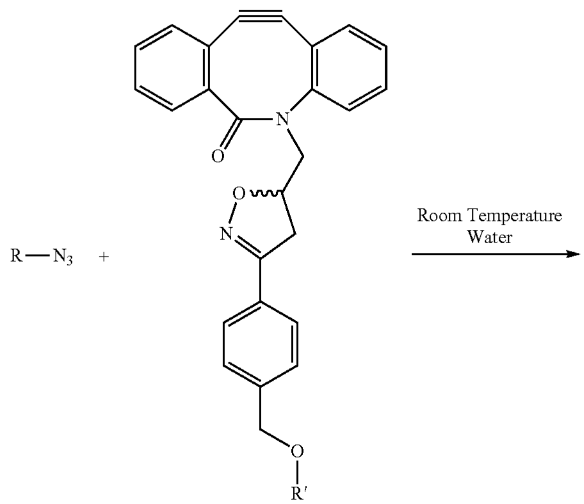

-continued

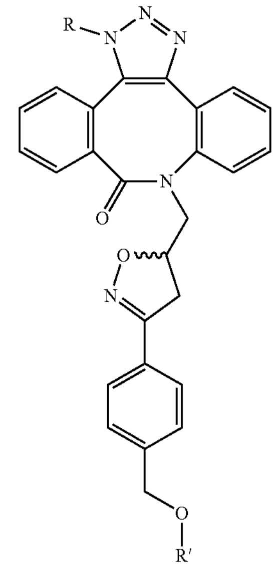

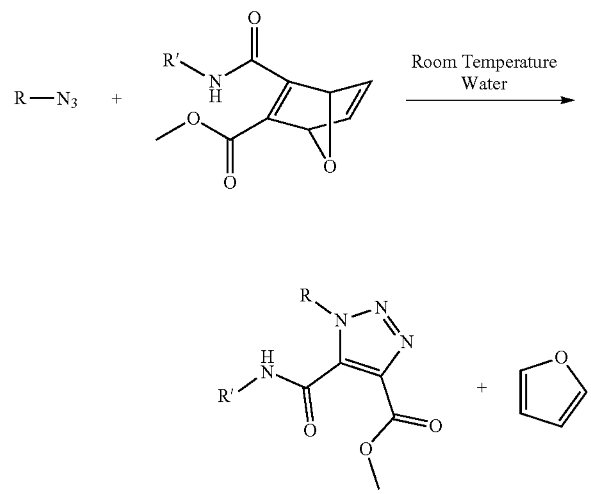

Certain metal-free click moieties are known in the literature. Examples include 4-dibenzocyclooctynol (DIBO)

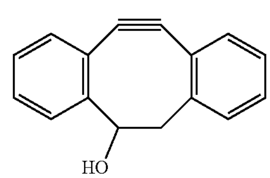 [SMILES: OC1Cc2ccccc2C#Cc2ccccc21]

(from Ning et. al; Angew Chem Int Ed, 2008, 47, 2253); difluorinated cyclooctynes (DIFO or DFO)

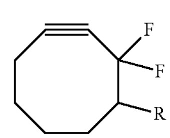

(from Codelli, et. al.; J. Am. Chem. Soc. 2008, 130, 11486-11493.); biarylazacyclooctynone (BARAC)

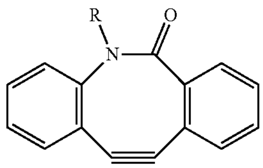

(from Jewett et. al.; J. Am. Chem. Soc. 2010, 132, 3688); or bicyclononyne (BCN)

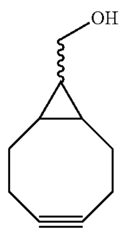 [SMILES: OCC1C2CCC#CCCC12]

(From Dommerholt, et. al.; *Angew Chem Int Ed,* 2010, 49, 9422-9425) or dibenzylcyclooctyne (DBCO)

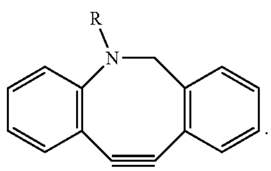

A reaction scheme involving reaction of DBCO and an azide is shown below:

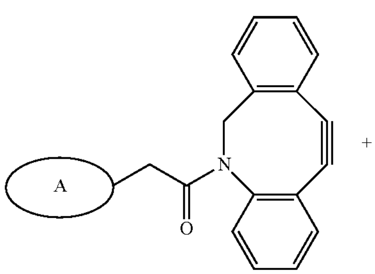

DBCO-containing molecule A

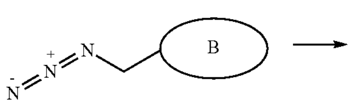

Azide-containing molecule B

-continued

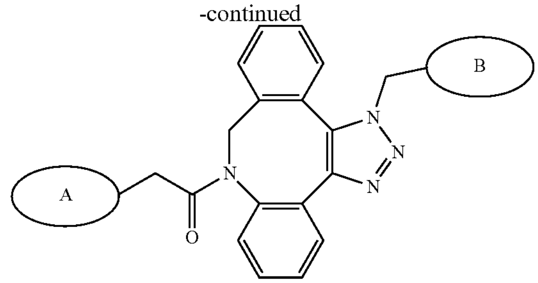

Conjugate of A and B, cross-linked via a Triazole moiety

In the above scheme, in various embodiments, A may comprise or consist of a compstatin analog moiety and B may comprise or consist of a CRM, e.g., a polymer, such as a PEG or a POZ or a polypeptide, or B may comprise or consist of a compstatin analog moiety and A may comprise or consist of a CRM, e.g., a polymer, such as a PEG or a POZ or a polypeptide.

In some embodiments, the “metal free click-functionalized” moiety is an acetylene or an acetylene derivative which is capable of undergoing [3+2] cycloaddition reactions with complementary azide-bearing molecules and biomolecules without the use of a metal catalyst.

In some embodiments, the R and R' groups of the metal-free click chemistry reagents are a compstatin analog or any molecule described herein to which a compstatin analog may be conjugated. In some embodiments, such compstatin analogs bear a click-functionalized moiety on a lysine side chain. In some embodiments, such compstatin analogs are connected to a click-functionalized moiety via a linker. In some embodiments, such compstatin analogs are connected to a click-functionalized moiety via AEEAc.

In some embodiments, a click chemistry reagent comprises DBCO. Exemplary reagents and exemplary uses thereof are set forth below:

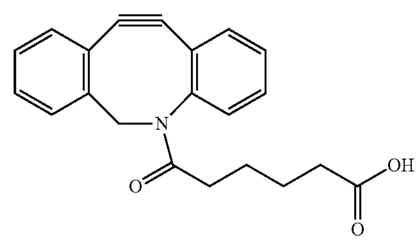 [SMILES: O=C(O)CCCCC(=O)N1Cc2ccccc2C#Cc2ccccc21]

DBCO-Acid. In some embodiments a DBCO-Acid may be used to react with an amine-containing moiety.

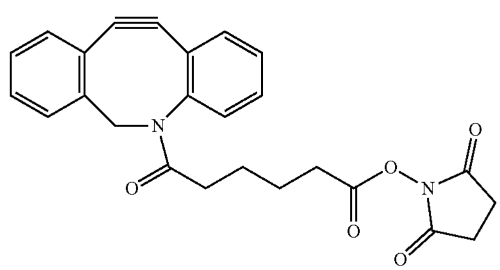 [SMILES: O=C(CCCCC(=O)N1Cc2ccccc2C#Cc2ccccc21)ON1C(=O)CCC1=O]

DBCO-NHS ester (above) or DBCO-sulfo-NHS ester (below) may be used to incorporate a DBCO functionality into an amine-containing molecule, such as a compstatin analog or a polypeptide comprising a lysine residue.

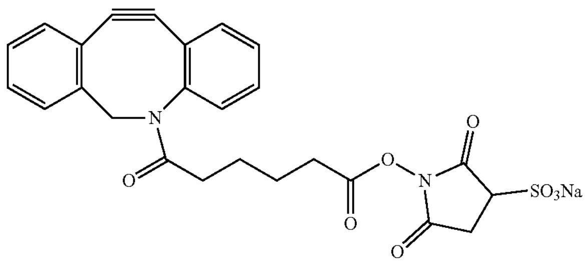

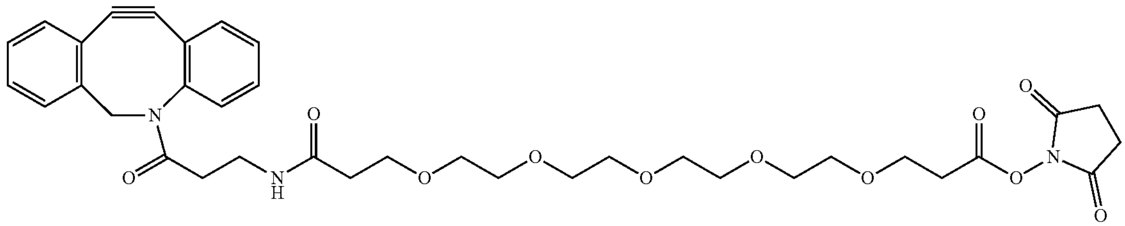

DBCO-PEG4-NHS ester. In some embodiments such reagent is useful for introducing a DBCO moiety by reaction with an available amine functionality. In some aspects, the presence of a PEG chain as a hydrophilic spacer may be useful to, e.g., increase solubility or provide flexibility.

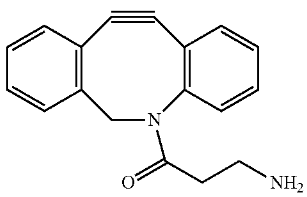 [SMILES: NCCC(=O)N1Cc2ccccc2C#Cc2ccccc21]

DBCO-Amine. In some embodiments a click chemistry reagent comprises a carbonyl/carboxyl reactive dibenzylcyclooctyne, which may react with acids, active esters and/or aldehydes.

In certain embodiments a click chemistry reaction involves a cyclooctyne depicted below:

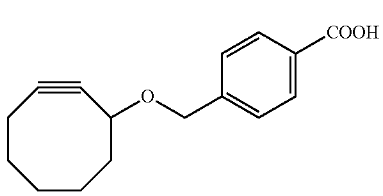

OCT

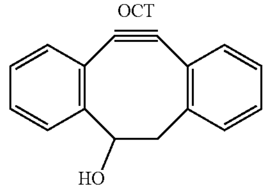

DIBO

-continued

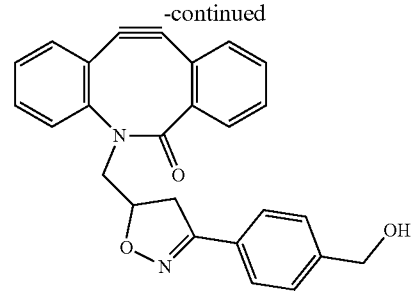

BARAC

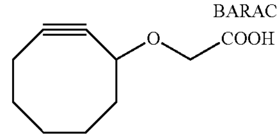

ALO

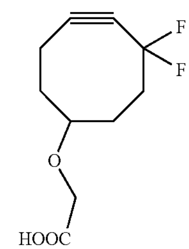

DIFO

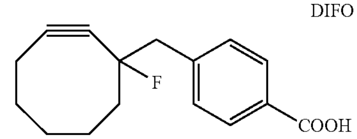

MOFO

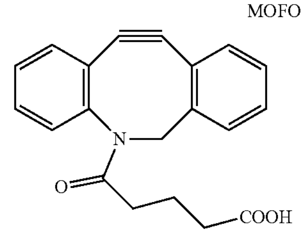

DIBAC

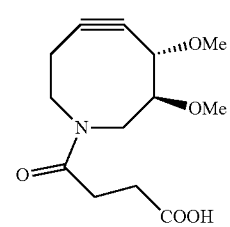

DIMAC

In certain embodiments click chemistry reactions comprise reactions between nitrones and cyclooctynes (see, e.g., Ning, Xinghai; Temming, Rinske P.; Dommerholt, Jan; Guo, Jun; Ania, Daniel B.; Debets, Marjoke F.; Wolfert, Margreet A.; Boons, Geert-Jan et al. (2010). "Protein Modification by Strain-Promoted Alkyne-Nitrone Cycloaddition". Angewandte Chemie International Edition 49 (17): 3065), oxime/hydrazone formation from aldehydes and ketones, tetrazine ligations (see, e.g., Blackman, Melissa L.; Royzen, Maksim; Fox, Joseph M. (2008). "The Tetrazine Ligation: Fast Bioconjugation based on Inverse-electron-demand Diels-Alder Reactivity". Journal of the American Chemical Society 130 (41): 13518-9), tetrazole ligations, the isonitrile-based click reaction (see, e.g., Stackmann, Henning; Neves, AndrÃ© A.; Stairs, Shaun; Brindle, Kevin M.; Leeper, Finian J. (2011). "Exploring isonitrile-based click chemistry for ligation with biomolecules". Organic & Biomolecular Chemistry 9 (21): 7303), and the quadricyclane ligation (see, e.g., Sletten, Ellen M.; Bertozzi, Carolyn R. (2011). "A Bioorthogonal Quadricyclane Ligation". Journal of the American Chemical Society 133 (44): 17570-3). In certain embodiments a click chemistry reaction is a Staudinger ligation (phosphine-azide).

Any compstatin analog may be modified to incorporate a click chemistry group in various embodiments. For example, a compstatin analog comprising the sequence of any of SEQ ID NOs: 3-36, 37, 69, 70, 71, or 72 may be so modified. In some embodiments any such sequence further comprises a lysine residue or an AEEAc-Lys moiety, e.g., at the C-terminus. In some embodiments a click chemistry group is incorporated after peptide synthesis. For example, a Lys side chain may be reacted with azido acetic acid in order to introduce an azide moiety as a click chemistry group. In some embodiments a click chemistry group is incorporated after cyclization and, in some embodiments, after addition of a blocking moiety at the N- and/or C-terminus. In some embodiments a click chemistry group is incorporated during peptide synthesis. For example, an amino acid comprising a side chain that comprises a click chemistry group may be used in the synthesis of a compstatin analog. A variety of such amino acids are commercially available from a number of sources, e.g., AAPPTec (Louisville, KY), Jena Bioscience GmBH (Jena, Germany). In some aspects, methods of making a click chemistry functionalized compstatin analog are provided herein.

In some embodiments compositions comprising a compstatin analog and a click chemistry reagent are provided. The click chemistry reagent may be any molecule capable of reacting with an amino acid side chain or terminus of a compound comprising a compstatin analog so as to install a click chemistry group, e.g., any click chemistry group known in the art. In some aspects, the composition may be incubated under suitable conditions (which may include providing a suitable catalyst, light (e.g., UV)) to functionalize the compstatin analog with a click chemistry functionality. In some embodiments, the invention provides compstatin analogs that comprise any click chemistry group including, but not limited to, those described herein. In some embodiments methods of making a long-acting compstatin analog are provided. In some embodiments the methods comprise mixing a compstatin analog comprising a first click chemistry group with a CRM comprising a complementary click chemistry group under conditions suitable for a click chemistry reaction to occur. Additional steps may comprise purifying the resulting conjugate. In some embodiments purifying comprises removing at least some unreacted components, e.g., with an appropriate scavenger.

In some embodiments a click chemistry reaction is used to join two or more CRMs, at least two of which have a compstatin analog moiety attached thereto. The compstatin analog moieties may be the same or different in various embodiments. The compstatin analog moieties may or may not be attached to the CRM via a click chemistry reaction. For example, in some embodiments a first heterobifunctional PEG comprising a first click chemistry group at a first terminus and an NHS ester at a second terminus is coupled to a compstatin analog moiety via the NHS ester. In a separate reaction, a second heterobifunctional PEG comprising a second click chemistry group at a first terminus and an NHS ester at a second terminus is coupled to a compstatin analog moiety via the NHS ester. The resulting two compounds are then reacted via a click chemistry reaction to form a larger molecule comprising two compstatin analog moieties. PEG is mentioned as an example of a CRM but it should be understood that this approach may be used with any CRM. For example, in some embodiments it may be used with a CRM comprising a polypeptide, e.g., HSA or a portion thereof, or an albumin or albumin-binding peptide, or an antibody or portion thereof. In some embodiments this approach may be used with a POZ.

Compstatin analogs comprising a click chemistry group have a variety of uses. In some embodiments a compstatin analog comprising a first click chemistry group is reacted with any entity that comprises a complementary click chemistry group. The entity comprising the complementary click chemistry group may comprise, for example, a label (e.g., a flurophore, fluorescent protein, radioisotope, etc.), an affinity reagent, an antibody, a targeting moiety, a metal, a particle, etc. In some embodiments a click chemistry group is used to attach a compstatin analog moiety to a surface, wherein the surface comprises or is functionalized to comprise a complementary click chemistry group. In some embodiments a surface is for a sensor, e.g., a surface or sensor for capture/detection of C3. In some embodiments a surface forms part of a medical device, tubing, membrane, reservoir, implant, or other material that may come in contact with blood (e.g., extracorporeally) or be temporarily or indefinitely implanted into the body of a subject (e.g., a prosthetic device or drug delivery device). In some embodiments a surface is functionalized with compstatin analog to reduce complement activation thereon. In some embodiments a device or tubing is used for circulating blood, e.g., for dialysis, during surgery, etc. In some embodiments a device is a hemodialyzer or an extracorporeal circulatory support unit. Such compstatin analog functionalized devices and methods of making thereof are provided herein.

In some embodiments of the invention, a compstatin analog comprises both a cell-reactive functional group and a CRM. In some aspects, the invention provides variants of the molecules of any of the afore-mentioned cell-reactive compstatin analogs wherein a cell-reactive functional group or moiety is replaced by a $(CH_2CH_2O)_n$ moiety (e.g., any of the PEGs described herein) or other polymer (e.g., a POZ, a polypeptide) having a molecular weight of at least 500 daltons, e.g., at least 1,500 daltons up to about 100,000 daltons (e.g., an average molecular weight of about 20,000; 30,000; 40,000; 50,000; 60,000; 70,000; 80,000; 90,000; or 100,000 daltons). In some embodiments the average molecular weight of the compound or $(CH_2CH_2O)_n$ moieties (or other polymer, e.g., a POZ or polypeptide) is at least 20,000 daltons, up to about 100,000; 120,000; 140,000; 160,000; 180,000; or 200,000 daltons. It will thus be understood that the teachings herein regarding cell-reactive compstatin analogs, e.g., the compstatin analog moieties used and the linkages by which a compstatin analog moiety is attached to a cell-reactive moiety, can apply to long-acting compstatin analogs, and long-acting compstatin analog can have any of the structures denoted by A-L-M, as described above, wherein A comprises a clearance reducing moiety (e.g., any of the clearance reducing moieties described herein), and furthermore wherein there may be one, two, or more (e.g., 3, 4, 5, 6, 7, 8) compstatin analog moieties M attached to A via linking portions denoted as L (or $L^{P1}$, $L^{P2}$, or $L^{P3}$) herein). Compstatin analog moieties may comprise a peptide whose sequence comprises any of SEQ ID NOs: 3-36, 37, 69, 70, 71, or 72, or variants thereof (e.g., any variant described herein), optionally extended by one or more amino acids at the N-terminus, C-terminus, or both wherein at least one of the amino acids has a side chain that comprises a reactive functional group such as a primary or secondary amine (e.g., a Lys), a sulfhydryl group, a carboxyl group (which may be present as a carboxylate group), a guanidino group, a phenol group, an indole ring, a thioether, or an imidazole ring, which facilitates conjugation of a moiety comprising a CRM to the compstatin analog (it being understood that after conjugation, such reactive functional group will have reacted to form a bond). It will further be understood that where a compstatin analog moiety comprising any of SEQ ID NOs: 3-36, 37, 69, 70, 71, or 72, or variants thereof, is extended by one or more amino acids at the N-terminus, C-terminus, or both wherein at least one of the amino acids has a side chain that comprises a reactive functional group, such one or more amino acid extension may be separated from the cyclic portion of the compstatin analog moiety by a rigid or flexible spacer moiety comprising, for example, a substituted or unsubstituted, saturated or unsaturated alkyl chain, oligo (ethylene glycol) chain, and/or any of the other moieties denoted by L (or $L^{P1}$, $L^{P2}$, or $L^{P3}$) herein.

Exemplary long-acting compstatin analogs are set forth below, wherein n is sufficient to provide an average molecular weight of between about 500; 1,000; 1,500; 2,000; 5,000; 10,000; 20,000; 30,000; 40,000; 50,000; 60,000; 70,000; 80,000; 90,000; and 100,000 daltons. In some embodiments n is sufficient to provide an average molecular weight of between about 20,000 daltons, up to about 100,000; 120, 000; 140,000:160.000:180.000: or 200.000 daltons (SEQ ID NO: 58)
$(CH_2CH_2O)_nC(=O)$-Ile-Cys-Val-(1Me)Trp-Gln-Asp-Trp-Gly-Ala-His-Arg-Cys-Thr-$NH_2$)

(SEQ ID NO: 59)
Ac-Ile-Cys*-Val-(1Me)Trp-Gln-Asp-Trp-Gly-Ala-His-Arg-Cys*-Thr-NH—$CH_2CH_2OCH_2CH_2OCH_2$—C(=O)-Lys-C(=O)—$(CH_2CH_2O)n$—$NH_2$ (SEQ ID NO: 60)
Ac-Ile-Cys*-Val-(1Me)Trp-Gln-Asp-Trp-Gly-Ala-His-Arg-Cys*-Thr-Lys-C(=O)—$(CH_2CH_2O)n$—$NH_2$.

(SEQ ID NO: 61)
Ac-Ile-Cys*-Val-(1Me)Trp-Gln-Asp-Trp-Gly-Ala-His-Arg-Cys*-Thr-(Gly)5-Lys-C(=O)—$(CH_2CH_2O)n$—$NH_2$ (SEQ ID NO: 62)
Ac-$(CH_2CH_2O)nC(=O)$Lys-(Gly)5-Ile-Cys*-Val-(1Me)Trp-Gln-Asp-Trp-Gly-Ala-His-Arg-Cys*-Thr-$NH_2$)

-continued (SEQ ID NO: 63)
Ac-$(CH_2CH_2O)nC(=O)$Lys-Ile-Cys*-Val-(1Me)Trp-Gln-Asp-Trp-Gly-Ala-His-Arg-Cys*-Thr-$NH_2$)

In SEQ ID NO: 58, the $(CH_2CH_2O)_n$ is coupled via an amide bond to the N-terminal amino acid. In SEQ ID NOs: 59-63, the $(CH_2CH_2O)n$ moiety is coupled via an amide bond to a Lys side chain; thus it will be understood that the $NH_2$ at the C-terminus in SEQ ID NOs: 59, 60, and 61, represents amidation of the C-terminus of the peptide, and it will be understood that in SEQ ID NOs: 62 and 63, the Ac at the N-terminus represents acetylation of the N-terminus of the peptide, as described above. It will also be appreciated by those of ordinary skill in the art that a free end of a $(CH_2CH_2O)_n$ moiety typically terminates with an (<u>O</u>R) where the underlined O represents the O atom in the terminal $(CH_2CH_2O)$ group. (<u>O</u>R) is often a moiety such as a hydroxyl (<u>O</u>H) or methoxy (—<u>O</u>$CH_3$) group though other groups (e.g., other alkoxy groups) could be used. Thus SEQ ID NO: 59, for example, may be represented as Ac-Ile-Cys*-Val-(1Me) Trp-Gln-Asp-Trp-Gly-Ala-His-Arg-Cys*-Thr-NH—$CH_2CH_2OCH_2CH_2OCH_2$—C(=O)-Lys-(C(=O)—$(CH_2CH_2O)_n$—R)—$NH_2$ (SEQ ID NO: 64) wherein R is, e.g., either H or $CH_3$ in the case of a linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 64, in which the moiety comprising the reactive functional group comprises an ester and/or alkyl chain may be represented as follows (SEQ ID NO: 65)
Ac-Ile-Cys*-Val-(1Me)Trp-Gln-Asp-Trp-Gly-Ala-His-Arg-Cys*-Thr-NH-$CH_2CH_2OCH_2CH_2OCH_2$—C(=O)-Lys-(C(=O)—$(CH_2)_m$—$(CH_2CH_2O)_n$—R)—NH2;

(SEQ ID NO: 66)
Ac-Ile-Cys*-Val-(1Me)Trp-Gln-Asp-Trp-Gly-Ala-His-Arg-Cys*-Thr-NH-$CH_2CH_2OCH_2CH_2OCH_2$—C(=O)-Lys-(C(=O)-$(CH_2)_m$—C(=O)—$(CH_2CH_2O)_n$—R)—NH2

(SEQ ID NO: 67)
Ac-Ile-Cys*-Val-(1Me)Trp-Gln-Asp-Trp-Gly-Ala-His-Arg-Cys*-Thr-NH-$CH_2CH_2OCH_2CH_2OCH_2$—C(=O)-Lys-(C(=O)—$(CH_2)_m$—C(=O)—$(CH_2)_j$ $(CH_2CH_2O)_n$—R)—NH2

In SEQ ID NOs: 65-67 m may range from 1 up to about 2, 3, 4, 5, 6, 7, 8, 10, 15, 20, or 30 in various embodiments, In SEQ ID NOs: 67 j may range from 1 up to about 2, 3, 4, 5, 6, 7, 8, 10, 15, 20, or 30 in various embodiments.

It will also be appreciated that, as described herein, in various embodiments other moieties may be incorporated between the Lys-(C(=O)— and $(CH_2CH_2O)_n$-R, such as an amide, aromatic ring (e.g., a substituted or unsubstituted phenyl), or a substituted or unsubstituted cycloalkyl structure.

The invention provides variants of SEQ ID NOs: 58-67 in which-Ile-Cys*-Val-(1Me) Trp-Gln-Asp-Trp-Gly-Ala-His- Arg-Cys*-Thr- is replaced by an amino acid sequence comprising the amino acid sequence of any other compstatin analog, e.g., of any of SEQ ID NOS 3-27 or 29-36, 37, 69, 70, 71, or 72 with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-37, 69, 70, 71, or 72 may, in various embodiments, can be attached via or near its N-terminal or C-terminal end (e.g., via a side chain of an amino acid at or near its N-terminal or C-terminal amino acid) directly or indirectly to any moiety comprising a reactive functional group, e.g., any compound of Formulae I-XVI or Formulae A-H.

In some embodiments the CRM comprises a polypeptide that occurs in human serum, or a fragment thereof or a substantially similar variant of the polypeptide or fragment thereof. In some embodiments the polypeptide, fragment, or variant has a molecular weight of between 5 kD and 150 kD, e.g., at least 5, 10, 20, 30, 40, 50, 60, 70, 80, 90, 100 kd, or more, e.g., between 100 and 120, or 120 and 150 kD. In some embodiments, producing a long-acting compstatin analog comprises reacting a compstatin analog comprising a reactive functional group with one or more amino acid side chains of the polypeptide, wherein the side chain comprises a compatible functional group. In some embodiments, producing a long-acting compstatin analog comprises reacting a compstatin analog comprising a reactive functional group with the N-terminal amine and/or C-terminal carboxyl group of the polypeptide. In some embodiments, producing a long-acting compstatin analog comprises reacting a compstatin analog comprising an amine-reactive functional group with amino acids having a side chain comprising a primary amine (e.g., lysine) and/or with the N-terminal amine of the polypeptide. In some embodiments, producing a long-acting compstatin analog comprises reacting a compstatin analog comprising a carboxyl-reactive functional group with the C-terminal carboxyl group of the polypeptide. In some embodiments a compstatin analog moiety is attached at each terminus of the polypeptide and, optionally, to the side chain of one or more internal amino acids. In some embodiments, producing a long-acting compstatin analog comprises reacting a compstatin analog comprising a sulfhydryl-reactive functional group with one or more sulfhydryl groups of the polypeptide.

In some embodiments, at least one reactive functional group is introduced into the polypeptide. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or tris-(2-cyanoethyl) phosphine. Amines can be indirectly thiolated by reaction with succinimidyl 3-(2-pyridyldithio) propionate (SPDP) followed by reduction of the 3-(2-pyridyldithio) propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising one or more thiols may be reacted with a compstatin analog comprising a maleimide group, such as Ac-Ile-Cys*-Val-Trp(1-Me)-Gln-Asp-Trp-Gly-Ala-His-Arg-Cys*-Thr-AEEAc-Lys-(C(=O)—$(CH_2)_5$-Mal)—$NH_2$ (SEQ ID NO: 68) to generate a long-acting compstatin analog.

In some embodiments the polypeptide is recombinantly produced. In some embodiments the polypeptide is at least in part recombinantly produced (e.g., in bacteria or in eukaryotic host cells such as fungal, insect, plant, or vertebrate) and/or at least in part produced using chemical synthesis. In some embodiments the polypeptide is purified. For example, in some embodiments the polypeptide is purified from a host cell lysate or from culture medium into which it has been secreted by host cells. In some embodiments the polypeptide is glycosylated. In some embodiments the polypeptide is non-glycosylated. In some embodiments the polypeptide is human serum albumin (HSA). In some embodiments a substantially similar variant of the polypeptide is sufficiently similar to the polypeptide of which it is a variant so as to not be recognized as foreign by a normal immune system of a subject, e.g., a human subject. In some embodiments alterations in the sequence of substantially similar variant as compared with the polypeptide of which it is a variant are selected so as to avoid generating MHC Class I epitopes. Various methods known in the art can be used to predict whether a sequence comprises an MHC Class I epitope.

In some embodiments, one or more amino acids in a polypeptide or linker or composition may be selected to be hydrophobic or hydrophilic or selected to confer increased hydrophilicity or, in some embodiments, increased hydrophobicity, on a compound that contains it. As known in the art, the terms "hydrophilic" and "hydrophobic" are used to refer to the degree of affinity that a substance has with water. In some aspects a hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be classified based on their hydrophobicity as well known in the art. Examples of "hydrophilic amino acids" are arginine, lysine, threonine, alanine, asparagine, glutamine, aspartate, glutamate, serine, and glycine. Examples of "hydrophobic amino acids" are tryptophan, tyrosine, phenylalanine, methionine, leucine, isoleucine, and valine. In certain embodiments an analog of a standard amino acid is used, wherein the analog has increased or decreased hydrophilic or hydrophobic character as compared with the amino acid of which it is an analog.

The invention further provides multimers, e.g., concatamers, comprising two or more (e.g., between 2 and 10) compstatin analogs comprising a CRM, wherein the average molecular weight of the resulting molecule (or the CRM components thereof) is between 20,000; 30,000; 40,000; 50,000; 60,000; 70,000; 80,000; 90,000; and 100,000 daltons. In some embodiments the average molecular weight of the resulting molecule (or the CRM components thereof) is at least 20,000 daltons, up to about 100,000; 120,000; 140,000; 160,000; 180,000; or 200,000 daltons. In some embodiments, the compstatin analogs comprising a CRM can be linked using any of the linking moieties described above. Compositions and methods for making long-acting compstatin analogs, and intermediates in the synthesis, are aspects of the invention.

In some embodiments the total molecular weight of a long-acting compstatin analog, including the compstatin analog moieties, is no greater than 50 kD. For example, in the case of a LACA comprising a 40 kD PEG, in some embodiments the molecular weight contributed by the remainder of the compound, including the compstatin analog moie(ties), may be no greater than 10 kD, e.g., 1.5 kD-5.0 kD or 5.0 kD-10 kD. In some embodiments the total molecular weight of a LACA, including the compstatin analog moieties, is between 45 kD and 50 kD. In some embodiments the total molecular weight of a LACA, including the compstatin analog moieties, is between 40 kD and 45 kD, between 15 kD and 40 kD, e.g., between 15 kD and 25 kD, between 25 kD and 35 kD, between 35 kD and 40 kD. Thus, wherever the present disclosure refers to a compstatin analog comprising a polymer or CRM having a particular molecular weight, or having a molecular weight within a particular range, in some embodiments the total molecular weight of the compstatin analog may be, e.g., between 1.5 kD and 5 kD greater than the molecular weight of the polymer or CRM, or in some embodiments between 5 kD and 10 kD greater than the molecular weight of the polymer. It will be understood that molecular weight of a compound, e.g., a compound comprising a polymer, can refer to the average molecular weight of molecules of such compound in a composition.

A wide variety of methods and assays useful for detection of polymers, e.g., PEGs, POZs, and/or polypeptides and/or useful for measurement of physical and/or structural properties of polymers, e.g., PEGs, POZs, and/or polypeptides are known in the art and may, if desired, be used to detect a compstatin analog, e.g., a cell-reactive, long-acting, targeted compstatin analog or a compstatin analog moiety. For example, methods and assays useful for determining properties such as aggregation, solubility, size, structure, melting properties, purity, presence of degradation products or contaminants, water content, hydrodynamic radius, etc., are available. Such methods include, e.g., analytical centrifugation, various types of chromatography such as liquid chromatography (e.g., HPLC-ion exchange, HPLC-size exclusion, HPLC-reverse phase), light scattering, capillary electrophoresis, circular dichroism, isothermal calorimetry, differential scanning calorimetry, fluorescence, infrared (IR), nuclear magnetic resonance (NMR), Raman spectroscopy, refractometry, UV/Visible spectroscopy, mass spectrometry, immunological methods, etc. It will be understood that methods may be combined. In some aspects, a cell-reactive, long-acting, or targeted compstatin analog (or composition comprising a cell-reactive, long-acting, or targeted compstatin analog) has one or more properties described herein, as assessed using any of the foregoing methods. In some aspects, methods useful to detect and/or quantify a long-acting compstatin analog are described herein.

(iv) Targeted Compstatin Analogs

The invention provides and/or utilizes targeted compstatin analogs that comprise a targeting moiety and a compstatin analog moiety, wherein the targeting moiety binds non-covalently to a target molecule. In some aspects, the invention provides targeted compstatin analogs analogous to the cell-reactive compstatin analogs described herein, wherein the compounds comprise a targeting moiety in addition to, or instead of, a cell-reactive moiety. The targeting moiety can comprise, e.g., an antibody, polypeptide, peptide, nucleic acid (e.g., an aptamer), carbohydrate, small molecule, or supramolecular complex, that specifically binds to the target molecule. In some embodiments, the affinity (as measured by the equilibrium dissociation constant, Kd) of targeting moiety for the target molecule (as measured by the equilibrium dissociation constant, Kd) is $10^{-3}$ M or less, e.g., $10^{-4}$ M or less, e.g., $10^{-5}$ M or less, e.g., $10^{-6}$M or less, $10^{-7}$M or less, $10^{-8}$M or less, or $10^{-9}$ M or less under the conditions tested, e.g., under physiological conditions.

In those embodiments of the invention in which the targeting moiety is an antibody, the antibody may be any immunoglobulin or a derivative thereof, which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', $F(ab')_2$, scFv (single-chain variable) or other fragment that retains an antigen binding site, or a recombinantly produced scFv fragment, including recombinantly produced fragments. See, e.g., Allen, T., Nature Reviews Cancer, Vol. 2, 750-765, 2002, and references therein. Monovalent, bivalent or multivalent antibodies can be used. The antibody may be a chimeric antibody in which, for example, a variable domain of rodent origin is fused to a constant domain of human origin, thus retaining the specificity of the rodent antibody. In some embodiments, a human antibody or portion thereof is generated, for example, in rodents whose genome incorporates human immunoglobulin genes, using a display technology such as phage display, etc. In some embodiments, a humanized antibody is generated by grafting one or more complementarity determining region(s) from a non-human species (e.g., mouse) into a human antibody sequence. The antibody may be partially or completely humanized. See, e.g., Almagro J C, Fransson J.Humanization of antibodies. Front Biosci. 13:1619-33 (2008) for review of various methods of obtaining humanized antibodies that may be used to obtain a targeting moiety of use in the invention. An antibody may be polyclonal or monoclonal, though for purposes of the present invention monoclonal antibodies are generally preferred. In certain embodiments of the invention a F(ab')2 or F(ab') fragment is use while in other embodiments antibodies comprising an Fc domain are used. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture. Methods of generating antibody fragments, e.g., by digestion, disulfide reduction, or synthesis are known in the art.

In various embodiments of the invention a targeting moiety can be any molecule that specifically binds to a target molecule through a mechanism other than an antigen-antibody interaction. Such a targeting moiety is referred to as a "ligand". For example, in various embodiments of the invention a ligand can be a polypeptide, peptide, nucleic acid (e.g., DNA or RNA), carbohydrate, lipid or phospholipid, or small molecule. In some embodiments a small molecule is an organic compound, whether naturally-occurring or artificially created, that has relatively low molecular weight and is not a protein, polypeptide, nucleic acid, or lipid, typically with a molecular weight of less than about 1500 g/mol and typically having multiple carbon-carbon bonds. In general, an aptamer is an oligonucleotide (e.g., RNA or DNA, optionally comprising one or more modified nucleosides (e.g., bases or sugars other than the 5 standard bases (A, G, C, T, U) or sugars (ribose and deoxyribose) found most commonly in RNA and DNA), or modified internucleoside linkages (e.g., non-phosphodiester bonds) that, e.g., stabilize the molecule, e.g., by rendering it more resistant to degradation by nucleases) that binds to a particular protein. In some embodiments an oligonucleotide is up to about 100 nucleosides long, e.g., between 12 and 100 nucleosides long. Aptamers can be derived using an in vitro evolution process called SELEX, and methods for obtaining aptamers specific for a protein of interest are known in the art. See, e.g., Brody E N, Gold L. J Biotechnol. 2000 March; 74 (1): 5-13. In some embodiments, a peptide nucleic acid or locked nucleic acid is used.

In certain embodiments of the invention a targeting moiety comprises a peptide. In some embodiments a peptide that binds to a target molecule of interest is identified using a display technology such as phage display, ribosome display, yeast display, etc.

Small molecules can be used as ligands. Methods for identifying such ligands are known in the art. For example in vitro screening of small molecule libraries, including combinatorial libraries, and computer-based screening, e.g., to identify small organic compounds that bind to concave surfaces (pockets) of proteins, can identify small molecule ligands for numerous proteins of interest (Huang, Z., Pharm. & Ther. 86:201-215, 2000).

In certain embodiments of the invention targeting moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In certain embodiments of the invention the targeting moiety is not an Fc portion of an immunoglobulin molecule. In some embodiments, a targeting moiety is part of a complex comprising one or more additional moieties to which it is covalently or noncovalently attached.

In various embodiments of the invention a target molecule can be any molecule produced by a cell (including any forms expressed on the cell surface or modified forms thereof resulting at least in part from extracellular modification). In some embodiments a target molecule is an extracellular substance present in or on a tissue. In some embodiments, a target molecule is characteristic of a particular diseased or physiological state or characteristic of one or more cell type(s) or tissue type(s). A target molecule is often a molecule at least partly present at the cell surface (e.g., a transmembrane or otherwise membrane-attached protein) so that at least a portion of the molecule is accessible to binding by an extracellular binding agent such as an antibody. A target molecule may, but need not be, cell type specific. For example, a cell type specific target molecule is often a protein, peptide, mRNA, lipid, or carbohydrate that is present at a higher level on or in a particular cell type or cell type(s) than on or in many other cell types. In some instances a cell type specific target molecule is present at detectable levels only on or in a particular cell type of interest. However, it will be appreciated that a useful cell type specific target molecule need not be absolutely specific for the cell type of interest in order to be considered cell type specific. In some embodiments, a cell type specific target molecule for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. In some embodiments, the cell type specific target molecule is present at levels at least 4-5 fold, between 5-10 fold, or more than 10-fold greater than its average expression in a reference population. In some embodiments, detection or measurement of a cell type specific target molecule allows one of ordinary skill in the art to distinguish a cell type or types of interest from cells of many, most, or all other types. In general, the presence and/or abundance of most target molecules may be determined using one or more standard techniques such as Northern blotting, in situ hybridization, RT-PCR, sequencing, immunological methods such as immunoblotting, immunodetection (e.g., by immunohistochemistry), or fluorescence detection following staining with fluorescently labeled antibodies (e.g., using FACS), oligonucleotide or cDNA microarray or membrane array, protein microarray analysis, mass spectrometry, etc.

In some embodiments, a target molecule is a channel, transporter, receptor, or other molecule at least in part exposed at the cell surface. In some embodiments a target molecule is an anion transporter or water channel (e.g., an aquaporin protein).

In some embodiments, the target molecule is a protein at least in part exposed at the surface of red blood cells, such as a glycophorin (e.g., glycophorin A, B, C, or D) or band 3.

In some embodiments, the target molecule is a protein at least in part exposed at the surface of endothelial cells. In some embodiments, the target molecule is present at the surface of normal, healthy vasculature. In some embodiments, the target molecule is present at the surface of activated endothelial cells. In some embodiments, the target molecule is present at the surface of activated endothelial cells but not at the surface of non-activated endothelial cells. In some embodiments a target molecule is a molecule whose expression or exposure is induced by a stimulus such as injury or inflammation. In some embodiments, a target molecule would be recognized as "non-self" by a recipient receiving a transplant containing cells that express the target molecule. In some embodiments, the target molecule is a carbohydrate xenoantigen to which antibodies are commonly found in human beings. In some embodiments the carbohydrate comprises a blood group antigen. In some embodiments the carbohydrate comprises a xenoantigen, e.g., an alpha-gal epitope (Galalpha1-3Galbeta1-(3) 4GlcNAc-R) (see, e.g., Macher B A and Galili U. The Galalpha1, 3Galbeta1, 4GlcNAc-R (alpha-Gal) epitope: a carbohydrate of unique evolution and clinical relevance. Biochim Biophys Acta. 1780 (2): 75-88 (2008).

In some embodiments of the invention, a compstatin analog comprises both a targeting moiety and a CRM.

In some embodiments, a targeted compstatin analog comprises multiple targeting moieties, which can be the same or different. Different targeting moieties may bind to the same target molecule or to different target molecules. The invention provides a targeted compstatin analog that is multivalent with respect to the targeting moiety, the compstatin analog, or both.

In general, the invention encompasses any method of producing a compound comprising a compstatin analog moiety and a targeting moiety, and the resulting compounds.

In some embodiments, a targeted compstatin analog may be produced using methods generally similar to those described herein, wherein a targeting moiety is used instead of, or in addition to, a cell-reactive moiety. In some embodiments, a targeted compstatin analog comprising a peptide as a targeting moiety is synthesized as a polypeptide chain comprising a compstatin analog moiety and a peptide targeting moiety. Optionally, the polypeptide chain comprises one or more spacer peptides between the compstatin analog moiety and the targeting moiety.

In some embodiments, a targeted compstatin analog has a molar activity of at least about 10%, 20%, or 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a targeting moiety. In some embodiments wherein a targeted compstatin analog comprises multiple compstatin analog moieties, the molar activity of the targeted compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. Compositions and methods for making targeted compstatin analogs, and intermediates in the synthesis, are aspects of the invention.

(v) Antibodies

The present disclosure also contemplates using antibodies that inhibit complement activation. Such an antibody can bind to and inhibit one or more complement pathway proteins. In some embodiments, complement activation may be inhibited by inhibiting C3 or C5 activation. C3 or C5 dependent complement activation may be inhibited by a C3 or C5 complement inhibitor. Exemplary agents may comprise an antibody or an antibody fragment. In some embodiments, an antibody may bind to C3 or C5. In some embodiments, an antibody fragment may be used to inhibit C3 or C5 activation. The fragmented anti-C3 or anti-C5 antibody may be Fab', Fab' (2), Fv, or single chain Fv. In some embodiments, the anti-C3 or anti-C5 antibody is monoclonal. In some embodiments, the anti-C3 or anti-C5 antibody is polyclonal. In some embodiments, the anti-C3 or anti-C5 antibody is de-immunized. In some embodiments the anti-C3 or anti-C5 antibody is a fully human monoclonal antibody. In some embodiments, the anti-C5 antibody is eculizumab.

In some embodiments, the anti-C3 or anti-C5 antibody (or anti-C3 or anti-C5 antibody fragment) may bind to C3 or C5 to inhibit complement activation. In some embodiments, the anti-C3 or anti-C5 antibody (or anti-C3 or anti-C5 antibody fragment) may bind to C3 or C5 fragments to inhibit complement activation. In some embodiments, a C3 fragment is C3b.

(vi) MicroRNAs

The present disclosure also contemplates using microRNAs that inhibit complement activation. MicroRNAs (miRNAs) are a highly conserved class of small RNA molecules that are transcribed from DNA in the genomes of plants and animals, but are not translated into protein. Naturally occurring miRNAs are first transcribed as long hairpin-containing primary transcripts (pri-miRNAs). The primary transcript is cleaved by Drosha ribonuclease III enzyme to produce an approximately 70 nt stem-loop precursor miRNA (pre-miRNA), which includes an "antisense strand" or "guide strand" (that includes a region that is substantially complementary to a target sequence) and a "sense strand" or "passenger strand" (that includes a region that is substantially complementary to a region of the antisense strand). The pre-miRNA is then actively exported to the cytoplasm where it is cleaved by Dicer ribonuclease to form the mature miRNA. Processed microRNAs are incorporated into the RNA-induced silencing complex (RISC) to form mature gene-silencing complexes, which induce target mRNA degradation and/or translation repression. The number of miRNA sequences identified to date is large and growing, illustrative examples of which can be found, for example, in: "*miRBase: microRIVA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111.

In some embodiments, miRNAs can be synthesized and locally or systemically administered to a subject, e.g., for therapeutic purposes. miRNAs can be designed and/or synthesized as mature molecules or precursors (e.g., pri- or pre-miRNAs). In some embodiments, a pre-miRNA includes a guide strand and a passenger strand that are the same length (e.g., about 15, 16, 17, 18, 19, 20, 21, 22, 23, 24, or 25 nucleotides). In some embodiments, a pre-miRNA includes a guide strand and a passenger strand that are different lengths (e.g., one strand is about 19 nucleotides, and the other is about 21 nucleotides). In some embodiments, an miRNA can target the coding region, the 5' untranslated region, and/or 3' untranslated region, of endogenous mRNA. In some embodiments, an miRNA comprises a guide strand comprising a nucleotide sequence having sufficient sequence complementary with an endogenous mRNA of a subject to hybridize with and inhibit expression of the endogenous mRNA.

In some embodiments, an miRNA comprises a nucleic acid strand that is complementary to a target portion of a C3 transcript, e.g., C3 mRNA (e.g., complementary to a nucleotide sequence that is at least 90%, 91%, 92%, 93%, 94%, 95%, 96%, 97%, 98%, 99%, or 100% identical to a portion of SEQ ID NO:75). The target portion may be 15-30 nucleotides long, e.g., 15, 16, 17, 18, 19, 20, 21, 22, 23, 24, 25, 26, 27, 28, 29, or 30 nucleotides long, although shorter and longer target portions are also contemplated. Human C3 is of particular interest herein. In some embodiments, the miRNA comprises a nucleic acid strand that comprises a region that is perfectly complementary to at least 6, 7, 8, 9, 10, 11, 12, 13 14, 15, 16, 17, 18, 19, 20, 21, 22, 23, 24, 25, 26, 27, 28, 29, or 30 consecutive nucleotides of SEQ ID NO: 75. The amino acid and nucleotide sequences of human C3 are known in the art and can be found in publicly available databases, for example, the National Center for Biotechnology Information (NCBI) Reference Sequence (RefSeq) database, where they are listed under RefSeq accession numbers NP_000055 (current accession.version number NP_000055.2) and NM_000064 (current accession.version number NM_000064.3), respectively (where "amino acid sequence" refers to the sequence of the C3 polypeptide and "nucleotide sequence" in this context refers to the C3 mRNA sequence as represented in genomic DNA, it being understood that the actual mRNA nucleotide sequence contains U rather than T). One of ordinary skill in the art will appreciate that the afore-mentioned sequences are for the complement C3 preproprotein, which includes a signal sequence that is cleaved off and is therefore not present in the mature protein. The human C3 gene has been assigned NCBI Gene ID: 718, and the genomic C3 sequence has RefSeq accession number NG_009557 (current accession- .version number NG_009557.1). The nucleotide sequence of human C3 mRNA is presented below (from RefSeq accession number NM_000064.3 with T replaced by U; AUG initiation codon underlined starting at position 94).

(SEQ ID NO: 75)

AGAUAAAAAGCCAGCUCCAGCAGGCGCUGCUCACUCCUCCCCAUCCUC

UCCCUCUGUCCCUCUGUCCCUCUGACCCUGCACUGUCCCAGCACCAUG

GGACCCACCUCAGGUCCCAGCCUGCUGCUCCUGCUACUAACCCACCUC

CCCCUGGCUCUGGGGAGUCCCAUGUACUCUAUCAUCACCCCCAACAUC

UUGCGGCUGGAGAGCGAGGAGACCAUGGUGCUGGAGGCCCACGACGCG

CAAGGGGAUGUUCCAGUCACUGUUACUGUCCACGACUUCCCAGGCAAA

AAACUAGUGCUGUCCAGUGAGAAGACUGUGCUGACCCCUGCCACCAAC

CACAUGGGCAACGUCACCUUCACGAUCCCAGCCAACAGGGAGUUCAAG

UCAGAAAAGGGGCGCAACAAGUUCGUGACCGUGCAGGCCACCUUCGGG

ACCCAAGUGGUGGAGAAGGUGGUGCUGGUCAGCCUGCAGAGCGGGUAC

CUCUUCAUCCAGACAGACAAGACCAUCUACACCCCUGGCUCCACAGUU

CUCUAUCGGAUCUUCACCGUCAACCACAAGCUGCUACCCGUGGGCCGG

ACGGUCAUGGUCAACAUUGAGAACCCGGAAGGCAUCCCGGUCAAGCAG

GACUCCUUGUCUUCUCAGAACCAGCUUGGCGUCUUGCCCUUGUCUUGG

GACAUUCCGGAACUCGUCAACAUGGGCCAGUGGAAGAUCCGAGCCUAC

UAUGAAAACUCACCACAGCAGGUCUUCUCCACUGAGUUUGAGGUGAAG

GAGUACGUGCUGCCCAGUUUCGAGGUCAUAGUGGAGCCUACAGAGAAA

UUCUACUACAUCUAUAACGAGAAGGGCCUGGAGGUCACCAUCACCGCC

AGGUUCCUCUACGGGAAGAAAGUGGAGGGAACUGCCUUUGUCAUCUUC

GGGAUCCAGGAUGGCGAACAGAGGAUUUCCCUGCCUGAAUCCCUCAAG

CGCAUUCCGAUUGAGGAUGGCUCGGGGGAGGUUGUGCUGAGCCGGAAG

GUACUGCUGGACGGGGUGCAGAACCCCCGAGCAGAAGACCUGGUGGGG

AAGUCUUUGUACGUGUCUGCCACCGUCAUCUUGCACUCAGGCAGUGAC

AUGGUGCAGGCAGAGCGCAGCGGGAUCCCCAUCGUGACCUCUCCCUAC

CAGAUCCACUUCACCAAGACACCCAAGUACUUCAAACCAGGAAUGCCC

UUUGACCUCAUGGUGUUCGUGACGAACCCUGAUGGCUCUCCAGCCUAC

CGAGUCCCCGUGGCAGUCCAGGGCGAGGACACUGUGCAGUCUCUAACC

CAGGGAGAUGGCGUGGCCAAACUCAGCAUCAACACACACCCCAGCCAG

AAGCCCUUGAGCAUCACGGUGCGCACGAAGAAGCAGGAGCUCUCGGAG

GCAGAGCAGGCUACCAGGACCAUGCAGGCUCUGCCCUACAGCACCGUG

GGCAACUCCAACAAUUACCUGCAUCUCUCAGUGCUACGUACAGAGCUC

AGACCCGGGGAGACCCUCAACGUCAACUUCCUCCUGCGAAUGGACCGC

GCCCACGAGGCCAAGAUCCGCUACUACACCUACCUGAUCAUGAACAAG

GGCAGGCUGUUGAAGGCGGGACGCCAGGUGCGAGAGCCCGGCCAGGAC

CUGGUGGUGCUGCCCCUGUCCAUCACCACCGACUUCAUCCCUUCCUUC

CGCCUGGUGGCGUACUACACGCUGAUCGGUGCCAGCGGCCAGAGGGAG

GUGGUGGCCGACUCCGUGUGGGUGGACGUCAAGGACUCCUGCGUGGGC

-continued

UCGCUGGUGGUAAAAAGCGGCCAGUCAGAAGACCGGCAGCCUGUACCU

GGGCAGCAGAUGACCCUGAAGAUAGAGGGUGACCACGGGGCCCGGGUG

GUACUGGUGGCCGUGGACAAGGGCGUGUUCGUGCUGAAUAAGAAGAAC

AAACUGACGCAGAGUAAGAUCUGGGACGUGGUGGAGAAGGCAGACAUC

GGCUGCACCCCGGGCAGUGGGAAGGAUUACGCCGGUGUCUUCUCCGAC

GCAGGGCUGACCUUCACGAGCAGCAGUGGCCAGCAGACCGCCCAGAGG

GCAGAACUUCAGUGCCCGCAGCCAGCCGCCCGCCGACGCCGUUCCGUG

CAGCUCACGGAGAAGCGAAUGGACAAAGUCGGCAAGUACCCCAAGGAG

CUGCGCAAGUGCUGCGAGGACGGCAUGCGGGAGAACCCCAUGAGGUUC

UCGUGCCAGCGCCGGACCCGUUUCAUCUCCCUGGGCGAGGCGUGCAAG

AAGGUCUUCCUGGACUGCUGCAACUACAUCACAGAGCUGCGGCGGCAG

CACGCGCGGGCCAGCCACCUGGGCCUGGCCAGGAGUAACCUGGAUGAG

GACAUCAUUGCAGAAGAGAACAUCGUUUCCCGAAGUGAGUUCCCAGAG

AGCUGGCUGUGGAACGUUGAGGACUUGAAAGAGCCACCGAAAAAUGGA

AUCUCUACGAAGCUCAUGAAUAUAUUUUUGAAAGACUCCAUCACCACG

UGGGAGAUUCUGGCUGUGAGCAUGUCGGACAAGAAAGGGAUCUGUGUG

GCAGACCCCUUCGAGGUCACAGUAAUGCAGGACUUCUUCAUCGACCUG

CGGCUACCCUACUCUGUUGUUCGAAACGAGCAGGUGGAAAUCCGAGCC

GUUCUCUACAAUUACCGGCAGAACCAAGAGCUCAAGGUGAGGGUGGAA

CUACUCCACAAUCCAGCCUUCUGCAGCCUGGCCACCACCAAGAGGCGU

CACCAGCAGACCGUAACCAUCCCCCCCAAGUCCUCGUUGUCCGUUCCA

UAUGUCAUCGUGCCGCUAAAGACCGGCCUGCAGGAAGUGGAAGUCAAG

GCUGCUGUCUACCAUCAUUUCAUCAGUGACGGUGUCAGGAAGUCCCUG

AAGGUCGUGCCGGAAGGAAUCAGAAUGAACAAAACUGUGGCUGUUCGC

ACCCUGGAUCCAGAACGCCUGGGCCGUGAAGGAGUGCAGAAAGAGGAC

AUCCCACCUGCAGACCUCAGUGACCAAGUCCCGGACACCGAGUCUGAG

ACCAGAAUUCUCCUGCAAGGGACCCCAGUGGCCCAGAUGACAGAGGAU

GCCGUCGACGCGGAACGGCUGAAGCACCUCAUUGUGACCCCCUCGGGC

UGCGGGGAACAGAACAUGAUCGGCAUGACGCCCACGGUCAUCGCUGUG

CAUUACCUGGAUGAAACGGAGCAGUGGGAGAAGUUCGGCCUAGAGAAG

CGGCAGGGGGCCUUGGAGCUCAUCAAGAAGGGGUACACCCAGCAGCUG

GCCUUCAGACAACCCAGCUCUGCCUUUGCGGCCUUCGUGAAACGGGCA

CCCAGCACCUGGCUGACCGCCUACGUGGUCAAGGUCUUCUCUCUGGCU

GUCAACCUCAUCGCCAUCGACUCCCAAGUCCUCUGCGGGGCUGUUAAA

UGGCUGAUCCUGGAGAAGCAGAAGCCCGACGGGGUCUUCCAGGAGGAU

GCGCCCGUGAUACACCAAGAAAUGAUUGGUGGAUUACGGAACAACAAC

GAGAAAGACAUGGCCCUCACGGCCUUUGUUCUCAUCUCGCUGCAGGAG

GCUAAAGAUAUUUGCGAGGAGCAGGUCAACAGCCUGCCAGGCAGCAUC

ACUAAAGCAGGAGACUUCCUUGAAGCCAACUACAUGAACCUACAGAGA

UCCUACACUGUGGCCAUUGCUGGCUAUGCUCUGGCCCAGAUGGGCAGG

CUGAAGGGGCCUCUUCUUAACAAAUUUCUGACCACAGCCAAAGAUAAG

-continued

AACCGCUGGGAGGACCCUGGUAAGCAGCUCUACAACGUGGAGGCCACA

UCCUAUGCCCUCUUGGCCCUACUGCAGCUAAAAGACUUUGACUUUGUG

CCUCCCGUCGUGCGUUGGCUCAAUGAACAGAGAUACUACGGUGGUGGC

UAUGGCUCUACCCAGGCCACCUUCAUGGUGUUCCAAGCCUUGGCUCAA

UACCAAAAGGACGCCCCUGACCACCAGGAACUGAACCUUGAUGUGUCC

CUCCAACUGCCCAGCCGCAGCUCCAAGAUCACCCACCGUAUCCACUGG

GAAUCUGCCAGCCUCCUGCGAUCAGAAGAGACCAAGGAAAAUGAGGGU

UUCACAGUCACAGCUGAAGGAAAAGGCCAAGGCACCUUGUCGGUGGUG

ACAAUGUACCAUGCUAAGGCCAAAGAUCAACUCACCUGUAAUAAAUUC

GACCUCAAGGUCACCAUAAAACCAGCACCGGAAACAGAAAAGAGGCCU

CAGGAUGCCAAGAACACUAUGAUCCUUGAGAUCUGUACCAGGUACCGG

GGAGACCAGGAUGCCACUAUGUCUAUAUUGGACAUAUCCAUGAUGACU

GGCUUUGCUCCAGACACAGAUGACCUGAAGCAGCUGGCCAAUGGUGUU

GACAGAUACAUCUCCAAGUAUGAGCUGGACAAAGCCUUCUCCGAUAGG

AACACCCUCAUCAUCUACCUGGACAAGGUCUCACACUCUGAGGAUGAC

UGUCUAGCUUUCAAAGUUCACCAAUACUUUAAUGUAGAGCUUAUCCAG

CCUGGAGCAGUCAAGGUCUACGCCUAUUACAACCUGGAGGAAAGCUGU

ACCCGGUUCUACCAUCCGGAAAAGGAGGAUGGAAAGCUGAACAAGCUC

UGCCGUGAUGAACUGUGCCGCUGUGCUGAGGAGAAUUGCUUCAUACAA

AAGUCGGAUGACAAGGUCACCCUGGAAGAACGGCUGGACAAGGCCUGU

GAGCCAGGAGUGGACUAUGUGUACAAGACCCGACUGGUCAAGGUUCAG

CUGUCCAAUGACUUUGACGAGUACAUCAUGGCCAUUGAGCAGACCAUC

AAGUCAGGCUCGGAUGAGGUGCAGGUUGGACAGCAGCGCACGUUCAUC

AGCCCCAUCAAGUGCAGAGAAGCCCUGAAGCUGGAGGAGAAGAAACAC

UACCUCAUGUGGGGUCUCUCCUCCGAUUUCUGGGGAGAGAAGCCCAAC

CUCAGCUACAUCAUCGGGAAGGACACUUGGGUGGAGCACUGGCCCGAG

GAGGACGAAUGCCAAGACGAAGAGAACCAGAAACAAUGCCAGGACCUC

GGCGCCUUCACCGAGAGCAUGGUUGUCUUUGGGUGCCCCAACUGACCA

CACCCCCAUUCCCCCACUCCAGAUAAAGCUUCAGUUAUAUCUCAAAAA

AAAAAAAAAAA

In some embodiments an miRNA is capable of inhibiting expression of C3 of one or more non-human species, e.g., a non-human primate C3, e.g., *Macaca fascicularis* C3, in addition to human C3. The *Macaca fascicularis* C3 gene has been assigned NCBI Gene ID: 102131458 and the predicted amino acid and nucleotide sequence of *Macaca fascicularis* C3 are listed under NCBI RefSeq accession numbers XP_005587776.1 and XM_005587719.2, respectively. In some embodiments, an miRNA is complementary to a target portion that is identical in the human and *Macaca fascicularis* C3 transcripts. In some embodiments, an miRNA is complementary to a target portion of a human C3 transcript that differs by 1, 2, or 3 nucleotides from a sequence in a *Macaca fascicularis* C3 transcript. It will be appreciated that an miRNA that inhibits expression of human C3 may also inhibit expression of non-primate C3, e.g., rat or mouse C3, particularly if conserved regions of C3 transcript are targeted.

(vii) siRNAs

RNA interference (RNAi) is a process of sequence-specific post-transcriptional gene silencing by which, e.g., double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing can be mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). RNAi can involve the use of, e.g., siRNAs (Elbashir, et al., Nature 2001; 411:494-498) or short hairpin RNAs (shRNAs) bearing a fold back stem-loop structure (Paddison et al., Genes Dev. 2002; 16:948-958; Sui et al., Proc. Natl. Acad. Sci. USA 2002; 99:5515-5520; Brummelkamp et al., Science 2002; 296: 550-553; Paul et al., Nature Biotechnol. 2002; 20:505-508).

The disclosure includes siRNA molecules targeting C3 transcript, e.g., C3 mRNA (SEQ ID NO: 75). In some embodiments, siRNAs of the disclosure are double stranded nucleic acid duplexes (of, e.g., 15, 16, 17, 18, 19, 20, 21, 22, 23, 24, 25, 26, or 27 base pairs) comprising annealed complementary single stranded nucleic acid molecules. In some embodiments, the siRNAs are short dsRNAs comprising annealed complementary single strand RNAs. In some embodiments, the siRNAs comprise an annealed RNA:DNA duplex, wherein the sense strand of the duplex is a DNA molecule and the antisense strand of the duplex is a RNA molecule.

In some embodiments, duplexed siRNAs comprise a 2 or 3 nucleotide 3' overhang on each strand of the duplex. In some embodiments, siRNAs comprise 5'-phosphate and 3'-hydroxyl groups.

In some embodiments, an siRNA molecule of the disclosure includes one or more natural nucleobase and/or one or more modified nucleobases derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Exemplary modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313.

Modified nucleobases also include expanded-size nucleobases in which one or more aryl rings, such as phenyl rings, have been added. Nucleic base replacements described in the Glen Research catalog (www.glenresearch.com); Krueger A T et al, Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for siRNA molecules described herein. Modified nucleobases also encompass structures that are not considered nucleobases but are other moieties such as, but not limited to, corrin- or porphyrin-derived rings. Porphyrin-derived base replacements have been described in Morales-Rojas, H and Kool, E T, Org. Lett., 2002, 4, 4377-4380.

In some embodiments, modified nucleobases are of any one of the following structures, optionally substituted:

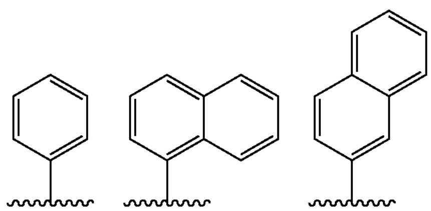
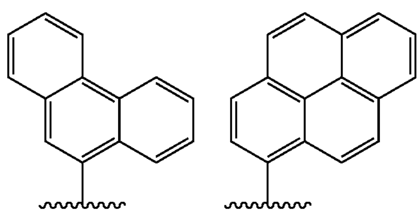
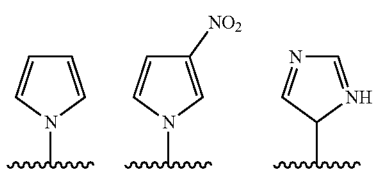

In some embodiments, a modified nucleobase is fluorescent. Exemplary such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

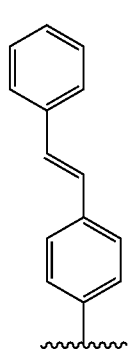
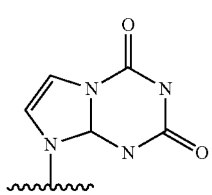
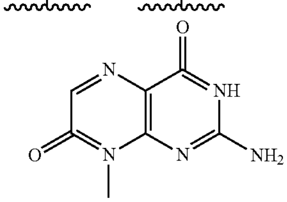
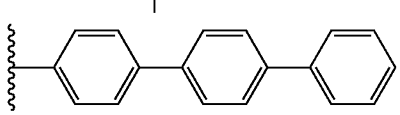
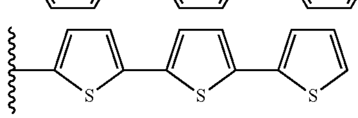

-continued

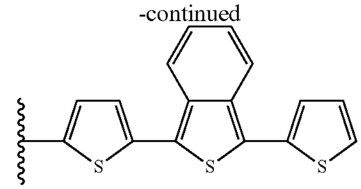
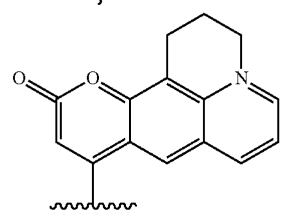
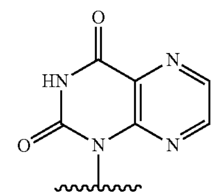
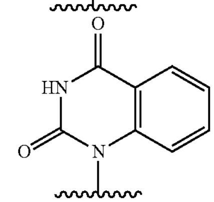
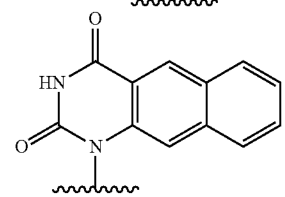
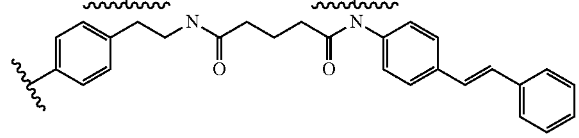

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, siRNA molecules described herein include nucleosides that incorporate modified nucleobases and/or nucleobases covalently bound to modified sugars. Some examples of nucleosides that incorporate modified nucleobases include 4-acetylcytidine; 5-(carboxyhydroxylmethyl) uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in U.S. Publ. No. 20070287831. In some embodiments, a nucleobase or modified nucleobase is 5-bromouracil, 5-iodouracil, or 2,6-diaminopurine. In some embodiments, a nucleobase or modified nucleobase is modified by substitution with a fluorescent moiety.

Methods of preparing modified nucleobases are described in, e.g., U.S. Pat. Nos. 3,687,808; 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088.

In some embodiments, an siRNA molecule described herein includes one or more modified nucleotides wherein a phosphate group or linkage phosphorus in the nucleotides are linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context.

Other modified sugars can also be incorporated within an siRNA molecule. In some embodiments, a modified sugar contains one or more substituents at the 2' position including one of the following: —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)—O—($C_1$-$C_{10}$ alkyl), —O—($C_1$-$C_{10}$ alkylene)—NH—($C_1$-$C_{10}$ alkyl) or —O—($C_1$-$C_{10}$ alkylene)—NH ($C_1$-$C_{10}$ alkyl$)_2$, —NH—($C_1$-$C_{10}$ alkylene)—O—($C_1$-$C_{10}$ alkyl), or —N($C_1$-$C_{10}$ alkyl)-($C_1$-$C_{10}$ alkylene)—O—($C_1$-$C_{10}$ alkyl), wherein the alkyl, alkylene, alkenyl and alkynyl may be substituted or unsubstituted. Examples of substituents include, and are not limited to, —O $(CH_2)$,$OCH_3$, and-O $(CH_2)_nNH_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'—OH of a ribose is replaced with a substituent including one of the following: —H, —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_2$-$C_{10}$ alkenyl), — NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)—O—($C_1$-$C_{10}$ alkyl), —O—($C_1$-$C_{10}$ alkylene)—NH—($C_1$-$C_{10}$ alkyl) or —O—($C_1$-$C_{10}$ alkylene)—NH ($C_1$-$C_{10}$ alkyl$)_2$, —NH—($C_1$-$C_{10}$ alkylene)—O—($C_1$-$C_{10}$ alkyl), or —N($C_1$-$C_{10}$ alkyl)-($C_1$-$C_{10}$ alkylene)—O—($C_1$-$C_{10}$ alkyl), wherein the alkyl, alkylene, alkenyl and alkynyl may be substituted or unsubstituted. In some embodiments, the 2'—OH is replaced with —H (deoxyribose). In some embodiments, the 2'—OH is replaced with —F. In some embodiments, the 2'—OH is replaced with —OR'. In some embodiments, the 2'—OH is replaced with —OMe. In some embodiments, the 2'—OH is replaced with —$OCH_2CH_2OMe$.

Modified sugars also include locked nucleic acids (LNAs). In some embodiments, the locked nucleic acid has the structure indicated below. A locked nucleic acid of the structure below is indicated, wherein Ba represents a nucleobase or modified nucleobase as described herein, and wherein $R^{2s}$ is —$OCH_2C4'$—

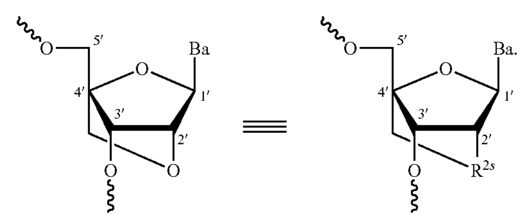

C2'$OCH_2C4'$ = LNA (Locked Nucleic Acid)

$R^{2s}$ = $OCH_2C4'$

In some embodiments, a modified sugar is an ENA such as those described in, e.g., Seth et al., J Am Chem Soc. 2010 Oct. 27; 132 (42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar (see, e.g., U.S. Pat. Nos. 4,981,957; 5,118,800; 5,319,080; and 5,359,044). Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603. Another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413. Additional non-limiting examples of modified sugars include hexopyranosyl (6' to 4'), pentopyranosyl (4' to 2'), pentopyranosyl (4' to 3'), or tetrofuranosyl (3' to 2') sugars.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J.

Am. Chem. Soc. (2006), 128 (33): 10847-56; A. Eschenmoser in Chemical Synthesis: Gnosis to Prognosis, C. Chatgilialoglu and V. Sniekus, Ed., (Kluwer Academic, Netherlands, 1996), p.293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310); PCT Publication No. WO2012/030683.

In some embodiments, an siRNA described herein can be introduced to a target cell as an annealed duplex siRNA. In some embodiments, an siRNA described herein is introduced to a target cell as single stranded sense and antisense nucleic acid sequences that, once within the target cell, anneal to form an siRNA duplex. Alternatively, the sense and antisense strands of the siRNA can be encoded by an expression vector (such as an expression vector described herein) that is introduced to the target cell. Upon expression within the target cell, the transcribed sense and antisense strands can anneal to reconstitute the siRNA.

An siRNA molecule described herein can be synthesized by standard methods known in the art, e.g., by use of an automated synthesizer. RNAs produced by such methodologies tend to be highly pure and to anneal efficiently to form siRNA duplexes. Following chemical synthesis, single stranded RNA molecules can be deprotected, annealed to form siRNAs, and purified (e.g., by gel electrophoresis or HPLC). Alternatively, standard procedures can be used for in vitro transcription of RNA from DNA templates, e.g., carrying one or more RNA polymerase promoter sequences (e.g., T7 or SP6 RNA polymerase promoter sequences). Protocols for preparation of siRNAs using T7 RNA polymerase are known in the art (see, e.g., Donze and Picard, Nucleic Acids Res. 2002; 30: e46; and Yu et al., Proc. Natl. Acad. Sci. USA 2002; 99:6047-6052). The sense and antisense transcripts can be synthesized in two independent reactions and annealed later, or they can be synthesized simultaneously in a single reaction.

An siRNA molecule can also be formed within a cell by transcription of RNA from an expression construct introduced into the cell (see, e.g., Yu et al., Proc. Natl. Acad. Sci. USA 2002; 99:6047-6052). An expression construct for in vivo production of siRNA molecules can include one or more siRNA encoding sequences operably linked to elements necessary for the proper transcription of the siRNA encoding sequence(s), including, e.g., promoter elements and transcription termination signals. Preferred promoters for use in such expression constructs include the polymerase-III HI-RNA promoter (see, e.g., Brummelkamp et al., Science 2002; 296:550-553) and the U6 polymerase-III promoter (see, e.g., Sui et al., Proc. Natl. Acad. Sci. USA 2002; Paul et al., Nature Biotechnol. 2002; 20:505-508; and Yu et al., Proc. Natl. Acad. Sci. USA 2002; 99:6047-6052). An siRNA expression construct can further comprise one or more vector sequences that facilitate the cloning of the expression construct. Standard vectors that can be used include, e.g., pSilencer 2.0-U6 vector (Ambion Inc., Austin, Tex.).

(viii) Other Complement Inhibiting Agents

A variety of other complement inhibitors can be used in various embodiments of the disclosure. In some embodiments, the complement inhibitor is a naturally occurring mammalian complement regulatory protein or a fragment or derivative thereof. For example, the complement regulatory protein may be CR1, DAF, MCP, CFH, or CFI. In some embodiments, the complement regulatory polypeptide is one that is normally membrane-bound in its naturally occurring state. In some embodiments, a fragment of such polypeptide that lacks some or all of a transmembrane and/or intracellular domain is used. Soluble forms of complement receptor 1 (sCR1), for example, can also be used. For example the compounds known as TP10 or TP20 (Avant Therapeutics) can be used. C1 inhibitor (C1-INH) can also be used. In some embodiments a soluble complement control protein, e.g., CFH, is used. In some embodiments, the polypeptide is modified to increase its solubility.

Inhibitors of C1s can also be used. For example, U.S. Pat. No. 6,515,002 describes compounds (furanyl and thienyl amidines, heterocyclic amidines, and guanidines) that inhibit C1s. U.S. Pat. Nos. 6,515,002 and 7,138,530 describe heterocyclic amidines that inhibit C1s. U.S. Pat. No. 7,049,282 describes peptides that inhibit classical pathway activation. Certain of the peptides comprise or consist of WESNGQPENN (SEQ ID NO: 73) or KTISKAKGQPREPQVYT (SEQ ID NO: 74) or a peptide having significant sequence identity and/or three-dimensional structural similarity thereto. In some embodiments these peptides are identical or substantially identical to a portion of an IgG or IgM molecule. U.S. Pat. No. 7,041,796 discloses C3b/C4b Complement Receptor-like molecules and uses thereof to inhibit complement activation. U.S. Pat. No. 6,998,468 discloses anti-C2/C2a inhibitors of complement activation. U.S. Pat. No. 6,676,943 discloses human complement C3-degrading protein from *Streptococcus pneumoniae*.

In some embodiments, the complement inhibitor is a C5 inhibitor (i.e., an agent that inhibits activation and/or activity of C5, typically by binding to C5). In some embodiments the C5 inhibitor is an anti-C5 antibody such as eculizumab, an anti-C5 siRNA such as ALN-CC5 (Alnylam Pharmaceuticals), an anti-C5 polypeptide such as Coversin (Volution Immuno Pharmaceuticals, Ltd.), or an anti-C5 small molecule.

In some embodiments, the complement inhibitor is the LNP023 inhibitor described in, e.g., Schubart et al., PNAS 116:7926-7931 (2019).

VI. Pharmaceutical Compositions

Viral vectors and/or complement inhibitors described herein can be incorporated into pharmaceutical compositions. Such pharmaceutical compositions are useful for, among other things, administration and delivery to a subject in vivo or ex vivo. In some embodiments, pharmaceutical compositions also contain a pharmaceutically acceptable carrier or excipient. Such excipients include any pharmaceutical agent, e.g., a pharmaceutical agent that does not itself induce an immune response harmful to the individual receiving the composition, and which may be administered without undue toxicity. As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

Pharmaceutical compositions may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In some embodiments, a pharmaceutical composition may be a lyophilized powder.

Pharmaceutical compositions can include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration can comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran. Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility to allow for the preparation of highly concentrated solutions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. Such labeling can include amount, frequency, and method of administration.

Pharmaceutical compositions and delivery systems appropriate for the compositions, methods and uses of the disclosure are known in the art (see, e.g., Remington: The Science and Practice of Pharmacy. 21st Edition. Philadelphia, PA. Lippincott Williams & Wilkins, 2005).

VII. Combination Therapy

In some aspects, methods of the present disclosure involve administering one or more complement inhibitors (e.g., a complement inhibitor described herein) to a subject receiving, or who has previously received, gene therapy (e.g., a viral vector described herein). In some methods, one or more complement inhibitors and a gene therapy (e.g., a viral vector) are administered to a subject.

In some embodiments, the complement inhibitor is administered to a subject who has received or is concurrently or sequentially receiving one or more doses of gene therapy. In some embodiments, the gene therapy is a viral vector, e.g., an AAV vector. In some embodiments, a subject has received gene therapy 1 day, 1 week, 2 weeks, 4 weeks, 2 months, 4 months, 6 months, or more prior to administration of a complement inhibitor.

In some embodiments, a complement inhibitor is administered to a subject who has not been receiving gene therapy. In some embodiments, a subject has not received gene therapy for about 1 day, 1 week, 2 weeks, 4 weeks, 2 months, 4 months, 6 months, 1 year, 2 years, 5 years, or more prior to administration of a complement inhibitor. In some embodiments, the subject has never received gene therapy.

In some embodiments, a complement inhibitor and a gene therapy are administered to a subject. In some embodiments, the complement inhibitor and the gene therapy are administered concurrently (e.g., within about 1 minute, 5 minutes, 10 minutes, 15 minutes, 30 minutes, 45 minutes, 1 hour, or 2 hours of each other). In some embodiments, the complement inhibitor and the gene therapy are administered sequentially (e.g., more than 1 hour, 6 hours, 12 hours, 18 hours, 24 hours, 2 days, 3 days, 4 days, 5 days, 6 days, 7 days, 2 weeks, 4 weeks, or more, apart).

In some embodiments, a subject is pretreated with a complement inhibitor before receiving a gene therapy. In some embodiments, a complement inhibitor is administered to a subject 2, 4, 6, 8, 10, 12, 14, 16, 18, 20, or 24 hours before a gene therapy dose. In some embodiments, a complement inhibitor is administered to a subject more that 24 hours before a gene therapy dose.

In some embodiments, a subject may be administered a short course treatment of complement inhibitor (such as a C3 inhibitor, e.g., a LACA). In some embodiments, a short course treatment may include a single dose of complement inhibitior. In some embodiments, a short course treatment may include up to 2, 3, 4, 5, 6, 7, 8, 9, or 10 doses.

In some embodiments, a short course treatment is a treatment regimen in which the number of days between the first and last dose administered (including the day the first and last dose were administered) is 1, 2, 3, 4, 5, 6, or 7 days. In some embodiments, a short course treatment is a treatment regimen in which the number of days between the first and last dose administered (including the day the first and a last dose were administered) is up to 10, 14, 21, or 28 days.

In some embodiments, the complement inhibitor is initially administered followed by a period in which the complement is not administered to the subject for a longer time period, e.g., 6 months, 1 year, 2, 3, 4, 5 years, or more. In some embodiments, a subject who receives a gene therapy may be administered a single course of complement inhibitor therapy. In some embodiments a subject may be administered a second (or subsequent) course of complement inhibitor therapy in conjunction with receiving a second (or subsequent) dose (or doses) of a gene therapy.

In some embodiments, a short course treatment of a complement inhibitor may inhibit complement for a relatively short period of time (e.g., up to 12 or 24 hours, or up to 1, 2, 3, 4, 5, 6, or 7 days or up to 1, 2, 3, 4, 5, or 6 weeks) during a time in which one or more dose(s) of a gene thereapy, e.g., an AAV vector, is administered to a subject.

In some embodiments, a complement inhibitor is administered for a period of time in order to inhibit complement until the viral vector of the gene therapy is taken up by one or more target cells (e.g., taken up by a target cell by a certain level or extent). In some embodiments, cell uptake is indicated or measured in a subject using an assay to detect a decreased level of viral vector in a sample obtained from the subject (e.g., a serum sample) and/or increased level of viral vector in one or more target cells. Level of viral vector can be measured by any known method for detecting a viral vector in a sample (e.g., ELISA, PCR, etc.).

In some embodiments, a short course treatment may include an IV administration (e.g., by IV infusion) that lasts for, e.g., between 15 minutes and 48 hours, e.g., 30 minutes, 1 hour, 2 hour, 4-8 hours, 8-16 hours, 16-24 hours, 24-48 hours, or 48-72 hours. In some embodiments, the short course treatment by IV infusion may span the time in which a subject receives gene therapy. In some embodiments, the short course treatment by IV infusion may be before a subject receives gene therapy. In some embodiments, the short course treatment by IV infusion may be after a subject receives gene therapy.

In some embodiments, a subject may be administered a short course treatment of complement inhibitor before receiving a gene therapy. In some embodiments, a short course of complement inhibitor treatment may be administered between 15 minutes and 48 hours, e.g., 30 minutes, 1 hour, 2 hour, 4-8 hours, 8-16 hours, 16-24 hours, 24-48 hours, or 48-72 hours, before a subject receives a gene therapy treatment.

In some embodiments, a subject may be administered a short course treatment of complement inhibitor after receiving a gene therapy. In some embodiments, a short course of complement inhibitor treatment may be administered between between 15 minutes and 48 hours, e.g., 30 minutes, 1 hour, 2 hour, 4-8 hours, 8-16 hours, 16-24 hours, 24-48 hours, or 48-72 hours after a subject has received a gene therapy treatment.

In some embodiments, a complement inhibitor is administered in conjunction with immunosuppressive therapy.

In some embodiments, the combination therapy results in improved of the gene therapy (e.g., an improvement in a disease or disorder described herein or a symptom thereof) in a subject over a specified time period (e.g., over 1 week, 2 weeks, 3 weeks, 4 weeks, 6 weeks, 8 weeks, 3 months, 4 months, 6 months, 12 months, 24 months, 3 years, 4 years, 5 years, or more), relative to a subject receiving only the gene therapy. In some embodiments, gene therapy is administered to a subject receiving a complement inhibitor. In some embodiments, a complement inhibitor is administered to a subject receiving gene therapy.

In some embodiments, the combination therapy results in reduced side effects of the gene therapy (e.g., reduced immune response to a viral vector) in a subject over a specified time period (e.g., over 1 week, 2 weeks, 3 weeks, 4 weeks, 6 weeks, 8 weeks, 3 months, 4 months, 6 months, 12 months, 24 months, 3 years, 4 years, 5 years, or more), relative to a subject receiving only the gene therapy. In some embodiments, gene therapy is administered to a subject receiving a complement inhibitor. In some embodiments, a complement inhibitor is administered to a subject receiving gene therapy.

In some embodiments, administration of a complement inhibitor allows a subject who has received a first dose of a gene therapy (e.g., a viral vector) to receive one or more additional doses of gene therapy. In some embodiments, the one or more additional doses of gene therapy may be administered at least 6 months, e.g., at least 1, 2, 3, 5, or more years after the first dose of the gene therapy.

In some embodiments, a complement inhibitor is administered with a first dose of viral vector, e.g., AAV vector. In some such embodiments, the initial combination allows administration of one or more additional doses of the AAV vector.

In some embodiments, the one or more additional dose(s) of gene therapy comprise(s) a gene therapy using a viral vector of the same serotype as the gene therapy of the first dose. In some embodiments the one or more additional dose(s) of gene therapy comprise(s) a gene therapy using a viral vector with the same viral capsid and/or envelope as the the viral vector in the first dose.

In some embodiments, the one or more additional dose(s) of gene therapy comprise(s) a gene therapy using a viral vector of a different serotype than the viral vector used in the first dose. In some embodiments the one or more additional dose(s) of gene therapy comprise(s) a gene therapy using a viral vector with a different viral capsid and/or envelope than the viral vector used in the first dose.

In some embodiments, the one or more additional dose(s) of gene therapy comprise a gene therapy using the same transgene as the first dose. In some embodiments, the one or more additional dose(s) of gene therapy comprises a gene therapy using a different transgene than the first dose. In some embodiments, the subject does not have detectable preexisting antibodies to the gene therapy (e.g., viral vector).

In some embodiments, the age of the subject is less than 12 years. In some embodiments, the age of the subject is between 1-12 years. In some embodiments, the age of the subject is between 6-12 years. In some embodiments, the age of the subject is between 12-18 years. In some embodiments the age of the subject is greater than 12 years. In some embodiments, the age of the subject is greater than 18 years.

In some embodiments, combined administration of a complement inhibitor described herein and a gene therapy described herein results in an improvement in a disease or disorder described herein or a symptom thereof to an extent that is greater than one produced by either the gene therapy or the complement inhibitor alone. The difference between the combined effect and the effect of the gene therapy or complement inhibitor alone can be a statistically significant difference. In some embodiments, the combined result is synergistic.

In some embodiments, combined administration of a complement inhibitor and gene therapy allows administration of the gene therapy at a reduced dose, at a reduced number of doses, and/or at a reduced frequency of dosage compared to an effective dosing regimen for the gene therapy alone, and/or compared to a standard dosing regimen approved for the gene therapy. In some embodiments, combined administration of a complement inhibitor and the gene therapy allows administration of the complement inhibitor at a reduced dose, at a reduced number of doses, and/or at a reduced frequency of dosage compared to an effective dosing regimen for the complement inhibitor alone.

In some embodiments, efficacy of gene therapy and/or complement inhibitor is assessed at, e.g., 1 week, 2 weeks, 3 weeks, 4 weeks, 6 weeks, 8 weeks, 3 months, 6 months, or longer after administration of therapy.

In some embodiments, efficacy of gene therapy and/or complement inhibitor is measured or indicated by a disease sign or symptom recurrence-free period relative to a subject receiving only gene therapy or complement inhibitor. In some embodiments, efficacy of gene therapy and/or complement inhibitor is measured or indicated by increased time to recurrence of a disease sign or symptom relative to a subject receiving only gene therapy or complement inhibitor.

In some embodiments, efficacy of gene therapy and/or complement inhibitor is measured or indicated by a decrease in humoral response and/or a decrease in cellular response relative to a subject receiving only gene therapy and/or complement inhibitor. In some embodiments, decrease in humoral response is measured or indicated by decrease in magnitude of response or fold decrease from baseline of antibody (e.g., neutralizing antibody) levels. In some embodiments, antibody level is level of antibody against viral vector, e.g., capsid protein. In some embodiments, baseline is a value, level, amount or quantity measured or indicated in a subject (having a disease or disorder described herein) prior to administration of gene therapy and/or complement inhibitor. In some embodiments, baseline is a value, level, amount or quantity measured or indicated in a subject (not having a disease or disorder described herein) prior to administration of gene therapy and/or complement inhibitor. In some embodiments, decreased humoral response is indicated by a decrease in antibody titer from baseline of at least 10%, 20%, 30%, 40%, 50%, 60%, 70%, 80%, 90%, or 100%.

In some embodiments, cellular response is indicated or measured by secretion of granzyme B (GrB) and/or IFNγ. In some embodiments, decrease in cellular response is measured or indicated by decrease in magnitude of response or fold decrease from baseline of GrB and/or IFNγ levels. In some embodiments, decreased cellular response is indicated by a decrease in GrB and/or IFNγ levels from baseline of at least 10%, 20%, 30%, 40%, 50%, 60%, 70%, 80%, 90%, or 100%. In some embodiments, baseline is a value, level, amount or quantity measured or indicated in a subject (having a disease or disorder described herein) prior to administration of gene therapy and/or complement inhibitor. In some embodiments, baseline is a value, level, amount or quantity measured or indicated in a subject (not having a disease or disorder described herein) prior to administration of gene therapy and/or complement inhibitor.

In some embodiments, efficacy of gene therapy is measured by level of presence or expression of a transgene described herein, and/or level or activity of a protein encoded by a transgene described herein. For example, combined therapy of a complement inhibitor and gene therapy results in a level of transgene in a subject (e.g., in a cell or tissue of the subject) at, e.g., 1 week, 2 weeks, 3 weeks, 4 weeks, 6 weeks, 8 weeks, 3 months, 6 months, or longer after combined therapy, that is at least 10%, 20%, 30%, 40%, 50%, 60%, 70%, 80%, 90%, 100%, 125%, 150%, 175%, 200%, or more, higher relative to a corresponding level of transgene in a subject not administered the complement inhibitor. In some embodiments, combined therapy of a complement inhibitor and gene therapy results in a level of expression of transgene (and/or level of activity of a protein encoded by the transgene) in a subject (e.g., in a cell or tissue of the subject) at, e.g., 1 week, 2 weeks, 3 weeks, 4 weeks, 6 weeks, 8 weeks, 3 months, 6 months, or longer after combined therapy, that is at least 10%, 20%, 30%, 40%, 50%, 60%, 70%, 80%, 90%, 100%, 125%, 150%, 175%, 200%, or more, higher relative to a corresponding level of expression and/or activity in a subject not administered the complement inhibitor.

In some embodiments, the efficacy of gene therapy is measured by a stable level of expression of the transgene in the subject over a period of, e.g., 1 week, 2 weeks, 3 weeks, 4 weeks, 6 weeks, 8 weeks, 3 months, 6 months, or longer, relative to a corresponding level of expression of the transgene over the same period in a control subject (e.g., a control subject receiving the gene therapy and not administered the complement inhibitor). In some embodiments, a stable level of expression is a level of expression that differs by no more than 30%, 25%, 20%, 15%, 10%, or 5% over a defined period of time.

In some embodiments, efficacy of gene therapy with a transgene that encodes an inhibitor of a target gene or polypeptide is measured by level of expression of a target gene and/or level of expression and/or activity of a target polypeptide. In some embodiments, combined therapy of a complement inhibitor and gene therapy results in a level of expression of a target gene and/or level of expression and/or activity of a target polypeptide in a subject (e.g., in a cell or tissue of the subject) at, e.g., 1 week, 2 weeks, 3 weeks, 4 weeks, 6 weeks, 8 weeks, 3 months, 6 months, or longer after combined therapy, that is at least 10%, 20%, 30%, 40%, 50%, 60%, 70%, 80%, 90%, or 100% lower relative to a corresponding level of expression and/or activity in a subject not administered the complement inhibitor.

Gene therapy and/or complement inhibitor can be administered by any suitable route. The route and/or mode of administration can vary depending upon the desired results. Methods and uses of the disclosure include delivery and administration systemically, regionally or locally, or by any route, for example, by injection or infusion. The mode of administration is left to the discretion of the practitioner. Delivery of a pharmaceutical composition in vivo may generally be accomplished via injection using a conventional syringe, although other delivery methods such as convection-enhanced delivery can also be used (see, e.g., U.S. Pat. No. 5,720,720). For example, compositions may be delivered subcutaneously, epidermally, epidurally, intracerebrally, intradermally, intranasally, intrathecally, intraorbitally, intramucosally, intraperitoneally, intravenously, intrapleurally, subretinally, intraarterially, sublingually, intrahepatically, via the portal vein, and intramuscularly. Other modes of administration include oral and pulmonary administration, suppositories, and transdermal applications. A clinician may determine the optimal route for administration.

In some embodiments, gene therapy and complement inhibitor are administered by the same route. In some embodiments, gene therapy and complement inhibitor are administered by different routes.

The disclosure also provides methods for introducing viral vectors and complement inhibitors described herein into a cell or an animal. In some embodiments, such methods include contacting a subject (e.g., a cell or tissue of a subject) with, or administering to a subject (e.g., a subject such as a mammal), a complement inhibitor and a viral vector (e.g., an AAV vector) comprising a transgene such that the transgene is expressed in the subject (e.g., in a cell or tissue of a subject). In another embodiment, a method includes providing cells of an individual (patient or subject such as a mammal) with a complement inhibitor and a viral vector (e.g., an AAV vector) comprising a transgene described herein, such that the transgene is expressed in the individual.

Compositions of a vector (e.g., an AAV vector) comprising a transgene described herein can be administered in a sufficient or effective amount to a subject in need thereof. Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of transgene expression required to achieve a therapeutic effect, the specific disease treated, and the stability of the transgene expressed. One skilled in the art can determine an AAV/vector genome dose range to treat a patient having a particular disease or disorder based on the aforementioned factors, as well as other factors. Generally, doses will range from at least $1\times10^{8}$, or more, for example, $1\times10^{9}$, $1\times10^{10}$, $1\times10^{11}$, $1\times10^{12}$, $1\times10^{13}$, $1\times10^{14}$, or more, vector genomes per kilogram (vg/kg) of the weight of the subject, to achieve a therapeutic effect.

An effective amount or a sufficient amount can (but need not) be provided in a single administration, or may require multiple administrations. For example, the amount may be proportionally increased as indicated by the need of the subject, type, status and severity of the disease treated or side effects (if any) of treatment. Determining a therapeutically effective dose is well within the capability of a skilled medical practitioner using the techniques and guidance provided in the disclosure.

In some embodiments, administration of a complement inhibitor described herein can reduce the amount and/or activity of C3 in the subject's blood sufficiently such that efficacy of a gene therapy is enhanced, as described herein. In some embodiments, the complement inhibitor is a LACA comprising an approximately 40 kD PEG and is administered subcutaneously at daily doses of, e.g., between 60 mg/day-150 mg/day, e.g., 60, 70, 80, 90, 100, 110, 120, 130, 140, or 150 mg/day. In certain embodiments the daily dose is between 150 mg/day-350 mg/day, e.g., 150,160,170,180 190, 200, 210, 220, 230, 240, 250, 260, 270, 280, 290, 300, 310, 320, 330, 340, 350, 400, 450, 500, 550, 600, 650, 700, 750, 800, 850, 900, 950, 1000, 1100, 1200 mg/day or more.

In some embodiments the dose of LACA is administered as a single daily dose, e.g., subcutaneously. In some embodiments a dose of LACA is administered as a single weekly dose, e.g., subcutaneously. In some embodiments, a complement inhibitor is administered to a subject 2, 4, 6, 8, 10, 12, 14, 16, 18, 20, or 24 hours before a gene therapy dose.

In some embodiments, a LACA is is administered as a single dose. In some embodiments, the single dose is a bolus. In some embodiments, a bolus is an amount of a LACA that is administered, e.g., by IV infusion or other route of administration, over about 30 minutes, 20 minutes, 10 minutes, 5 minutes, or less.

In some embodiments, the single dose is an infusion. In some embodiments, an infusion is an amount of a LACA that is administered by infusion over about 15 minutes, 30 minutes, 45 minutes, 1 hour, 2 hours, 4 hours, 8 hours, 12 hours, 24 hours, 48 hours, 72 hours, or more.

In some embodiments, a subject is monitored before and/or following treatment with a complement inhibitor for level of C3 expression and/or activity, e.g., as measured using an alternative pathway assay, a classical pathway assay, or both. Suitable assays are known in the art and include, e.g., a hemolysis assay. In some embodiments, a subject is treated with a complement inhibitor, or is retreated with a complement inhibitor, if a measured level of C3 expression and/or activity is more than 10%, 20%, 30%, 40%, 50%, 100%, 200%, or more, relative to measured level of C3 expression and/or activity in a control subject.

In some embodiments, a dosing regimen may be selected to achieve a selected level of complement inhibition (e.g., inhibition of the alternative pathway, classical pathway, or both), for a selected time period. In some embodiments the selected level of complement inhibition is at least 50%, 60%, 70%, 80%, 90%, or more. In some embodiments the selected time period may be, e.g., between 8 hours and 72 hours, e.g., between 12 hours and 48 hours, e.g., about 16, 20, 24, 28, 32, 36, 40, or 44 hours. In some embodiments the selected time period may be, e.g., between 44 and 72 hours, or between 72 and 128 hours.

In some embodiments, a method may comprise obtaining one or more samples, e.g., blood samples, from a subject to whom a complement inhibitor has been administered and measuring the level of complement inhibition (e.g., expression and/or activity of C3) using one or more assays. In some embodiments, complement inhibitor therapy may be continued until a selected level of inhibition has been achieved. Following achievement of such selected level of inhibition, one or more doses of a gene therapy may be administered. The subject may continue to receive complement inhibitor therapy during and/or following administration of the one or more doses(s) of gene therapy.

In some embodiments, a method may comprise alternatively or additionally monitoring a subject for signs and/or symptoms associated with complement activation during or following administration of a gene therapy. In some embodiments, e.g., if one or more signs or symptoms of complement activation is detected, e.g., if complement activation at or above a reference level is detected, the dose of complement inhibitor may be increased or one or more additional doses may be administered. In some embodiments, e.g., if one or more signs of complement activation is not detected, e.g., if complement activation remains below a reference level, the dose of complement inhibitor may be decreased or maintained at the same level or no additional doses may be administered. In some embodiments the reference level may be, e.g., a level of complement activation measured in that particular subject prior to administration of the gene therapy, typically when the subject is not suffering from an infection or other stimulus that may activate complement. In some embodiments the reference level may be an upper limit of the normal range as measured in the general population.

In some embodiments, the dose of complement inhibitor administered during a period of administration may remain the same or approximately the same during the period of administration. In some embodiments the dose administered during such period of administration may change during the period of administration.

In some embodiments, a complement inhibitor is administered as two or more doses. In some embodiments, a first dose (e.g., a loading dose) and a second dose (e.g., a maintenance dose) are administered. In some embodiments, a first dose is a bolus, and a second dose is a bolus. In some embodiments, the first dose is a bolus, and the second dose is an infusion. In some embodiments, the first dose is an infusion, and the second dose is an infusion. In some embodiments, the first dose is an infusion and the second dose is a bolus. In some embodiments, one or more doses of a complement inhibitor is administered as an infusion over a period of about 15 minutes to about 48 hours, e.g., about 30 minutes, about 1 hour, 2 hours, 4 hours, 8 hours, 12 hours, 18 hours, 24 hours, 36 hours, or 48 hours. In some embodiments, the first dose comprises about 10 mg to about 1200 mg, e.g., about 10 mg to about 600 mg of a LACA (e.g., about 10-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-220 mg, about 220-240 mg, about 240-260 mg, about 260-280 mg, about 280-300 mg, about 300-320 mg, about 320-340 mg, about 340-360 mg, about 360-380 mg, about 380-400 mg, about 400-420 mg, about 420-440 mg, about 440-460 mg, about 460-480 mg, about 480-500 mg, about 500-520 mg, about 520-540 mg, about 540-560 mg, about 560-580 mg, about 580-600 mg) and the second dose comprises about 10 mg to about 600 mg of a LACA (e.g., about 10-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-220 mg, about 220-240 mg, about 240-260 mg, about 260-280 mg, about 280-300 mg, about 300-320 mg, about 320-340 mg, about 340-360 mg, about 360-380 mg, about 380-400 mg, about 400-420 mg, about 420-440 mg, about 440-460 mg, about 460-480 mg, about 480-500 mg, about 500-520 mg, about 520-540 mg, about 540-560 mg, about 560-580 mg, about 580-600 mg). It will be appreciated that maintenance doses may continue to be administered for as long as desired, e.g., up to 1 week, 10 days, 2 weeks, etc.

In some embodiments, a subject may be administered a loading dose of a complement inhibitor, which loading dose is followed by administration of one or more maintenance doses, e.g., at a different dosage level. In some embodiments a loading dose contains a greater amount of complement inhibitor than one or more maintenance doses.

In some embodiments, the loading dose may be determined based on the level of complement activitiy (e.g., C3). In some embodiments, one or more maintenance dose may be determined based on the level of complement activitiy (e.g., C3).

In some embodiments, the loading dose is administered before administration of a gene therapy to a subject. In some embodiments, a loading dose of complement inhibitor is administered to a subject 2, 4, 6, 8, 10, 12, 14, 16, 18, 20, or 24 hours before a gene therapy dose. In some embodiments, a loading dose of complement inhibitor is administered to a subject 2, 4, 6, 8, 10, 12, 14, 16, 18, 20, or 24 hours before a gene therapy dose. In some embodiments, the loading dose is administered after administration of a gene therapy to a subject. In some embodiments, at least one maintenance dose is administered before administration of a gene therapy to a subject. In some embodiments, at least one maintenance dose is administered after administration of a gene therapy to a subject. In some embodiments, a subsequent dose of gene therapy (e.g., AAV vector) is administered after at least one maintenance dose. In some embodiments, at least one subsequent maintenance dose is administered following a subsequent dose of gene therapy.

In some embodiments, a maintenance dose may include one or more dose(s) of complement inhibitor. In some embodiments, a maintenance dose consists of multiple doses administered over a period time of between 8 hours and 72 hours, e.g., between 12 hours and 48 hours, e.g., about 16, 20, 24, 28, 32, 36, 40, 44, or 48 hours. In some embodiments the selected time period may be, e.g., between 44 and 72 hours, or between 72 and 128 hours.

In some embodiments, a maintenance dose may include an IV administration (e.g., by IV infusion) that lasts for, e.g., between 15 minutes and 48 hours, e.g., 30 minutes, 1 hour, 2 hour, 4-8 hours, 8-16 hours, 16-24 hours, 24-48 hours, or 48-72 hours. In some embodiments, the maintenance dose by IV infusion may span the time in which a subject receives gene therapy.

In some embodiments, a complement inhibitor is administered according to a dosing regimen described in, e.g., WO2018/187813 or WO2019/118938.

In certain embodiments a LACA comprising a PEG of about 40 kD may be used. In some embodiments a method, formulation, and/or a dosing regimen, e.g., a dosing regimen suitable for subcutaneous administration, described in US Pub. No. 20190381129, US Pub. No. 20200038516, and/or WO/2019/118938 may be used. For example, any of the following doses may be used in various embodiments: In some embodiments the LACA may be administered thrice weekly in an amount between 545 mg and 1690 mg per dose. In some embodiments the LACA is administered thrice weekly in an amount between 630 mg and 930 mg per dose. In some embodiments the LACA is administered thrice weekly in an amount between 795 mg and 885 mg per dose. In some embodiments the LACA is administered twice weekly in an amount between 585 mg and 2510 mg per dose. In some embodiments the LACA is administered twice weekly in an amount between 900 mg and 1395 mg per dose. In some embodiments the LACA is administered twice weekly in an amount between 990 mg and 1215 mg per dose. In some embodiments the LACA is administered twice weekly in an amount between 1215 mg and 1395 mg per dose. In some embodiments the LACA is administered weekly in an amount between 1080 mg and 5040 mg per dose. In some embodiments the LACA is administered weekly in an amount between 2160 mg and 2520 mg per dose. In some embodiments the LACA is administered weekly in an amount between 2520 mg and 2880 mg per dose. In some embodiments the LACA is administered weekly in an amount between 2880 mg and 3240 mg per dose. In some embodiments the LACA is administered weekly in an amount between 3240 mg and 3600 mg per dose. In some embodiments the LACA is administered in a dose of about 1080 mg twice weekly, thrice weekly, or every three days. In some embodiments such administration is subcutaneous. Dosing regimens comprising alternate day administration may be used in some embodiments.

In certain embodiments, a LACA comprising a PEG of about 40 kD may be administered intravenously. In some embodiments an initial dose of about 1-2 grams, or more, e.g., up to about 4-5 grams, or up to about 6.0 grams, or up to about 10 grams may be administered. In some embodiments the dosing regimen comprises a single dose of the LACA administered IV. In some embodiments the IV dosing regimen comprises an initial IV dose of the LACA and one or more additional doses, e.g., administered IV. In some embodiments the dosing regimen comprises a loading dose of the LACA and one or more additional doses. In some embodiments a single dose and/or loading dose and/or additional dose of the LACA is between about 4.0 g and about 6.0 g, e.g., between about 4.5 g and about 5.5 g, e.g., about 5.0 g. In some embodiments a single dose and/or initial dose and/or additional dose of the LACA is between about 5.0 g and about 7.0 g, e.g., about 5.0 g, about 5.5 g, about 6.0 g, about 6.5 g, or about 7.0 g. In some embodiments a single dose and/or initial dose and/or additional dose is between about 8.0 g and about 10.0 g, e.g., about 8.0 g, about 8.5 g, about 9.0 g, about 9.5 g, or about 10.0 g. In some embodiments a dose between about 4.0 g and about 10.0 g, e.g., about 5.0 g, about 6.0 g, about 7.0 g, about 8.0 g, about 8.5 g, about 9.0 g, about 9.5 g, or about 10.0 g is administered IV. In some embodiments an additional such dose may be administered about 5-10 days later, e.g., about 6, about 7, about 8, or about 9 days later. In some embodiments the second dose may be followed by one or more additional such doses, e.g., at the same dosing interval.

In some embodiments a first dose may be administered intravenously and SC treatment may be started at about the same time. In some embodiments a first dose may be administered intravenously and SC treatment may be started within about 24, 48, 72, or 96 hours of the IV dose. In an exemplary embodiment a LACA comprising a PEG of about 40 kD is administered at about 4,000 mg IV dose. In another exemplary embodiment the LACA is administered IV at about a 2,000 mg dose and SC at a 1,300 mg dose. In some embodiments the SC dose may, for example, be administered within or about one hour after the IV dose. The SC dose may, for example, be administered over a period of up to an hour. The patient may then receive further doses of the LACA SC, according to any of the afore-mentioned dosing regimens, e.g., 1,080 mg twice weekly or 1,080 mg every three days or 1,080 mg thrice weekly or 1,080 mg every other day. In some embodiments, the LACA is administered IV as a loading dose of between about 0.5 g and about 2.5 g, and the patient may then receive further doses of the LACA SC, according to any of the afore-mentioned dosing regimens, e.g., 1,080 mg twice weekly or 1,080 mg every three days or 1,080 mg thrice weekly or 1,080 mg every other day. As will be appreciated, as described in WO2019118938 the doses for a twice weekly or thrice weekly dosing regimen will be spaced apart such that there are one or two intervening days on which doses are not administered (e.g., a dose may be administered on Days 1 and 4 of each week for a twice weekly dosing regimen or Days 1, 4, and 6 or Days 1, 3, and 5 of each week for a thrice weekly dosing regimen).

In some embodiments, a compstatin analog, e.g., a LACA comprising a PEG of about 40 kD, is administered daily. In some embodiments, a compstatin analog, e.g., a LACA comprising a PEG of about 40 kD, is administered daily at a dose of between about 270 mg and about 440 mg, e.g., about 270 mg daily or about 360 mg daily. In some embodiments such administration is via the SC route. In some embodiments, a LACA comprising a PEG of about 40 kD is administered IV as a loading dose of between about 0.5 g and about 2.5 g, and a maintenance dose of between about 270 mg and about 440 mg daily, e.g., about 270 mg daily or about 360 mg daily, is administered subcutaneously.

All publications, patent applications, patents, and other references mentioned herein, including GenBank Accession Numbers, are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLE

Example 1: Complement Inhibition Enhances the Efficiency of AAV Transduction A transduction assay was performed using AAV3b vector with a lacZ reporter and HuH7 cells cultured in medium containing varying amounts of the PEGylated compstatin analog (CA) of FIG. 1 having a PEG of about 10 kD.

Methods

1. Serial dilutions of non-human primate (NHP) serum were prepared with DMEM (1/10, 1/20, 1/40, 1/80, 1/160, and 1/320). 60 μl of each serum dilution was added to each well of a 96-well plate.
2. The serial dilutions of NHP serum were incubated with the CA (at 0, 10, and 100 μm) at 4° C. for 30 minutes.
3. 60 μl of AAV3b lacZ particles were added to each well and incubated at 37° C. for 60 minutes.
4. 100 μl of the media (containing serum, DMEM, CA, and AAV3b lacZ particles) were moved from each well and added to each well of a cell plate containing HuH7 cells.
5. The final volume of each well in the cell plate was 260 μl and the AAV3b particles were transduced into the HuH7 cells at an MOI of 10,000.
6. The HuH7 cells were incubated with the AAV3b lacZ overnight.

Figure 2:
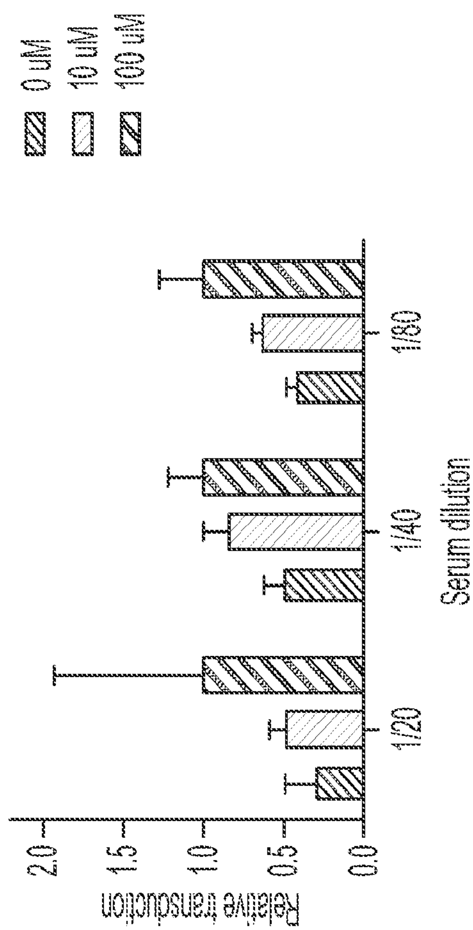
FIG. 2 is a graph comparing the relative transduction efficiency of AAV3b viral particles incubated in culture medium containing 1/20, 1/40, and 1/80 serum dilutions and different amounts (0, 10, and 100 μm) of the PEGylated compstatin analog (CA) of FIG. 1 having a PEG of about 10 kD and delivered to HuH7 cells. Results shown are normalized to the values from the 100 μM CA samples.
Figure 3:
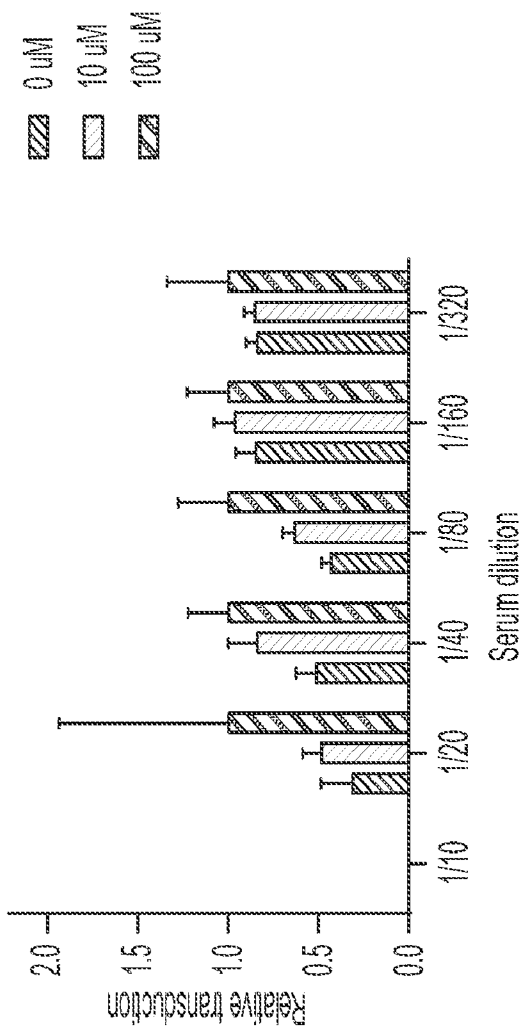
FIG. 3 is a graph comparing the relative transduction efficiency of AAV3b viral particles incubated in culture medium containing 1/20, 1/40, and 1/80 serum dilutions and different amounts (0, 10, and 100 μm) of the PEGylated compstatin analog (CA) of FIG. 1 having a PEG of about 10 kD and delivered to HuH7 cells. Results shown are normalized to the values from the 100 μM CA samples.

Absorbance was measured and data was represented as relative transduction rate normalized to the values from the 100 μm CA samples (as shown in FIGS. 2 and 3).

FIGS. 2 and 3 contain graphs comparing the relative transduction efficiency of AAV3b viral particles in culture medium containing 1/20, 1/40, and 1/80 (and 1/10, 1/160, and 1/320 in FIG. 3) serum dilutions and different amounts (0, 10, and 100 μm) of the PEGylated compstatin analog (CA) of FIG. 1 having a PEG of about 10 kD and delivered to HuH7 cells.

There was no detectable transduction at serum dilutions of 1/10 and no significant difference between groups with serum diluations of greater than 1/80.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of improving efficacy of a gene therapy in a subject receiving or who has received the gene therapy, the method comprising administering a complement inhibitor to the subject, thereby improving efficacy of the gene therapy; wherein the complement inhibitor comprises a compstatin analog, wherein the compstatin analog comprises a clearance reducing moiety (CRM) comprising a PEG of about 40 kD, and wherein the compstatin analog has the following structure:

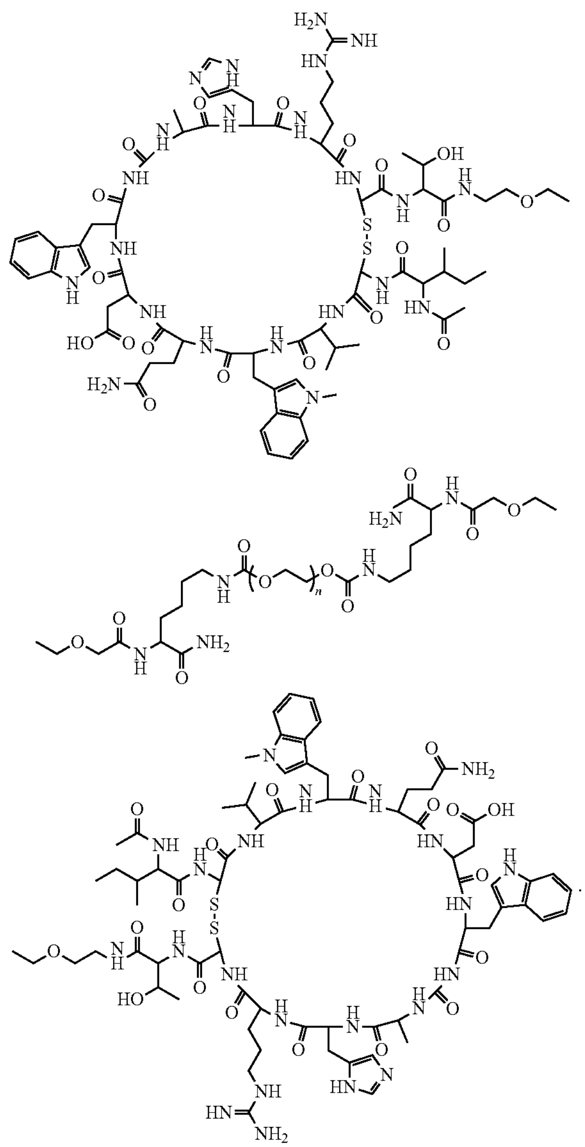

2. The method of claim 1, wherein the efficacy of the gene therapy is improved in the subject over a specified time period relative to a control subject receiving or who has received the gene therapy and is not administered the complement inhibitor.

3. The method of claim 1, wherein the gene therapy comprises a viral vector.

4. The method of claim 3, wherein the viral vector is an adeno-associated viral (AAV) vector.

5. The method of claim 3, wherein the viral vector comprises a transgene.

6. The method of claim 1, wherein the complement inhibitor decreases an immune response against the gene therapy, relative to a control subject receiving the gene therapy and not administered the complement inhibitor.

7. The method of claim 3, wherein transduction of the viral vector is improved, relative to a control subject receiving the gene therapy and not administered the complement inhibitor.

8. The method of claim 7, wherein transduction is assessed by measuring level of transgene expression.

9. The method of claim 3, wherein complement-mediated clearance of the viral vector is decreased relative to a control subject receiving the gene therapy and not administered the complement inhibitor.

10. The method of claim 1, wherein the complement inhibitor decreases the activity of a C3 protein.

11. A method of reducing complement activation in a subject who has received or is receiving gene therapy, the method comprising:

administering a gene therapy to the subject; and administering a complement inhibitor to the subject, thereby reducing complement activation in the subject; wherein the complement inhibitor comprises a compstatin analog, wherein the compstatin analog comprises a CRM comprising a PEG of about 40 kD, and wherein the compstatin analog has the following structure:

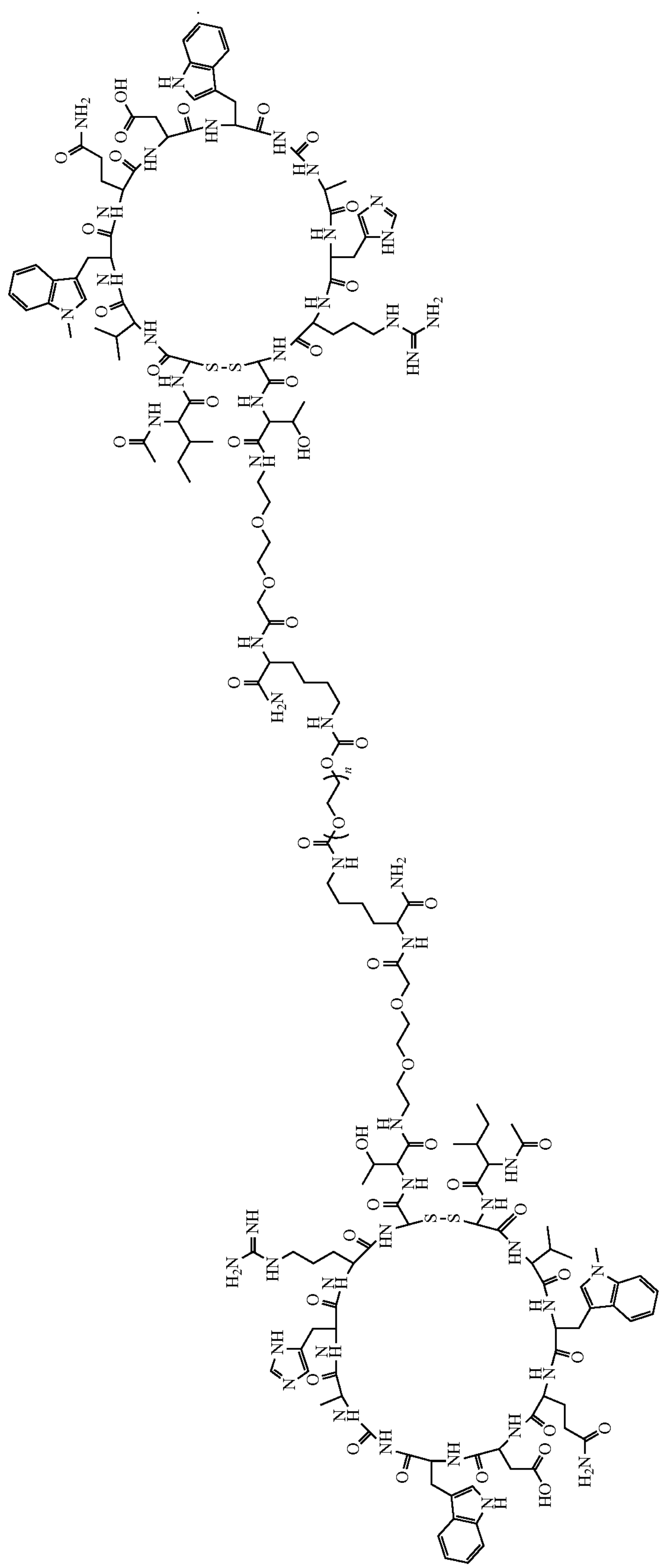

12. A method of increasing transduction of a viral vector comprising a transgene in a subject receiving gene therapy, the method comprising:

administering a complement inhibitor to the subject, wherein expression of the transgene in the subject is increased relative to a control subject receiving the gene therapy but not administered the complement inhibitor; wherein the complement inhibitor comprises a compstatin analog, wherein the compstatin analog comprises a CRM comprising a PEG of about 40 kD, and wherein the compstatin analog has the following structure:

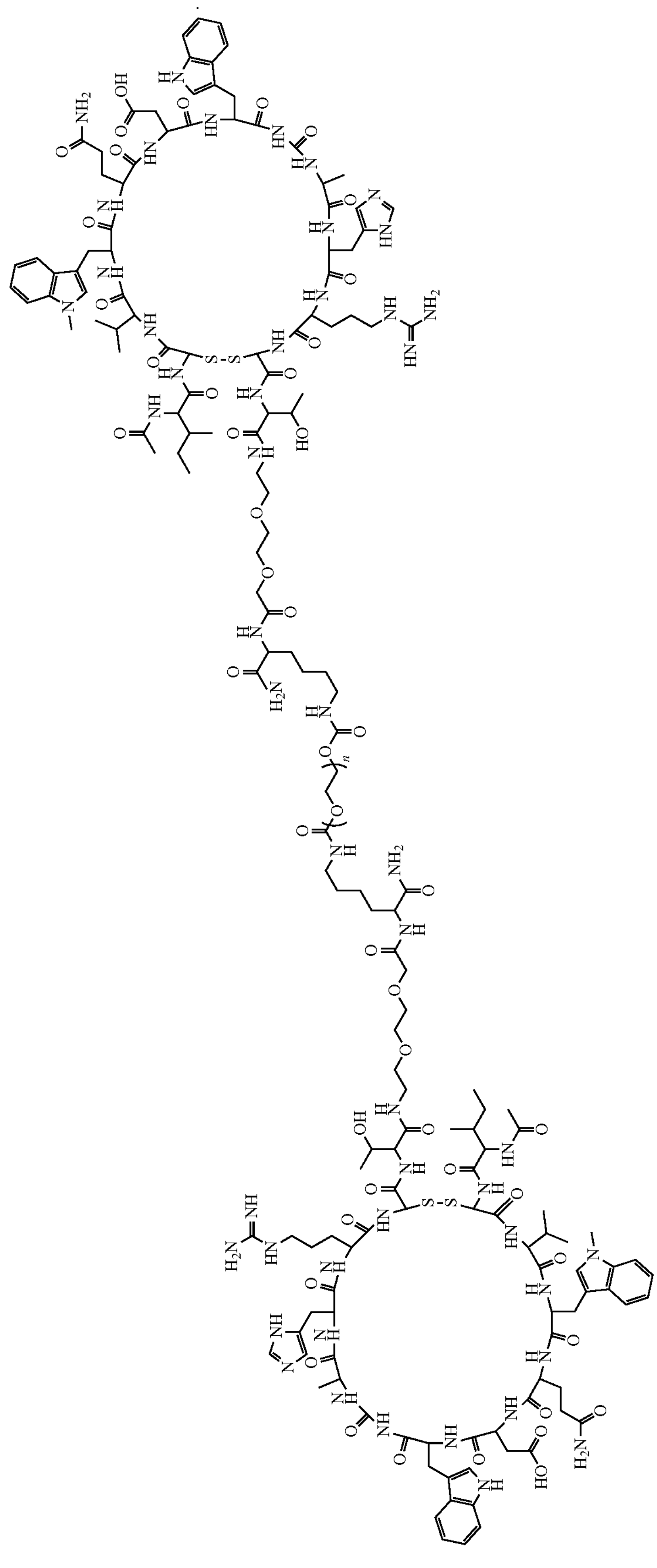

13. The method of claim 1, further comprising administering the gene therapy to the subject.

14. The method of claim 12, wherein the complement inhibitor decreases the activity of C3 protein.

15. The method of claim 12, wherein the viral vector is an adeno-associated viral (AAV) vector.

16. The method of claim 11, wherein complement activation is reduced in the subject over a specified time period relative to a control subject receiving or who has received the gene therapy and is not administered the complement inhibitor.

17. The method of claim 11, wherein the complement inhibitor decreases the activity of C3 protein.

18. The method of claim 11, wherein the gene therapy comprises a viral vector.

19. The method of claim 18, wherein the viral vector is an adeno-associated viral (AAV) vector.

20. The method of claim 18, wherein the viral vector comprises a transgene.

* * * * *